US012662661B2

(12) United States Patent
Houston et al.

(10) Patent No.: US 12,662,661 B2
(45) Date of Patent: Jun. 23, 2026

(54) ACETYL-TRANSFERASES

(71) Applicant: DSM IP Assets B.V., Heerlen (NL)

(72) Inventors: Peter Louis Houston, Boston, MA (US); René Marcel De Jong, Amsterdam (NL); Valmik Kanubhai Vyas, Winchester, MA (US); René Verwaal, Nootdorp (NL); Jenna McMahon, Tewksbury, MA (US); Anna Symbor-Nagrabska, Reading, MA (US)

(73) Assignee: DSM IP ASSETS B.V., Heerlen (NL)

( * ) Notice: Subject to any disclaimer, the term of this patent is extended or adjusted under 35 U.S.C. 154(b) by 939 days.

(21) Appl. No.: 17/419,079

(22) PCT Filed: Dec. 30, 2019

(86) PCT No.: PCT/EP2019/087183
§ 371 (c)(1),
(2) Date: Jun. 28, 2021

(87) PCT Pub. No.: WO2020/141168
PCT Pub. Date: Jul. 9, 2020

(65) Prior Publication Data
US 2022/0064607 A1 Mar. 3, 2022

(30) Foreign Application Priority Data

Dec. 31, 2018 (CH) ..................................... 01616/18

(51) Int. Cl.
| | |
|---|---|
| *C12N 9/10* | (2006.01) |
| *C12N 1/185* | (2026.01) |
| *C12P 7/62* | (2022.01) |
| *C12R 1/85* | (2006.01) |

(52) U.S. Cl.
CPC ........... *C12N 9/1029* (2013.01); *C12N 1/185* (2021.05); *C12P 7/62* (2013.01); *C12R 2001/85* (2021.05); *C12Y 203/01084* (2013.01)

(58) Field of Classification Search
CPC ......... C12N 9/1029; C12N 1/185; C12P 7/62; C12R 2001/85; C12Y 203/01084
See application file for complete search history.

(56) References Cited

U.S. PATENT DOCUMENTS

| | | | |
|---|---|---|---|
| 10,006,064 B2 | 6/2018 | Zhang et al. | |
| 10,465,174 B2 | 11/2019 | Farrell et al. | |
| 2007/0166782 A1 | 7/2007 | Keasling et al. | |
| 2014/0170720 A1 | 6/2014 | Kim et al. | |
| 2016/0130628 A1 | 5/2016 | Kim et al. | |
| 2020/0231993 A1* | 7/2020 | Balch et al. | ..... C12Y 203/0102 |

FOREIGN PATENT DOCUMENTS

| | | | | |
|---|---|---|---|---|
| JP | 2015-517824 | 6/2015 | | |
| JP | 2016-501543 | 1/2016 | | |
| WO | 2006/102342 | 9/2006 | | |
| WO | 2008/042338 | 4/2008 | | |
| WO | 2009/126890 | 10/2009 | | |
| WO | 2012/125027 | 9/2012 | | |
| WO | 2013/144257 | 10/2013 | | |
| WO | 2013/180810 | 12/2013 | | |
| WO | 2014/096992 | 6/2014 | | |
| WO | 2014/195378 | 12/2014 | | |
| WO | 2016/110512 | 7/2016 | | |
| WO | 2016/172282 | 10/2016 | | |
| WO | 2017/216392 | 12/2017 | | |
| WO | 2019/058000 | 3/2019 | | |
| WO | 2019/058001 | 3/2019 | | |
| WO | WO-2019058000 A1 * | 3/2019 | ........... | C12N 9/0006 |

OTHER PUBLICATIONS

Fujii et al., Applied and Environmental Microbiology , 1994, vol. 60, No. 8, pp. 2786-2792. (Year: 1994).*
SGD Strain Alignment, 2018, available at pp. 1-48 https://www.yeastgenome.org/strainAlignment?locus=Atf1&type=protein&submit=Submit#YOR377W_YPH499, accessed on May 31, 2024. (Year: 2018).*
Porter et al., Food Research International , v. 119, 2019, pp. 378-389. (Year: 2019).*
Nancolas et al., Yeast. 2017; 34: 239-251. (Year: 2017).*
GenCore., Sequence Alignment Balch's SEQ ID No. 38 vs. Instant SEQ ID No. 1, 2025. p. 1 (Year: 2025).*
GenCore1., Sequence Alignment Copending U.S. Appl. No. 18/292,227 SEQ ID No. 18 vs Instant SEQ ID No. 1, pp. 1-2 (Year: 2025).*
GenCore2., Sequence Alignment U.S. Pat. No. 12,252,724 B2 SEQ ID No. 33 vs Instant SEQ ID No. 1 (Year: 2025).*
GenCore3., Sequence Alignment U.S. Pat. No. 11578344B2 SEQ ID No. 33 vs Instant SEQ ID No. 1 (Year: 2025).*
Sequence Alignment Results Zhang's SEQ ID No. 66 vs. Instant SEQ ID No. 1 (Year: 2025).*
Trademark Search Results "PROSITE", retrieved from https://tmsearch.uspto.gov/search/search-results on Oct. 17, 2025, pp. 1-5 (Year: 2025).*
Ding, Bao-Jian et al, "The Yeast ATF1 Acetyltransferase Efficiently Acetylates Insect Pheromone Alcohols: Implications for the Biological Production of Moth Pheromones", Lipids (2016) 51:469-475.
International Search Report for PCT/EP2019/087183, mailed Mar. 18, 2020, 5 pages.
Written Opinion of the ISA for PCT/EP2019/087183, mailed Mar. 18, 2020, 5 pages.
Ausubel et al, "Current Protocols in Molecular Biology", Nov. 1988, 1600 pages.
Fitch et al, "Lrglp Is a Rhol GTPase-Activating Protein Required for Efficient Cell Fusion in Yeast", Genetics, vol. 168, pp. 733-746, Oct. 2004, 15 pages.
Gietz et al., "Transformation of Yeast by Lithium Acetate/Single-Stranded Carrier DNS/Polyethylene Glycol Method", Methods in Enzymology, vol. 350, pp. 87-96, 2002.
(Continued)

*Primary Examiner* — Lianko G Garyu
*Assistant Examiner* — Claudia Espinosa
(74) *Attorney, Agent, or Firm* — Nixon & Vanderhye, PC

(57) ABSTRACT
The present invention is related to production of retinyl acetate generated via enzymatic conversion of retinol, said process including the use of modified enzymes with improved activity.

20 Claims, 1 Drawing Sheet
Specification includes a Sequence Listing.

(56)        References Cited

OTHER PUBLICATIONS

Jang et al, "Selective Retinol Production by Modulating the Composition of Retinoids from Metabiolocally Engineered *E. coli*", Biotechnology and Bioengineering, vol. 112, No. 8, Aug. 2015, pp. 1604-1612.

Jang et al., "Retinoid production using metabolically engineered *Escherichia coli* with a two-phase culture system", Microbial Cell Factories, vol. 10, No. 1, XP021105369, pp. 1-12, 2011.

Löoke et al, "Extraction of Genomic DNA from Yeasts for PCR-Based Applications", Biotechniques. May 2011; 50 (5), pp. 325-328.

Mortimer et al, "Genealogy of Principal Strains of the Yeast Genetic Stock Center", Genetics, vol. 113, May 1986, pp. 35-43.

Needleman et al., "A General Method Applicable to the Search for Similarities in the Amino Acid Sequence of Two Proteins", Journal of Molecular Biology, vol. 48, 1970, pp. 443-453.

Rice et al., "EMBOSS: The European Molecular Biology Open Software Suite", TIG, Jun. 2000, vol. 16, No. 6, pp. 276-277.

Sambrook et al., "Molecular Cloning a Laboratory Manual", 1989, 30 pages.

Scan Prosite user manual, retrieved Jun. 28, 2021, 10 pages.

Sun et al, "Vitamin A Production by Engineered Saccharomyces cerevisiae from Xylose via Two-Phase in Situ Extraction", ACS Synthetic Biology, 2019, 10 pages.

Uniprot, C5DCK5, XP002798176, Jul. 28, 2009, 2 pages.

Van Dijken et al., "An interlaboratory comparison of physiological and genetic properties of four *Saccharomyces cerevisiae* strains", Enzyme and Microbial Technology, vol. 26, 2000, pp. 706-714.

Verwaal et al., "CRISPR/Cpfl enables fast and simple genome editing of *Saccharomyces cerevisiae*", Yeast, 2018, vol. 35, pp. 201-211_2018.

Verwaal et al., High-Level Production of Beta-Carotene in *Saccharomyces cerevisiae* by Successive Transformation with Carotenogenic Genes from Xanthophyllomyces dendrorhous, Applied and Environmental Microbiology, Jul. 2007, vol. 73, No. 13, pp. 4342-4350 2007.

GenBank: SCV03466.1_2016, "LAMI_0H08372g1_1 [Lachancea mirantina]" 2016, 1 page.

* cited by examiner

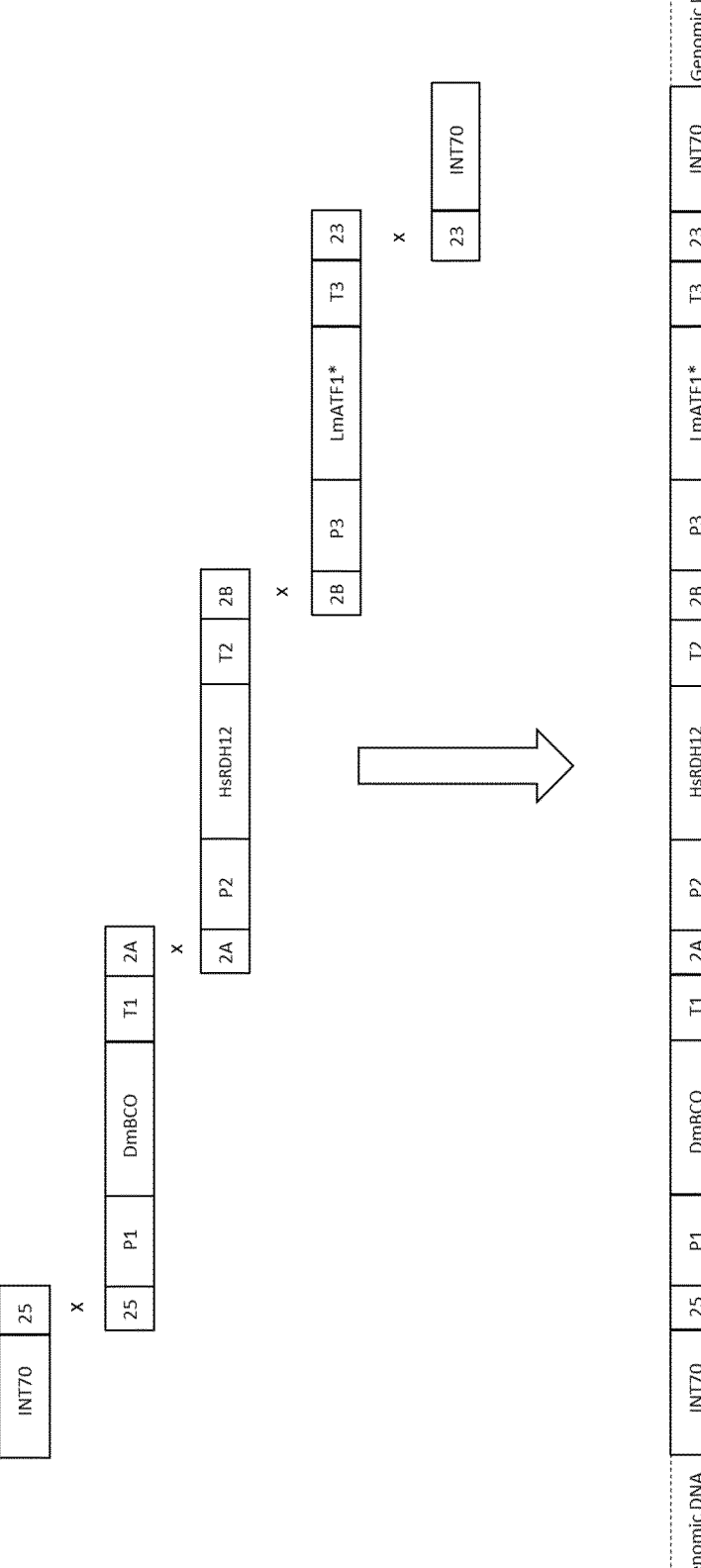

SEQUENCE LISTING

```
<160> NUMBER OF SEQ ID NOS: 60

<210> SEQ ID NO 1
<211> LENGTH: 559
<212> TYPE: PRT
<213> ORGANISM: Lachancea mirantina

<400> SEQUENCE: 1

Met Gly Asp Leu Asp Ala Arg Gly Thr Ser Ala His Pro Glu Leu Ser
1               5                   10                  15

Glu Arg Pro Ser Ile Met Pro Ser Met Ser Asp Ile Gln Asp Pro Ser
            20                  25                  30

Gly Asp Asp Lys Ala Thr Pro Arg Gly Ser Ala Ala Gly Leu Pro Gln
        35                  40                  45

Leu Glu Leu Ala Gly His Ala Arg Arg Leu Gly His Leu Glu Asn Phe
    50                  55                  60

Phe Ala Val Gln His Arg Gln Gln Ile Tyr Ser Ser Phe Ala Val Phe
65                  70                  75                  80

Cys Glu Phe Asp Thr Ala Cys Ser Leu Ala Gln Leu Ala Ser Ala Val
                85                  90                  95

Arg Asn Val Cys Leu Ser Asn Pro Leu Leu Leu His Thr Val Glu Pro
                100                 105                 110

Lys His Pro Asp Ile Ala Gly Phe Tyr His Ser Asp Glu Tyr Leu Ser
            115                 120                 125

Arg Pro Trp Pro Gln His Asp Tyr Met Arg Val Leu Arg Glu Val His
        130                 135                 140

Val Ala Asp Val Val Met Asn Gly Gln Lys Glu His Ala His Val Val
145                 150                 155                 160

Arg Asp Ala Val Asp Val Phe Gln Ala His Gly Asn Gln Val Thr Ser
                165                 170                 175

Glu Leu Leu Glu Leu Met Thr Gln Ile Glu Ile Pro His Ala Ser Gln
                180                 185                 190

Thr Arg Pro Ser Trp Arg Leu Leu Cys Phe Pro His Gly Glu Ala Asn
            195                 200                 205

Arg Trp Arg Thr Phe Ala Phe Val Ser Asn His Cys Ser Ser Asp Gly
        210                 215                 220

Leu Ser Gly Leu Asn Phe Phe Arg Asp Leu Gln Lys Glu Leu Ala His
225                 230                 235                 240

Gly Pro Thr Ser Gly Ala Pro Gly Ala Pro Gly Ala Ser Gly Val Ile
                245                 250                 255

Phe Asp Tyr Ala Gln Asp Ala Ala Thr Leu Pro Lys Leu Pro Pro Pro
                260                 265                 270

Ile Asp Gln Lys Leu Asp Tyr Arg Pro Ser Lys Lys Ala Leu Leu Gly
            275                 280                 285

Leu Leu Ala Gly Lys Phe Val Arg Glu Lys Leu Gly Tyr Val Ser Ala
        290                 295                 300

Ala Pro Pro Thr Thr Pro Thr Ser Asp Leu Ala His Pro Glu Gly His
```

```
305                    310                    315                    320
Gln Tyr Tyr Cys Tyr Leu Val Asn Val Pro Thr Ser Ser Val Ala His
                325                    330                    335

Ile Lys Thr Gln Val Arg Glu Asn Val Pro His Lys Cys Thr Leu Thr
            340                    345                    350

Pro Phe Leu Gln Ala Cys Trp Leu Val Ser Leu Phe Lys Tyr Gly Arg
            355                    360                    365

Val Phe Ser Gly Ser Trp Leu Glu Arg Tyr Thr Asp Val Leu Val Ala
        370                    375                    380

Met Asn Thr Arg Gln Leu Leu Pro Glu Asp Leu Glu Leu Gln Arg Gln
385                    390                    395                    400

Tyr Arg Tyr Gly Ser Asn Val Gly Gly Val Arg Tyr Asn Tyr Pro Ile
                405                    410                    415

Ala Pro Leu Asp Val Arg Asp Asn Asp Gln Lys Phe Trp Ser Leu Val
            420                    425                    430

Glu Ser Tyr Arg Leu Ala Leu Ser Asp Ala Arg Asp Lys Asn Asp Tyr
            435                    440                    445

Leu Tyr Ala Leu Gly Ala Leu Met Leu Pro Glu Ile Tyr Glu Lys Lys
        450                    455                    460

Asn Val Asp Ala Val Val Asn Asp Thr Ile Leu Asn Gln Arg Arg Ser
465                    470                    475                    480

Gly Thr Leu Ile Ser Asn Val Gly Tyr Val Arg Asp Glu Gln Pro Thr
                485                    490                    495

Ala Phe Ala Ile Lys Asn His Val Phe Ser Gln Gly Val Gly Ala Asn
            500                    505                    510

Arg Asn Ala Phe Val Leu Asn Ile Cys Ala Thr Asp Gln Gly Gly Leu
            515                    520                    525

Asn Ile Ala Ile Ser Ile Ala Lys Gly Thr Leu Ala Ser Arg Gln Glu
        530                    535                    540

Gly Gln Glu Leu Cys Asp Ile Phe Lys Ser Thr Leu Leu Arg Phe
545                    550                    555
```

<210> SEQ ID NO 2
<211> LENGTH: 1680
<212> TYPE: DNA
<213> ORGANISM: Lachancea mirantina

<400> SEQUENCE: 2

```
atgggtgatc tcgacgcgag gggaacatca gcgcacccgg agctctcgga gaggccaagc      60
atcatgccct cgatgtcgga tatccaggac ccaagcggcg acgacaaggc cacgccccgc     120
ggctccgccg cgggggctgcc gcagctcgag ctcgccggcc acgcccggcg cctgggccat     180
ttggagaatt tcttcgccgt ccagcaccgg cagcagatct attccagttt cgccgtgttc     240
tgcgagttcg acaccgcgtg ctcgctcgcg cagctcgcgt ccgctgtgcg aaacgtgtgt     300
ctttcgaacc cgctgctgct gcacaccgtc gagcccaagc accgggacat cgccggcttc     360
taccactccg acgaatatct gtcccgaccc tggccccagc acgactacat gcgcgttttg     420
cgcgaggtcc acgtcgccga cgtggtgatg aacggccaga agagcacgc gcatgtcgtg     480 cgcgacgccg tcgacgtttt ccaagcgcat ggaaaccagg tcaccagcga gctgctcgag     540
ctcatgaccc agattgagat cccgcacgct cccaaacga gacccagctg gaggttgctg     600
tgtttcccac acggcgaggc caaccggtgg cgcacgtttg cgtttgtatc caatcattgt     660
tccagcgacg gtctctcggg tctgaacttc tttcgggacc tgcaaaagga gctcgcgcac     720
```

```
ggccccacct cggggccccc cggggcccccg ggggcctccg gcgtcatctt cgactacgcc      780
caggacgccg caacactgcc caaactgccc ccacccattg accaaaaact cgattaccgt      840
ccgtccaaga aggccctttt gggactttttg gccggcaagt tcgtgcgtga aaaactcggc      900
tacgtatcgg ccgccccgcc aacgaccccg acctccgatt tggcgcaccc agaaggtcac      960
caatactact gctaccttgt aaacgtaccg acatctagtg tggcccacat caaaacgcaa     1020
gtgcgcgaaa atgtcccgca caaatgcacg ctgacgccat tcttacaggc atgctggctc     1080
gtgtcactgt tcaagtatgg tcgcgttttt tccggctcct ggctcgaacg atacacggac     1140
gttctcgtcg ctatgaacac ccggcaactg ttgcccgaag atttggaatt gcaacgccag     1200
taccgttacg gtagtaacgt gggaggggta cgttacaatt atccaatcgc accgctcgac     1260
gtccgcgaca acgaccagaa attctggtcc ctggtggaga gttaccgact ggcccttagc     1320
gacgcacgcg acaaaaatga ttacttgtac gcattgggtg ctctaatgct tccagagatc     1380
tacgaaaaaa aaaacgtcga tgctgtggtc aatgacacaa ttctgaacca gcgtcgttcc     1440
ggaacgttga tcagtaacgt cggctacgtg cgcgatgaac agcccactgc gtttgcaatt     1500
aagaatcatg tcttttcaca aggcgttggc gccaacagaa acgcatttgt gcttaacata     1560
tgtgccacgg accaaggcgg cctaaatatc gccatcagta tcgccaaggg aaccttggcg     1620
tctcgtcaag aaggccaaga actttgcgac atctttaaat caacgttact gcgattctaa     1680
```

<210> SEQ ID NO 3
<211> LENGTH: 1680
<212> TYPE: DNA
<213> ORGANISM: Artificial Sequence
<220> FEATURE:
<223> OTHER INFORMATION: Yarrowia codon optimized LmATF1

<400> SEQUENCE: 3

```
atgggtgatc tcgatgcccg aggaacctct gctcaccccg agctctctga gcgaccttct       60
attatgcctt ctatgtctga tattcaggac ccttctggtg atgacaaggc tactcccccga      120 ggatctgctg ctgggctgcc ccagcttgag cttgctggac acgcccgacg acttggccac      180
cttgagaact tctttgctgt ccagcaccga cagcagattt actcttcttt tgctgttttt      240
tgtgagtttg acactgcttg ttctctcgct cagcttgctt ctgctgtgcg aaacgtttgt      300
ctttctaacc cccttctcct tcacactgtt gagcctaagc accctgacat cgctggattc      360
taccactctg acgagtacct ttcccgacct tggcctcagc acgattacat gcgagttctt      420
cgagaggttc acgtcgctga cgttgttatg aacggacaga aggagcacgc tcacgttgtt      480
cgagatgctg ttgacgtttt tcaggctcac ggaaaccagg ttacttctga gctccttgag      540
cttatgactc agattgagat tcctcacgct tctcagactc gaccctcttg gcgacttctc      600
tgttttcccc acggagaggc taaccgatgg cgaacctttg cttttgtttc taaccactgt      660
tcttctgatg gtctttctgg tcttaacttc tttcgagatc tccagaagga gcttgctcac      720
ggccccacct ctggtgctcc tggtgccccc ggagcttccg gagttattttt cgattacgct      780 caggacgctg ctaccctgcc caagctgccc cctcccattg atcagaagct cgattaccga      840
ccttctaaga aggctcttct cggccttctc gctggcaagt tcgttcgaga gaagctcggt      900
tacgtttctg ctgctcctcc cactacccct acctctgacc ttgctcaccc tgagggtcac      960
cagtactact gttaccttgt taacgttccc acttcttctg ttgcccacat taagactcag     1020
gtgcgagaga acgttcctca caagtgtact ctcactccct ttctccaggc ttgttggctt     1080
gtttctctgt tcaagtacgg tcgagttttt tctggttctt ggcttgagcg atacaccgat     1140
```

-continued

```
gttcttgttg ctatgaacac tcgacagctt ctccccgagg accttgagct tcagcgacag    1200
taccgatacg gttctaacgt tggaggtgtt cgatacaact accctattgc tccccttgac    1260
gttcgagata acgatcagaa gttctggtcc cttgttgagt cttaccgact tgccctttct    1320
gatgcccgag ataagaacga ttacctttac gctcttggtg ctcttatgct ccctgagatt    1380
tacgagaaga agaacgttga tgctgttgtt aacgatacca ttcttaacca gcgacgatct    1440
ggaaccctta tttctaacgt tggttacgtt cgagatgagc agcccactgc ttttgctatt    1500
aagaaccacg tttttttctca gggagttgga gctaaccgaa acgcttttgt tcttaacatt    1560
tgtgctaccg atcagggtgg tcttaacatc gctatttcta ttgctaaggg aacccttgct    1620
tctcgacagg agggacagga gctttgtgat attttttaagt ctactctcct tcgattttaa    1680
```

```
<210> SEQ ID NO 4
<211> LENGTH: 1680
<212> TYPE: DNA
<213> ORGANISM: Artificial Sequence
<220> FEATURE:
<223> OTHER INFORMATION: Saccharomyces LmATF1 codon optimized

<400> SEQUENCE: 4
```

```
atgggtgatt tggatgctag aggtacttct gctcatccag aattatctga aagaccatct      60
atcatgccat ccatgtccga tatccaagac ccatctggtg acgacaaggc cactccaaga     120
ggttctgctg ctggtttgcc tcaattggaa ttggctggtc acgctagaag attgggtcac     180
ttggaaaact tctttgctgt ccaacaccgt caacaaatct actcctcttt cgctgtcttc     240
tgtgaattcg acaccgcttg ttctttggct caattggctt ctgccgttag aaacgtttgt     300
ctatccaacc cattattgtt gcacaccgtc gaaccaaagc atccagatat cgctggtttc     360
taccattccg atgaatactt gtccagacca tggccacaac acgactacat gagagttttg     420
agagaagtcc acgttgctga tgtcgttatg aacggtcaaa aggaacacgc tcacgttgtc     480
agagatgctg tcgatgtctt ccaagctcac ggtaaccaag ttacctctga attgttggaa     540
ttgatgaccc aaatcgaaat ccacacgct tctcaaacta gaccatcctg gagattgttg      600
tgtttcccac acggtgaagc taacagatgg agaaccttttg cctttgtctc caaccattgt     660
tcctctgacg gtctatctgg ttttgaacttc ttccgtgact tgcaaaagga attagcccac     720
ggtccaacct ctggtgctcc aggtgcccca ggtgcttctg gtgttatctt cgactacgct     780
caagatgctg ctactttgcc aaagttgcct cctccaattg accaaaaatt ggactacaga     840
ccatccaaga aggctttgtt gggtttgttg gctggtaagt cgtcagaga aaaattgggt      900 tacgtctctg ctgctccacc aaccactcca acttctgact tggctcaccc agaaggtcac     960
caatactact gttacttggt taacgtccca acttcttctg ttgcccacat caagacccaa    1020
gttagagaaa acgtcccaca caagtgtacc ttgaccccat cttacaagc ctgttggttg     1080 gtttctttgt tcaaatacgg tcgtgtttttc tccggttcct ggttggaaag atacaccgat    1140
gttttggttg ccatgaacac cagacaatta ttaccagaag acttggaatt gcaaagacaa    1200
tacagatacg gttctaacgt cggtggtgtt cgttacaact acccaattgc tccattggac    1260
gtcagagaca acgatcaaaa gttctggtct ttagtcgaat cttacagatt ggctttgtcc    1320
gatgctcgtg acaagaacga ttatttgtac gctttgggtg ctttgatgtt gccagaaatc    1380
tacgaaaaga gaaacgttga cgctgtcgtt aatgacacca tcttgaacca agaagatct     1440 ggtactttga tttctaacgt tggttacgtt agagacgaac aaccaactgc tttcgctatc    1500
```

-continued

```
aagaaccacg tttttcagcca aggtgttggt gccaacagaa acgctttcgt cttgaacatc    1560
tgtgccactg accaaggtgg tttgaatatt gccatctcca ttgccaaggg tactttggct    1620
tccagacaag aaggtcaaga attatgtgac attttcaaat ccactctatt aagattctaa    1680
```

<210> SEQ ID NO 5
<211> LENGTH: 525
<212> TYPE: PRT
<213> ORGANISM: Saccharomyces bayanus

<400> SEQUENCE: 5

```
Met Asn Thr Tyr Ser Glu Lys Thr Ser Leu Val Gln Asp Glu Cys Leu
1               5                   10                  15

Ala Lys Met Ile Gln Asn Gly His Ser Arg Arg Met Gly Ser Val Glu
                20                  25                  30

Asp Leu Tyr Ala Ala Leu Asn Arg Gln Lys Leu Tyr Arg Asn Phe Ser
            35                  40                  45

Thr Tyr Ser Glu Leu Asn Asp Tyr Cys Thr Lys Asp Gln Leu Ala Leu
        50                  55                  60

Ala Leu Arg Asn Ile Cys Leu Lys Asn Pro Thr Leu Leu His Ile Val
65                  70                  75                  80

Leu Pro Ala Arg Trp Pro Asp His Glu Asn Tyr Tyr Leu Ser Ser Glu
                85                  90                  95

Tyr Tyr Ser Gln Pro His Pro Lys His Asp Tyr Ile Ser Val Leu Pro
                100                 105                 110

Glu Leu Lys Phe Asp Gly Val Ile Leu Asn Glu Gln Pro Glu His Asn
            115                 120                 125

Ala Leu Met Lys Gln Ile Leu Glu Glu Leu Lys Asp Ser Asn Gly Ser
        130                 135                 140

Tyr Thr Ala Lys Ile Phe Lys Leu Thr Thr Ala Leu Thr Ile Pro Tyr
145                 150                 155                 160

Ala Gly Pro Thr Ser Pro Thr Trp Arg Leu Ile Cys Leu Pro Glu Glu
                165                 170                 175

Gly Tyr Thr Asp Lys Trp Lys Lys Phe Ile Phe Leu Ser Asn His Cys
            180                 185                 190

Met Cys Asp Gly Arg Thr Ser Ile His Phe Phe Gln Asp Leu Arg Asp
        195                 200                 205

Glu Leu Asn Asn Ile Lys Thr Pro Pro Lys Lys Leu Asp Tyr Ile Phe
        210                 215                 220

Gln Tyr Glu Lys Asp Tyr Gln Leu Leu Arg Lys Leu Pro Glu Pro Ile
225                 230                 235                 240

Glu Asn Met Ile Asp Phe Arg Pro Pro Tyr Met Phe Ile Pro Lys Ser
                245                 250                 255

Leu Ile Ser Gly Phe Ile Tyr Ser His Leu Arg Phe Ser Ser Lys Gly
            260                 265                 270

Val Cys Thr Arg Met Asp Glu Leu Glu Lys Asn Asp Asp Ile Val Thr
        275                 280                 285

Glu Ile Ile Thr Ile Ser Pro Ser Glu Leu Gln Lys Ile Arg Thr Lys
        290                 295                 300

Ile Lys Ser Asn Ile Pro Gly Lys Cys Thr Ile Thr Pro Phe Leu Glu
305                 310                 315                 320

Val Cys Trp Phe Val Ser Leu His Lys Trp Gly Lys Phe Phe Lys Pro
                325                 330                 335

Leu Lys Phe Glu Trp Leu Thr Asp Val Phe Ile Pro Ala Asp Cys Arg
            340                 345                 350
```

```
Ser Leu Leu Pro Glu Asp Glu Asp Val Arg Ala Met Tyr Arg Tyr Gly
        355                 360                 365

Ala Asn Val Gly Phe Val Asp Phe Thr Pro Trp Ile Ser Glu Phe Asn
    370                 375                 380

Met Asn Asp Ser Lys Glu Asn Phe Trp Pro Leu Ile Ala His Tyr His
385                 390                 395                 400

Glu Val Ile Ser Gly Ala Ile Asn Asp Lys Lys His Leu Asn Gly Leu
                405                 410                 415

Gly Phe Asn Ile Gln Gly Leu Val Gln Lys Tyr Val Asn Ile Asp Lys
                420                 425                 430

Val Met Arg Asp Arg Ala Leu Gly Lys Ser Arg Gly Gly Thr Leu Leu
        435                 440                 445

Ser Asn Val Gly Ile Phe His Gln Ser Glu Glu Thr Asp Ser Arg Tyr
    450                 455                 460

Ser Ile Arg Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
                485                 490                 495

Val Ile Ser Ser Thr Lys Asn Ala Val Gly Ser Gln Glu Leu Leu Glu
                500                 505                 510

Glu Leu Cys Ala Met Tyr Lys Ala Leu Leu Leu Asp Pro
        515                 520                 525
```

<210> SEQ ID NO 6
<211> LENGTH: 1578
<212> TYPE: DNA
<213> ORGANISM: Artificial Sequence
<220> FEATURE:
<223> OTHER INFORMATION: Yarrowia codon optimized SbATF1

<400> SEQUENCE: 6

```
atgaacacct actctgagaa gacctctctt gttcaggacg agtgtctggc taagatgatt      60
cagaacggtc actctcgacg aatgggctct gtcgaggacc tttacgccgc cctcaaccga     120
cagaagctct accgaaactt ctctacttac tctgagctga cgattactg cactaaggat      180 cagctcgctc ttgctctccg aaacatttgt ctgaagaacc ccactctcct tcacattgtt     240
cttcccgctc gatggcccga tcacgagaac tactaccttt cttctgagta ctactctcag     300
ccccacccca agcacgatta catctctgtt cttcccgagc tgaagttcga tggtgtgatt     360
ctcaacgagc agcccgagca caacgcccct atgaagcaga ttcttgagga gcttaaggat     420
tccaacggtt cttacactgc taagattttc aagctcacta ccgctctcac tattccctac     480
gctggtccca cttctcccac ttggcgactg atttgtctgc ccgaggaggg atacaccgat     540
aagtggaaga agtttatttt cctttccaac cactgcatgt gtgatggtcg aacctctatt     600
cacttctttc aggatctccg agatgagctt aacaacatca agactccccc caagaagctc     660
gactacattt ccagtacga gaaggactac cagcttctcc gaaagctccc cgagcccatt      720
gagaacatga ttgattttcg acccccctac atgtttattc ccaagtccct tatttccggc     780
ttcatttact cccaccttcg attctcctct aagggtgtgt gtacccgaat ggacgagctt     840
gagaagaacg acgatattgt tactgagatc atcaccatct ctccctctga gcttcagaag     900
attcgaacta agatcaagtc taacattccc ggcaagtgca ccatcactcc cttccttgag     960
gtttgttggt ttgtttctct ccacaagtgg ggcaagtttt caagcccct caagttcgag    1020 tggcttaccg atgtttttat tcccgctgat tgccgatctc tgctccccga ggacgaggac   1080
```

-continued

```
gtgcgagcta tgtaccgata cggcgctaac gtcggtttg ttgacttcac tccctggatt      1140
tctgagttta acatgaacga ctctaaggag aacttctggc cccttattgc tcactaccac      1200
gaggttattt ctggtgccat caacgacaag aagcacctca acggtcttgg tttcaacatt      1260
cagggccttg tccagaagta cgtcaacatt gacaaggtga tgcgagatcg agcccttggt      1320
aagtcccgag gaggcaccct gctctctaac gtgggtattt ccaccagtc tgaggagact      1380 gactcccgat actctatccg agacctcgct ttcggtcagt ttcagggttc ttggcaccag      1440
gctttctctc tcggtgtttg ttccactaac gtgaagggaa tgaacattgt tatttcttcc      1500
actaagaacg ccgtgggttc ccaggagctc cttgaggagc tttgtgccat gtacaaggct      1560
ctgctccttg accccaa                                                      1578
```

```
<210> SEQ ID NO 7
<211> LENGTH: 515
<212> TYPE: PRT
<213> ORGANISM: Lachancea fermentati

<400> SEQUENCE: 7

Met Tyr Glu Ser Leu Gln Thr Leu Ile Glu Arg Gly His Ala Arg Arg
1               5                   10                  15

Leu Gly His Val Glu Asn Tyr Phe Val Leu Ala Gln Arg Gln Asp Leu
            20                  25                  30

Tyr Arg Val Phe Ala Tyr Tyr Gly Glu Phe Gly Glu Pro Cys Ser Leu
        35                  40                  45

Arg Gln Leu Thr Gln Ala Leu Arg Ser Met Cys Leu Gln Gln Pro Val
    50                  55                  60

Leu Leu Cys Gln Val Lys Pro Gln Glu Arg Pro Asp Leu Glu Leu Tyr
65                  70                  75                  80

Tyr Arg Ser Glu Glu Tyr Leu Ser Thr Pro Gly Gln Asp Arg Asp Tyr
                85                  90                  95

Ile Ala Leu Ala Asn Lys Val Arg Ile Ser Asp Val Leu Ile Asn Asn
            100                 105                 110

Gln Thr Glu Tyr Ala Glu Val Met His Lys Val Met Glu Glu Tyr Glu
        115                 120                 125

Ala Asn Gly His Asn Phe Thr Ser Lys Ile Phe Glu Ile Leu Ala Pro
    130                 135                 140

Ile Arg Ile Ser His Thr Asp Pro Asn Lys Leu Asn Trp Arg Leu Leu
145                 150                 155                 160

Ala Leu Pro Gly Glu Ile Pro Gly Glu Trp Asn Lys Phe Val Phe Leu
                165                 170                 175

Ser Asn His Ile Leu Lys Asp Gly Ser Ser Gly Ala His Phe Phe Ile
            180                 185                 190

Asp Leu Lys Asp Ser Leu Asn Ser Leu Pro Ser Asp Leu Gln Asp Thr
        195                 200                 205

Asp Arg Ile Phe Asp Tyr Lys Ser Asp Tyr Lys Phe Val Lys Glu Ile
    210                 215                 220

Pro Val Pro Ile Asp Glu Val Leu Asp Tyr Lys Pro Asn Leu Lys Gln
225                 230                 235                 240

Ile Ala Asn Val Phe Ser Thr Gln Leu Val Arg Glu Lys Leu Gly Tyr
                245                 250                 255

Leu Ser Pro Ala Pro Thr Ile Thr Arg Tyr Thr Asp Ala Glu Asn Asn
            260                 265                 270

Thr Asn Glu Tyr His Thr Cys Phe Ile Asn Phe Thr Pro Glu Glu Val
```

-continued

```
                275                280                285

Asp Ser Ile Lys Lys Lys Ile Lys Asp Arg Ala Gly Pro Ser Cys Thr
    290                295                300

Met Thr Pro Phe Leu Gln Ala Cys Trp Leu Val Ser Leu Tyr Lys Ser
305                310                315                320

Gly Lys Val Phe Thr Lys Ser Phe Lys Glu Trp Phe Val Asp Met Met
                325                330                335

Ile Pro Met Tyr Thr Pro Gln Met Leu Ser Asp Gly Glu Gln Thr Arg
                340                345                350

Ala Asp Tyr Arg Tyr Gly Cys Asn Val Gly Gly Thr Arg Tyr Asn Tyr
                355                360                365

Leu Ile Ser Ser Leu Asn Val Gly Asn Asn Ser Lys Lys Phe Trp Lys
    370                375                380

Leu Val Ser Tyr Tyr Asn Asp Val Phe Arg Asp Ser Lys Ala Ser Asn
385                390                395                400

Ser Tyr Leu Tyr Leu Ile Gly Met Ile Met Leu Asp Pro Ala Trp Lys
                405                410                415

Glu Lys Asn Leu Asp Ala Thr Val Leu Gln Asn Leu Leu Gly Arg His
                420                425                430

Arg Gln Gly Thr Val Leu Ser Asn Val Gly Phe Phe Ser Val Asn Gly
    435                440                445

Glu Pro Gln Asp Ala Phe His Leu Lys Asn Leu Leu Phe Thr Gln Thr
    450                455                460

Val Gly Ser Tyr Thr Phe Ala Phe Asn Leu Asn Val Cys Ser Thr Asp
465                470                475                480

Val Ala Gly Met Asn Val Gly Ala Ser Val Ser Lys Gly Thr Leu Pro
                485                490                495

Thr Arg Asn Asp Trp Glu Glu Leu Cys Glu Ile Phe Lys Thr Thr Val
                500                505                510

Leu Gln Met
        515
```

<210> SEQ ID NO 8
<211> LENGTH: 1548
<212> TYPE: DNA
<213> ORGANISM: Artificial Sequence
<220> FEATURE:
<223> OTHER INFORMATION: Yarrowia codon optimized LffATF1

<400> SEQUENCE: 8

```
atgtacgagt cccttcagac tctcatcgag cgaggacacg ctcgacgact cggccacgtg      60
gagaactact ttgttctcgc tcagcgacag gatctctacc gagttttcgc ttactacgga     120
gagttcggag agccttgctc ccttcgacac ctcactcagg ccctccgatc tatgtgtctt     180
cagcagcctg ttctgctctg ccaggtcaag ccccaggagc gacctgacct cgagctttac     240
taccgatctg aggagtacct gtctactccc ggacaggatc gagattacat cgctcttgct     300
aacaaggtgc gaatctccga tgtccttatc aacaaccaga ctgagtacgc tgaggtcatg     360
cacaaggtta tggaggagta cgaggctaac ggccacaact ttacctctaa gattttgag      420 attctcgccc ctattcgaat ctctcacacc gatcccaaca agctgaactg gcgactcctt     480
gctcttcccg agagatcccc tggtgagtgg aacaagtttg tcttcctttc caaccacatt     540
cttaaggatg ctcctctgg cgctcacttt ttcattgatc tcaaggattc tctgaactct     600
ctcccttctg acctccagga taccgaccga attttcgatt acaagtccga ctacaagttt     660
```

-continued

```
gttaaggaga tccccgtccc tatcgatgag gttcttgact acaagcctaa ccttaagcag      720
attgctaacg tcttttctac tcagcttgtt cgagagaagc tgggttacct ctctcctgct      780
cctaccatta ctcgatacac cgatgctgag aacaacacta acgagtacca cacttgcttt      840
attaacttta cccctgagga ggttgattct atcaagaaga agattaagga tcgagccggc      900
ccttcttgca ctatgacccc tttccttcag gcttgctggc tggtttccct ttacaagtcc      960
ggcaaggttt tcactaagtc tttcaaggag tggttcgtgg acatgatgat ccctatgtac     1020
accccccaga tgctctctga cggcgagcag acccgagctg actaccgata cggctgtaac     1080
gttggaggta ctcgatacaa ctacctcatc tcctctctta acgttggaaa caactccaag     1140
aagttttgga agctggtttc ttactacaac gatgtcttcc gagactctaa ggcctccaac     1200
tcttaccttt accttatcgg aatgatcatg cttgaccctg cttggaagga gaagaacctg     1260
gacgccactg tccttcagaa cctccttggt cgacaccgac agggcactgt tctgtctaac     1320
gttggattct tttctgtgaa cggagagccc caggatgctt ttcaccttaa gaaccttctc     1380
tttacccaga ctgttggttc ttacaccttt gctttcaacc tcaacgtctg ctctactgac     1440
gtggccggaa tgaacgttgg cgcttctgtg tctaagggca ccctgcccac tcgaaacgac     1500
tgggaggagc tttgcgagat cttcaagact accgttctcc agatgtaa                  1548
```

```
<210> SEQ ID NO 9
<211> LENGTH: 536
<212> TYPE: PRT
<213> ORGANISM: Lachancea fermentati

<400> SEQUENCE: 9

Met Ile Ile Ile Leu Thr Lys Pro Lys Phe Pro Ser Ser Asn Ser Arg
1               5                   10                  15

Ser Leu Glu Ile Lys Leu Asn Asn Met Pro Pro Gly Thr Leu Leu Arg
            20                  25                  30

Glu Met Ile Glu Asn Gly His Ala Arg Pro Met Gly Ser Ile Glu Asn
        35                  40                  45

Ile Tyr Gly Ile Phe Asn Arg Gln Lys Leu Tyr Arg Asn Phe Ser Met
    50                  55                  60

Phe Ala Glu Ile Asn Asp Phe Cys Asn Glu Arg Gln Leu Arg Ala Ala
65                  70                  75                  80

Leu Arg Asn Leu Cys Leu Lys Asn Pro Ile Leu Leu His Thr Ile Val
                85                  90                  95

Pro Glu Ile Trp Pro Phe Asn Glu Lys Tyr Tyr Leu Ser Asp Glu Tyr
            100                 105                 110

Tyr Cys Met Pro Arg Ser Gln His Glu Phe Ile Ala Ile Leu Pro Glu
        115                 120                 125

Leu Asp Leu Ser Asp Ile Leu Ala Asn Lys Gln Thr Gln Tyr Gln Gln
    130                 135                 140

Val Leu Glu Lys Ala Phe Arg Glu Phe Glu Ser Ser Asn Phe Cys Tyr
145                 150                 155                 160

Thr Ser Glu Val Tyr Lys Leu Ile Ala Thr Ile Ser Ile Pro Tyr Val
                165                 170                 175

Gly Pro Ser Trp Arg Leu Ile Cys Leu Pro Glu Lys Arg Gly Thr Glu
            180                 185                 190

Trp Arg Lys Phe Ile Phe Ile Ser Asn His Cys Leu Cys Asp Gly Arg
        195                 200                 205

Ser Ala Ala Asn Phe Phe His Asp Leu Lys Glu Glu Leu Asn Cys Asn
    210                 215                 220
```

-continued

```
Ile Asp Asn Arg Leu Thr Val Thr Thr Ile Phe Ser Tyr Glu Arg Asp
225                 230                 235                 240

His Tyr Leu Leu Pro Lys Leu Pro Glu Pro Leu Glu Lys Arg Ile Asp
                245                 250                 255

Phe Arg Pro Pro Trp Ser Tyr Phe Pro Lys Tyr Leu Val Trp Glu Pro
                260                 265                 270

Ile Val Asn His Phe Lys Phe Ser Ser Asn Cys Ala Thr Ser Arg Leu
                275                 280                 285

Asp Glu Ser Phe Asp Gly Lys Thr Leu Leu Thr Glu Ile Ile Asn Ile
                290                 295                 300

Asp Val Gln Val Leu Glu Lys Val Arg Gln Leu Ile Lys Ala Asn Val
305                 310                 315                 320

His Glu Gly Gly Thr Ile Thr Pro Phe Leu Glu Ile Cys Trp Leu Ile
                325                 330                 335

Ser Leu His Lys Trp Gly Ala Phe Ser Gly Lys Ser Trp Thr Lys Cys
                340                 345                 350

Leu Thr Asp Val Phe Val Pro Val Asp Val Arg Asn Leu Leu Pro Asp
                355                 360                 365

Asp Asp Asp Ile Arg Lys Ser Tyr Arg Tyr Gly Cys Asn Val Ala Ala
                370                 375                 380

Ile Glu Leu Asn Pro Trp Ile Ser Gln Leu Asp Val Glu Lys Asn Ser
385                 390                 395                 400

Asp Glu Phe Trp Ala Leu Val Ser Gln Asn Gln Asn Lys Ile Thr Ser
                405                 410                 415

Leu Leu Gln Lys Lys Glu Gln Leu Asn Leu Ile Gly Phe Asn Thr Leu
                420                 425                 430

Asp Ile Val Glu Lys Asn Phe Asn Leu Asp Arg Glu Leu Cys Val His
                435                 440                 445

Thr Leu Asn Lys Pro Arg Gln Gly Thr Leu Leu Ser Asn Leu Gly Ile
                450                 455                 460

Phe Pro Gln Asn Ser Gln Glu Arg Asp Arg Tyr Ser Leu Glu Asn Leu
465                 470                 475                 480

Ile Phe Gly Gln Phe Gln Gly Ser Phe Arg Glu Ser Phe Ser Met Cys
                485                 490                 495

Val Cys Ser Thr Asp Arg Lys Gly Met Asn Ile Val Leu Thr Thr Thr
                500                 505                 510

Ser Asp Leu Ile Pro Asn Ser Lys Ser Trp Glu Asp Leu Cys Ser Thr
                515                 520                 525

Phe Lys Ser Ile Ile Ser Asp Thr
                530                 535
```

<210> SEQ ID NO 10
<211> LENGTH: 1611
<212> TYPE: DNA
<213> ORGANISM: Artificial Sequence
<220> FEATURE:
<223> OTHER INFORMATION: Yarrowia codon optimized LfATF1

<400> SEQUENCE: 10

```
atgatcatta ttctcactaa gcctaagttc ccttcctcca actctcgatc cctggagatc      60
aagctgaaca acatgccccc tggtactctc ctgcgagaga tgatcgagaa cggacacgcc     120
cgacctatgg ctccattga gaacatttac ggaattttta accgacagaa gctctaccga     180
aactttctta tgtttgccga gatcaacgac ttttgtaacg agcgacagct tcgagccgcc     240
```

-continued

```
ctgcgaaacc tgtgtcttaa gaaccctatt ctccttcaca ccattgtccc cgagatttgg      300
cctttcaacg agaagtacta cctgtctgac gagtactact gtatgcctcg atctcagcac      360
gagtttatcg ctattctgcc cgagctcgac ctgtccgata ttctggccaa caagcagacc      420
cagtaccagc aggttctgga gaaggctttc cgagagttcg agtcctccaa cttttgttac      480
acctctgagg tgtacaagct gattgctact atttctatcc cttacgtggg ccctcttgg      540 cgacttattt gcctccctga gaagcgagga accgagtggc gaaagttcat cttcatttcc      600
aaccactgtc tctgtgatgg tcgatccgcc gccaactttt ccacgacct gaaggaggag      660 ctgaactgta acattgacaa ccgacttacc gtcactacca ttttctctta cgagcgagat      720
cactaccttc tccccaagct gcccgagccc ctggagaagc gaattgattt ccgaccccct      780
tggtcttact ttcccaagta ccttgtctgg gagcccatcg tgaaccactt caagttctcc      840
tctaactgcg ctacttcccg actcgatgag tctttcgacg gtaagactct ccttaccgag      900
attattaaca ttgacgtgca ggtccttgag aaggttcgac agctcatcaa ggccaacgtg      960
cacgagggtg gtactatcac ccctttcctt gagatttgtt ggctcatttc ccttcacaag     1020
tggggagctt tctctggtaa gtcctggact aagtgcctca ccgatgtttt tgttcccgtc     1080
gatgtccgaa accttctccc tgacgacgat gacatccgaa agtcttaccg atacggctgt     1140
aacgttgctg ctatcgagct taacccttgg atctctcagc tcgatgtcga gaagaactcc     1200
gatgagtttt gggcccttgt ttcccagaac cagaacaaga tcacctccct cctccagaag     1260
aaggagcagc tcaacctcat tggctttaac accctcgata ttgtcgagaa gaactttaac     1320
ctcgaccgag agtctgcgt ccacactctc aacaagcccc gacagggtac tctcctgtcc     1380
aacctgggta tttttccctca gaactcccag gagcgagatc gatactccct ggagaacctg     1440 attttttggtc agtttcaggg ttccttccga gagtctttct ctatgtgtgt ctgttccacc     1500
gatcgaaagg gaatgaacat tgttctcacc actacctctg atctcatccc caactccaag     1560
tcctgggagg acctttgctc taccttcaag tctattatct ccgacactta g            1611
```

<210> SEQ ID NO 11
<211> LENGTH: 476
<212> TYPE: PRT
<213> ORGANISM: Wickerhamomyces anomalus

<400> SEQUENCE: 11

```
Met Leu Glu Asn Glu Gln Leu Gln Glu Met Ile Ser Asn Gly His Ala
1               5                   10                  15

Arg Arg Met Gly His Ile Glu Asn Tyr Phe Gly Ile Ala Gln Arg Gln
            20                  25                  30

Lys Leu Tyr Lys Thr Phe Ala Val Ile Ala Lys Phe Asn Thr Lys Val
        35                  40                  45

Asn Asp Lys Ala Leu Leu Phe His Ala Leu Arg Pro Leu Leu Leu Lys
    50                  55                  60

Tyr Pro Thr Leu Ala Cys Thr Ile Val Asp Thr Asp Tyr Ser Asp Thr
65                  70                  75                  80

Thr Ile Pro Arg Pro Ile His Asp Phe Ile Lys Val Ile Asp Val Leu
                85                  90                  95

Lys Leu Lys Asp Phe Leu Tyr Glu Leu Pro Gln Glu Ile Lys Gly Leu
            100                 105                 110

Lys Gln Asp Asp Pro Glu Leu Phe Ala Lys Leu Asn Glu Ile Val Leu
        115                 120                 125

Pro Tyr Ala Asp Gly Asn Thr Leu Trp Lys Leu Ala Phe Leu Asp Asp
```

-continued

```
        130              135              140

Tyr Thr Met Val Tyr Ile Thr Asn His Cys Leu Ser Asp Gly Ile Ser
145              150              155              160

Ala Lys Asn Leu Leu Gln Asp Leu Glu Asn Glu Phe Glu Arg Leu Ser
             165              170              175

Leu Asp Asp Asp Gly Glu Asp Tyr Glu Ser Lys Ile Leu Leu Asn Tyr
             180              185              190

Asn Ser Asp Lys Ser Ile Met Glu Lys Leu Pro Pro Ser Ile Asp Ser
             195              200              205

Ile Val Ser Tyr Lys Thr Pro Trp Trp Tyr Ile Pro Glu Tyr Ile Tyr
             210              215              220

Asn Gln Phe Val Ile Asn Tyr Leu Ser Phe Ala Ser Gly Val Val Glu
225              230              235              240

Arg Ser Asp Thr His Ile Tyr Lys Gln Val His Ile Pro Pro Lys Asp
             245              250              255

Leu Glu Ile Ile Lys Gln Arg Leu Lys Asp Asn Glu Ala Asp Arg Lys
             260              265              270

Ile Thr Leu Thr Pro Phe Ile Gln Ala Ala Trp Leu Asn Ala Gln Tyr
             275              280              285

Gln Ala Gly Ile Phe Asn Asn Phe Thr Gln Val Ser Asp Val Ser Leu
             290              295              300

Pro Cys Asn Thr Arg Gln Tyr Leu Pro Ser Gly Tyr Asp Ser Asp Ala
305              310              315              320

Phe Lys Tyr Gly Ala Asn Thr Ser Gly Ser Arg Lys Phe Phe Thr Pro
             325              330              335

Val Lys Lys Leu Thr Trp Ser Ile Val Asp Tyr Phe Asn Ser Tyr Tyr
             340              345              350

Lys Tyr Leu Phe Lys Thr Lys Arg Phe Leu Tyr Asn Met Gly Ile Met
             355              360              365

Thr Leu Glu Ile Val Phe Lys Asn Gln Asn Met Asp Lys Ile Ile Ser
             370              375              380

Glu Ser Tyr Phe Gly Gln Pro Arg Gly Asn Thr Val Phe Ser Asn Ile
385              390              395              400

Gly Leu Val His Asp Ser Asn Asn Lys Lys Tyr Arg Ile Ser Asp Val
             405              410              415

His Phe Ser Gln Ser Pro Gly Ser Leu Val Phe Thr Phe Ala Met Ser
             420              425              430

Thr Val Ser Ser Val Asp Gly Gly Leu Asn Ile Val Leu Ala Met Ala
             435              440              445

Glu Lys Thr Ile Ser Lys Glu Lys Phe Glu Phe Ile Val Glu Lys Phe
             450              455              460

Thr Glu Asn Leu Leu Arg Asp Asp Ile Glu Gln Asn
465              470              475
```

```
<210> SEQ ID NO 12
<211> LENGTH: 1431
<212> TYPE: DNA
<213> ORGANISM: Artificial Sequence
<220> FEATURE:
<223> OTHER INFORMATION: Yarrowia codon optimized Wa1ATF1

<400> SEQUENCE: 12
atgctcgaga acgagcagct ccaggagatg atttccaacg gccacgcccg acgaatgggc        60
cacattgaga actactttgg catcgctcag cgacagaagc tctacaagac ctttgccgtt       120
```

-continued

```
atcgctaagt tcaacaccaa ggtgaacgac aaggctctcc tcttccacgc tctccgacct      180
ctcctgctca agtaccccac tctcgcttgt actatcgtgg acactgacta ctccgatacc      240
accatccccc gacccattca cgatttcatc aaggttattg atgttctgaa gctgaaggat      300
ttcctctacg agctccctca ggagatcaag ggcctgaagc aggatgaccc tgagctcttt      360
gccaagctga acgagattgt gctcccttac gctgatggta acactctctg gaagctcgcc      420
ttcctggacg attacaccat ggtttacatc accaaccact gtctctccga cggtatctcc      480
gctaagaacc tgctccagga tctcgagaac gagtttgagc gactgtccct cgatgacgat      540
ggtgaggatt acgagtccaa gattctcctc aactacaact ctgataagtc catcatggag      600
aagctccccc cctccatcga ttccattgtt tcctacaaga ccccctggtg gtacattccc      660
gagtacattt acaaccagtt tgtcatcaac tacctctcct tgcctccgg cgttgtggag      720 cgatccgata cccacatcta caagcaggtt cacatccccc caaggatct cgagatcatt      780 aagcagcgac tgaaggataa cgaggctgat cgaaagatta ccctgacccc tttcattcag      840
gctgcttggc tcaacgctca gtaccaggct ggtattttca caactttac ccaggtttct      900 gatgtttccc tgccctgtaa cactcgacag tacctcccct ccggatacga ttccgatgct      960
ttcaagtacg cgccaacac ttccggatct cgaaagttct tcactcccgt taagaagctc     1020
acttggtcca ttgtggacta cttcaactct tactacaagt acctcttcaa gactaagcga     1080
ttcctctaca acatgggaat tatgacccct gagattgtgt tcaagaacca gaacatggat     1140
aagatcattt ccgagtctta cttcggccag ccccgaggta acaccgtttt ttccaacatt     1200
ggtctggttc acgattccaa caacaagaag taccgaatct ccgatgttca cttctcccag     1260
tcccccggtt ctctcgtttt cacctttgcc atgtccaccg tttcctctgt tgatggtgga     1320
ctcaacattg ttcttgccat ggctgagaag accatctcca aggagaagtt tgagttcatc     1380
gttgagaagt ttaccgagaa cctcctccga gatgacatcg agcagaacta g             1431
```

```
<210> SEQ ID NO 13
<211> LENGTH: 490
<212> TYPE: PRT
<213> ORGANISM: Wickerhamomyces anomalus

<400> SEQUENCE: 13

Met Ala Gln Gln Asp Ile Tyr Lys Tyr Leu Val Asp Asn Asp Glu Lys
1               5                   10                  15

Ser Lys Lys Glu Leu Glu Thr Lys Ile Leu Asn Gly His Ala Arg Glu
            20                  25                  30

Thr Gly His Val Glu Asn Phe Phe Ala Ile Ser Gln Arg Val Asn Leu
        35                  40                  45

Tyr Lys Ser Phe Cys Val Val Thr Lys Phe Asn Lys Lys Val Ser Asn
    50                  55                  60

Asp Lys Asn Leu Leu Phe His Ala Ile Arg Pro Leu Leu Leu Lys Tyr
65                  70                  75                  80

Pro Ile Leu Ala Thr Thr Leu Val Glu Gln Lys Ile Asp Asp Ser Val
                85                  90                  95

Ile Pro Arg Pro His Asp Tyr Ile Lys Val Leu Asn Glu Ile Lys Tyr
            100                 105                 110

Lys Asp Leu Phe Ile Asp Val Asn Asp Thr Asp Leu Gln His Leu Asn
        115                 120                 125

Asp Ala Asp Leu Tyr His Ala Leu Asn Asp Ile Val Ile Pro Tyr Gly
    130                 135                 140
```

-continued

```
Lys Gly Asn Leu Thr Trp Gln Leu Val Val Ile Asp Asp Tyr Arg Leu
145                 150                 155                 160

Ala Tyr Ile Ala Asn His Ile Leu Ala Asp Ala Ile Ala Gly Lys Tyr
                165                 170                 175

Phe Phe Gln Asp Leu Glu Thr Gln Phe Ser Lys Leu Asp Pro Ser Leu
            180                 185                 190

Ile Asn Ser Gln Asn Ile Thr Asn Asp Ser Ile Ile Phe Asp Tyr Glu
            195                 200                 205

Ala Asp Lys Glu His Leu Gly Lys Leu Val Asp Ala Thr Asp Asn Ile
        210                 215                 220

Ile Asp Tyr Thr Pro Pro Tyr Trp Phe Phe Pro Glu Leu Val Met Asn
225                 230                 235                 240

Gln Phe Val Ile Ser Lys Phe Gly Ser Asn Thr Pro Pro Lys Cys Gly
                245                 250                 255

Glu Pro Ile His Tyr Lys Thr Ile His Ile Thr Ala Gln Glu Leu Ala
            260                 265                 270

Lys Met Lys Lys Asp Leu Arg Asp Asn Glu Arg Asp Lys Lys Ile Thr
            275                 280                 285

Leu Thr Pro Tyr Ile Gln Ala Ala Trp Leu Asn Ala Gln Tyr Lys Thr
        290                 295                 300

Lys Ile Phe Asn Ser Ser Ile Thr Asn Phe Ala Leu Pro Val Asp Thr
305                 310                 315                 320

Arg Ile Tyr Phe Pro Gly Asp Asp Lys Asp Lys Tyr Lys Tyr Gly Leu
                325                 330                 335

Asn Thr Ser Leu Thr Asn Lys Phe Phe Phe His Val Lys Glu Phe Thr
            340                 345                 350

Trp Gly Trp Val Asp Tyr Phe Asn Thr Tyr Ile Lys Trp Cys Leu Lys
            355                 360                 365

Thr Lys Arg Ser Leu Tyr Gln Pro Gly Leu Val Thr Leu Glu Lys Phe
        370                 375                 380

Tyr Lys Asn Lys Asn Phe Asp Val Ala Val Glu Lys Gly Gln Arg Ala
385                 390                 395                 400

Arg Leu Arg Thr Asn Thr Leu Phe Ser Asn Met Gly Leu Met Glu Ser
                405                 410                 415

Asn Asp Glu Ile Asp Gln Glu Asn Gly Ile Leu Ile Gln Asp Cys Thr
            420                 425                 430

Phe Ser Gln His Phe Asn Gly Ile Phe Tyr Asp Phe Ser Ile Asn Ala
            435                 440                 445

Ala Ala Thr Gln Arg Asn Gly Leu Asn Leu Val Ile Ser Val Pro Glu
        450                 455                 460

Ser Ala Pro Phe Thr Met Asp Gln Phe Gln Glu Val Val Asp Val Phe
465                 470                 475                 480

Lys Gln Asn Leu Leu Gly Glu Cys Val Lys
                485                 490
```

```
<210> SEQ ID NO 14
<211> LENGTH: 1473
<212> TYPE: DNA
<213> ORGANISM: Artificial Sequence
<220> FEATURE:
<223> OTHER INFORMATION: Yarrowia codon optimized Wa3ATF1

<400> SEQUENCE: 14
atggctcagc aggacattta caagtacctc gtcgacaacg acgagaagtc taagaaggag        60
ctcgagacta agatcctcaa cggacacgct cgagagactg gccacgtgga gaacttcttt       120
```

```
gccatctccc agcgagttaa cctttacaag tccttttgtg tggttaccaa gttcaacaag      180
aaggtttcca acgataagaa cctgctcttc cacgctatcc gacccctcct gctcaagtac      240
cccatcctcg ccaccactct cgtggagcag aagattgacg attccgttat ccccgacccc      300
cacgattaca ttaaggtgct caacgagatc aagtacaagg atctcttcat cgatgttaac      360
gacaccgacc tccagcacct caacgatgct gatctctacc acgccctcaa cgatattgtt      420
atcccctacg gtaagggtaa cctcacttgg cagctcgtgg ttattgacga ttaccgactc      480
gcctacatcg ccaaccacat ccttgctgat gctattgctg gcaagtactt tttccaggat      540
ctcgagactc agtttttccaa gctcgatccc tccctgatca actcccagaa catcaccaac      600
gattccatca tctttgacta cgaggctgat aaggagcacc tcggaaagct cgtcgatgcc      660
accgataaca tcattgatta cacccccccct tactggttct ccctgagct tgttatgaac      720 cagtttgtca tttccaagtt tggttccaac acccctccca agtgtggtga gcccatccac      780
tacaagacta ttcacatcac tgctcaggag ctggccaaga tgaagaagga tctccgagat      840
aacgagcgag ataagaagat caccctcact ccctacatcc aggctgcttg gctcaacgct      900
cagtacaaga ccaagatctt caactcctcc atcaccaact tcgccctccc tgttgatacc      960
cgaatttact tccctggtga tgacaaggat aagtacaagt acggcctgaa cacttccctg     1020
accaacaagt ttttcttcca cgttaaggag ttcacttggg gctgggttga ttacttcaac     1080
acttacatta agtggtgcct gaagactaag cgatccctct accagcctgg cctcgtgacc     1140
ctcgagaagt tttacaagaa caagaacttc gatgtcgctg tggagaaggg tcagcgagcc     1200
cgactgcgaa ccaacaccct cttctccaac atgggactca tggagtccaa cgatgagatt     1260
gatcaggaga acggcatcct tatccaggat tgtaccttttt cccagcactt taacggcatt     1320
ttctacgact tttccattaa cgccgccgct actcagcgaa acggactcaa cctcgtgatt     1380
tccgtccctg agtccgcccc cttcactatg gatcagttcc aggaggttgt cgacgtgttc     1440
aagcagaacc tcctcggtga gtgtgttaag taa                                   1473
```

<210> SEQ ID NO 15
<211> LENGTH: 525
<212> TYPE: PRT
<213> ORGANISM: Danio rerio

<400> SEQUENCE: 15

```
Met Leu Ser Phe Phe Trp Arg Asn Gly Ile Glu Thr Pro Glu Pro Leu
1               5                   10                  15

Lys Ala Asp Val Ser Gly Ser Ile Pro Pro Trp Leu Gln Gly Thr Leu
            20                  25                  30

Leu Arg Asn Gly Pro Gly Leu Phe Ser Val Gly Asn Thr Ser Tyr Lys
        35                  40                  45

His Trp Phe Asp Gly Met Ala Leu Ile His Ser Phe Thr Phe Lys Asp
    50                  55                  60

Gly Glu Val Phe Tyr Arg Ser Lys Tyr Leu Lys Ser Glu Thr Tyr Lys
65                  70                  75                  80

Lys Asn Ile Ala Ala Asp Arg Ile Val Val Ser Glu Phe Gly Thr Met
                85                  90                  95

Val Tyr Pro Asp Pro Cys Lys Asn Ile Phe Ser Arg Ala Phe Ser Tyr
            100                 105                 110

Met Met Asn Ala Ile Pro Asp Phe Thr Asp Asn Asn Leu Ile Asn Ile
        115                 120                 125
```

-continued

```
Ile Lys Tyr Gly Glu Asp Tyr Tyr Ala Ser Ser Glu Val Asn Tyr Ile
    130                 135                 140

Asn Gln Ile Asp Pro Leu Thr Leu Glu Thr Leu Gly Arg Thr Asn Tyr
145                 150                 155                 160

Arg Asn His Ile Ala Ile Asn Leu Ala Thr Ala His Pro His Tyr Asp
                165                 170                 175

Glu Glu Gly Asn Thr Tyr Asn Met Gly Thr Ala Ile Met Asn Leu Gly
                180                 185                 190

Arg Pro Lys Tyr Val Ile Phe Lys Val Pro Ala Asn Thr Ser Asp Lys
                195                 200                 205

Glu Asn Lys Lys Pro Ala Leu Ser Glu Val Glu Gln Val Cys Ser Ile
    210                 215                 220

Pro Ile Arg Pro Ser Leu Tyr Pro Ser Tyr Phe His Ser Phe Gly Met
225                 230                 235                 240

Thr Glu Asn Tyr Ile Ile Phe Val Glu Gln Ala Phe Lys Leu Asp Ile
                245                 250                 255

Val Lys Leu Ala Thr Ala Tyr Phe Arg Asp Ile Asn Trp Gly Ser Cys
                260                 265                 270

Leu Lys Phe Asp Gln Asp Asp Ile Asn Val Phe His Leu Val Asn Lys
                275                 280                 285

Lys Thr Gly Lys Ala Val Ser Val Lys Tyr Tyr Thr Asp Pro Phe Val
    290                 295                 300

Thr Phe His His Ile Asn Ala Tyr Glu Asp Asp Gly His Val Val Phe
305                 310                 315                 320

Asp Leu Ile Thr Tyr Lys Asp Ser Lys Leu Tyr Asp Met Phe Tyr Ile
                325                 330                 335

Gln Asn Met Lys Gln Asp Val Lys Arg Phe Ile Glu Thr Asn Lys Asp
                340                 345                 350

Phe Ala Gln Pro Val Cys Gln Arg Phe Val Leu Pro Val Asn Val Asp
                355                 360                 365

Lys Glu Thr Pro Gln Asp Ile Asn Leu Val Lys Leu Gln Asp Thr Thr
    370                 375                 380

Ala Thr Ala Val Leu Lys Glu Asp Gly Ser Val Tyr Cys Thr Pro Asp
385                 390                 395                 400

Ile Ile Phe Lys Gly Leu Glu Leu Pro Ala Ile Asn Tyr Lys Phe Asn
                405                 410                 415

Ser Lys Lys Asn Arg Tyr Phe Tyr Gly Thr Arg Val Glu Trp Ser Pro
                420                 425                 430

Tyr Pro Asn Lys Val Ala Lys Val Asp Val Val Thr Arg Thr His Lys
    435                 440                 445

Ile Trp Thr Glu Glu Glu Cys Tyr Pro Ser Glu Pro Val Phe Ile Ala
    450                 455                 460

Ser Pro Asp Ala Val Asp Glu Asp Asp Gly Val Ile Leu Ser Ser Val
465                 470                 475                 480

Val Ser Phe Asn Pro Gln Arg Pro Pro Phe Leu Val Val Leu Asp Ala
                485                 490                 495

Lys Ser Phe Lys Glu Ile Ala Arg Ala Thr Ile Asp Ala Ser Ile His
                500                 505                 510

Met Asp Leu His Gly Leu Phe Ile His Asp Lys Ser Thr
                515                 520                 525
```

<210> SEQ ID NO 16
<211> LENGTH: 1578
<212> TYPE: DNA

<213> ORGANISM: Artificial Sequence
<220> FEATURE:
<223> OTHER INFORMATION: Yarrowia codon optimized DrBCO

<400> SEQUENCE: 16

```
atgctctctt tcttctggcg aaacggtatc gagaccccg agcccctcaa ggctgacgtt      60
tccggctcta tccctccctg gcttcaggga acccttctcc gaaacggtcc tggtctgttc     120
tccgttggca acacttccta caagcactgg ttcgatggta tggctctcat tcactccttc     180
acctttaagg atggtgaggt tttttaccga tctaagtacc tgaagtctga gacttacaag     240
aagaacatcg ctgccgaccg aatcgttgtg tctgagttcg aaccatggt gtaccccgat      300 ccctgcaaga acattttctc ccgagccttc tcttacatga tgaacgccat tcctgacttt     360
accgataaca acctcattaa catcattaag tacggtgagg attactacgc ctcctctgag     420
gtcaactaca tcaaccagat tgaccccctg acccttgaga ctctcggacg aactaactac     480
cgaaaccaca ttgccatcaa ccttgccact gctcaccctc actacgacga ggagggtaac     540
acttacaaca tgggcactgc tattatgaac ctcggtcgac ccaagtacgt gattttcaag     600
gtgcccgcca cacctctga taaggagaac aagaagcctg ccctctctga ggtggagcag      660
gtttgctcca ttcccatccg accctccctt taccttctt acttccactc ttttggcatg      720
actgagaact acatcatctt cgttgagcag gccttcaagc tggacatcgt caagctggct     780
actgcttact tccgagatat taactgggga tcttgcctta agttcgacca ggatgacatt     840
aacgtgttcc acctggtcaa caagaagact ggtaaggctg tgtccgtgaa gtactacact     900
gacccctttg ttaccttcca ccacatcaac gcttacgagg acgatggcca cgtcgtcttc     960
gatctcatta cttacaagga ctctaagctg tacgatatgt ctacattca gaacatgaag     1020 caggacgtca gcgatttat tgagactaac aaggacttcg ctcagcccgt gtgccagcga     1080
tttgtccttc ccgtcaacgt tgataaggag acccctcagg acatcaacct tgtcaagctg     1140
caggacacca ctgccactgc tgtcctgaag gaggacggct ctgtctactg cacccctgac     1200
atcattttta agggtcttga gctccctgct atcaactaca agtttaactc taagaagaac     1260
cgatacttct acggcacccg agtggagtgg tcccttacc ctaacaaggt cgctaaggtg      1320
gacgttgtta ctcgaacccca caagatttgg actgaggagg agtgttaccc ttctgagcct     1380
gtctttattg cctcccctga cgccgttgat gaggatgacg gtgtgattct tcttctgtg      1440 gtttctttca accccagcg accccctttc ctggttgtcc tcgatgctaa gtccttcaag     1500
gagattgctc gagctaccat cgatgcctct attcacatgg accttcacgg ccttttcatc     1560
cacgacaagt ctacctaa                                                    1578
```

<210> SEQ ID NO 17
<211> LENGTH: 620
<212> TYPE: PRT
<213> ORGANISM: Drosophila melanogaster

<400> SEQUENCE: 17

```
Met Ala Ala Gly Val Phe Lys Ser Phe Met Arg Asp Phe Phe Ala Val
1               5                   10                  15

Lys Tyr Asp Glu Gln Arg Asn Asp Pro Gln Ala Glu Arg Leu Asp Gly
            20                  25                  30

Asn Gly Arg Leu Tyr Pro Asn Cys Ser Ser Asp Val Trp Leu Arg Ser
        35                  40                  45

Cys Glu Arg Glu Ile Val Asp Pro Ile Glu Gly His His Ser Gly His
    50                  55                  60
```

-continued

```
Ile Pro Lys Trp Ile Cys Gly Ser Leu Leu Arg Asn Gly Pro Gly Ser
65                  70                  75                  80

Trp Lys Val Gly Asp Met Thr Phe Gly His Leu Phe Asp Cys Ser Ala
                85                  90                  95

Leu Leu His Arg Phe Ala Ile Arg Asn Gly Arg Val Thr Tyr Gln Asn
            100                 105                 110

Arg Phe Val Asp Thr Glu Thr Leu Arg Lys Asn Arg Ser Ala Gln Arg
        115                 120                 125

Ile Val Val Thr Glu Phe Gly Thr Ala Ala Val Pro Asp Pro Cys His
    130                 135                 140

Ser Ile Phe Asp Arg Phe Ala Ala Ile Phe Arg Pro Asp Ser Gly Thr
145                 150                 155                 160

Asp Asn Ser Met Ile Ser Ile Tyr Pro Phe Gly Asp Gln Tyr Tyr Thr
                165                 170                 175

Phe Thr Glu Thr Pro Phe Met His Arg Ile Asn Pro Cys Thr Leu Ala
            180                 185                 190

Thr Glu Ala Arg Ile Cys Thr Thr Asp Phe Val Gly Val Val Asn His
        195                 200                 205

Thr Ser His Pro His Val Leu Pro Ser Gly Thr Val Tyr Asn Leu Gly
    210                 215                 220

Thr Thr Met Thr Arg Ser Gly Pro Ala Tyr Thr Ile Leu Ser Phe Pro
225                 230                 235                 240

His Gly Glu Gln Met Phe Glu Asp Ala His Val Val Ala Thr Leu Pro
                245                 250                 255

Cys Arg Trp Lys Leu His Pro Gly Tyr Met His Thr Phe Gly Leu Thr
            260                 265                 270

Asp His Tyr Phe Val Ile Val Glu Gln Pro Leu Ser Val Ser Leu Thr
        275                 280                 285

Glu Tyr Ile Lys Ala Gln Leu Gly Gly Gln Asn Leu Ser Ala Cys Leu
    290                 295                 300

Lys Trp Phe Glu Asp Arg Pro Thr Leu Phe His Leu Ile Asp Arg Val
305                 310                 315                 320

Ser Gly Lys Leu Val Gln Thr Tyr Glu Ser Glu Ala Phe Phe Tyr Leu
                325                 330                 335

His Ile Ile Asn Cys Phe Glu Arg Asp Gly His Val Val Val Asp Ile
            340                 345                 350

Cys Ser Tyr Arg Asn Pro Glu Met Ile Asn Cys Met Tyr Leu Glu Ala
        355                 360                 365

Ile Ala Asn Met Gln Thr Asn Pro Asn Tyr Ala Thr Leu Phe Arg Gly
    370                 375                 380

Arg Pro Leu Arg Phe Val Leu Pro Leu Gly Thr Ile Pro Pro Ala Ser
385                 390                 395                 400

Ile Ala Lys Arg Gly Leu Val Lys Ser Phe Ser Leu Ala Gly Leu Ser
                405                 410                 415

Ala Pro Gln Val Ser Arg Thr Met Lys His Ser Val Ser Gln Tyr Ala
            420                 425                 430

Asp Ile Thr Tyr Met Pro Thr Asn Gly Lys Gln Ala Thr Ala Gly Glu
        435                 440                 445

Glu Ser Pro Lys Arg Asp Ala Lys Arg Gly Arg Tyr Glu Glu Glu Asn
    450                 455                 460

Leu Val Asn Leu Val Thr Met Glu Gly Ser Gln Ala Glu Ala Phe Gln
465                 470                 475                 480
```

```
Gly Thr Asn Gly Ile Gln Leu Arg Pro Glu Met Leu Cys Asp Trp Gly
                485                 490                 495

Cys Glu Thr Pro Arg Ile Tyr Tyr Glu Arg Tyr Met Gly Lys Asn Tyr
            500                 505                 510

Arg Tyr Phe Tyr Ala Ile Ser Ser Asp Val Asp Ala Val Asn Pro Gly
        515                 520                 525

Thr Leu Ile Lys Val Asp Val Trp Asn Lys Ser Cys Leu Thr Trp Cys
    530                 535                 540

Glu Glu Asn Val Tyr Pro Ser Glu Pro Ile Phe Val Pro Ser Pro Asp
545                 550                 555                 560

Pro Lys Ser Glu Asp Asp Gly Val Ile Leu Ala Ser Met Val Leu Gly
            565                 570                 575

Gly Leu Asn Asp Arg Tyr Val Gly Leu Ile Val Leu Cys Ala Lys Thr
            580                 585                 590

Met Thr Glu Leu Gly Arg Cys Asp Phe His Thr Asn Gly Pro Val Pro
            595                 600                 605

Lys Cys Leu His Gly Trp Phe Ala Pro Asn Ala Ile
        610                 615                 620

<210> SEQ ID NO 18
<211> LENGTH: 1863
<212> TYPE: DNA
<213> ORGANISM: Artificial Sequence
<220> FEATURE:
<223> OTHER INFORMATION: Saccharomyces codon optimized DmBCO

<400> SEQUENCE: 18
atggctgctg gtgttttcaa gtctttcatg agagatttct ttgctgtcaa gtacgatgaa      60
caaagaaacg acccacaagc tgaaagattg gatggtaacg gtagattata cccaaactgt     120
tcctctgatg tctggttgag atcttgtgaa agagaaatcg tcgacccaat tgaaggtcac     180
cactctggtc acatcccaaa atggatctgt ggttctttgt tgagaaatgg tccaggttcc     240
tggaaggtcg gtgacatgac tttcggtcat ttgttcgact gttctgcttt gttgcaccgt     300
ttcgccatca gaaacggtcg tgtcacttac caaaacagat tgttgacac tgaaactttg      360 agaaagaaca gatctgctca agaattgtc gttactgaat cggtactgc tgccgttcca       420 gacccatgtc actccatttt cgacagattt gctgccatct tcagaccaga ctccggtact     480
gacaactcca tgatctccat ctacccattc ggtgaccaat actacacttt caccgaaacc     540
ccattcatgc acagaatcaa cccatgtacc ttggccactg aagctagaat ctgtaccacc     600
gatttcgttg tgttgtcaa ccacacttcc caccctcacg tcttgccatc tggtactgtt      660
tacaacttgg gtaccaccat gaccagatcc ggtccagctt acactatctt gtctttccca     720
cacggtgaac aaatgtttga agatgctcac gtcgttgcca ctttaccatg tagatggaaa     780
ttacatccag gttacatgca cactttcggt ttgactgacc attacttcgt cattgttgaa     840
caaccattgt ccgtctcctt gactgaatac atcaaggctc aattaggtgg tcaaaacttg     900
tctgcttgtt tgaaatggtt cgaagatcgt ccaactttgt tccatttgat tgacagagtt     960
tctggtaagt tggtccaaac ctacgaatct gaagctttct ctacttgca cattattaac      1020 tgtttcgaaa gagatggtca cgttgttgtt gacatctgtt cctacagaaa cccagaaatg     1080
atcaactgta tgtacttgga agctatcgcc aacatgcaaa ccaacccaa ctacgctact       1140 ttattcagag gtagaccatt gagatttgtc ttgcctctag gtaccattcc accagcttcc     1200
attgccaaga gaggtttggt taagtctttc tctttggctg gtctatctgc tccacaagtt     1260
```

-continued

```
tccagaacca tgaagcactc tgtttcccaa tacgctgaca tcacctacat gccaaccaac    1320
ggtaagcaag ctaccgctgg tgaagaatct ccaaagagag atgctaagag aggtcgttac    1380
gaagaagaaa acttggttaa cttggtcacc atggaaggtt ctcaagctga agccttccaa    1440
ggtactaacg gtattcaatt gcgtccagaa atgttgtgtg actggggttg tgaaacccca    1500
agaatttact acgaaagata catgggtaag aactaccgtt atttctacgc tatctcttct    1560
gatgtcgatg ctgtcaaccc aggtacttta atcaaggtcg atgtctggaa caaatcttgt    1620
ttgacctggt gtgaagaaaa cgtttaccca tctgaaccta tcttcgttcc atccccagac    1680
ccaaagtccg aagatgacgg tgttatcttg gcttctatgg ttttgggtgg tttgaacgac    1740
agatacgttg gtttgattgt cttgtgtgcc aagaccatga ctgaattagg tagatgtgac    1800
ttccacacca acggtcctgt tccaaagtgt ttgcacggtt ggttcgctcc aaatgcgata    1860
taa                                                                   1863
```

```
<210> SEQ ID NO 19

<400> SEQUENCE: 19

000

<210> SEQ ID NO 20
<211> LENGTH: 2364
<212> TYPE: DNA
<213> ORGANISM: Artificial Sequence
<220> FEATURE:
<223> OTHER INFORMATION: Yarrowia codon optimized UmCCO1

<400> SEQUENCE: 20
atggttaagg ctcctctaa ccgacgacag cactccgctt cccttcaggg actcccttct      60
tctcagcact gtgcccccgt tatctctatt ccttctcccc ctcccctgc tgaggatcac      120 gcttacccc cttcctcttt cactattcct ctctccaagg atgaggagct tgctgaggcc      180
ggaccctctc gacccggttc ctctgctatt tctcgacgac ctgttctgtc tcgacgacga      240
acttctaaga aggagtacgt tcaccccctac ctctccggca actttgcccc tgttaccact      300
gagtgccctc tcaccgattg tctctttgag ggtactatcc ctgaggagtt tgctggctcc      360
cagtacgtcc gaaacggcgg aaacccccctt gccaactccg agcgagatcg agatgcccac      420
tggttcgatg ctgacggtat gctggctgga gttctctttc gacgaacccc caagggcacc      480
attcagcctt gtttcctcaa ccgattcatt ctcaccgacc tcctgctctc taccccctgag      540 cactctcgac tcccttacgt cccttccatc gctactctcg tcaaccccca cacttccgtc      600
ttttggctcc tttgtgagat catccgaact ttcgttctgg ctatgcttac ctggctccct      660
ggcctcggac tcggtggcaa ccagaagctc aagcgaatct ctgttgctaa cacctccgtt      720
ttctggcacg acggaaaggc tatggctgga tgtgagtctg acccccctat gcgaatcatg      780
ctccctggtc ttgagactgc cggctggtac actggtgagg aggataagga gaaggagact      840
tgtgataaga actctggcaa ctctctcact tcttcctctt ctaagggttt tggcggaggc      900
cctcccattg tctccatgct tcgagagttt accactgctc accccaagat tgaccctcga      960
acccaggagc tccttctcta ccacatgtgc ttcgagcccc cttaccttcg aatctctgtc      1020
atccctgctt ctcagtctaa gaagactgac ctccctgctc acgctaagac cattaagggt      1080
aaggctgtgc gaggtcttaa gcagcccaag atgatgcacg atttcggcgc taccgccact      1140
cagaccgtca tcatcgacgt ccctctctcc ctcgacatga tgaacctcgt ccgaggcaag      1200
```

-continued

```
cccattctgc actacgatcc ctctcagcct acccgattcg gtattcttcc ccgatacgag    1260
cctgagcgag tgcgatggta cgagtctgcc gaggcttgct gtatctacca caccgccaac    1320
tcttgggatg acgatggcaa gtttgacgct tctcacgagc acgctacccg atccgccatc    1380
cgaggcgtca acatgctcgg ctgccgactc aactctgcca ccctcgtgta ctctgctgga    1440
aaccttctcc ctccctctca cgtccttccc cctcccaact gccctgagaa gtgtcagctc    1500
tactactggc gattcgacct tgagcacgct gagactaaca ccatttccca cgagtttgct    1560
ctgtccgaca ttcctttcga gttccccacc atcaacgagg actactctat gcagcaggct    1620
tgttacgttt acggtacttc catgcgagat ggcacctttg acgctggact cggaaaggct    1680
gctaagattg acgcccttgt taagctggac gctcaggccc ttattcgaaa gggcaaggcc    1740
atgtggtccc agggacgact taaggctgga gactctgtgg acacccgaac cgttgaggag    1800
gttctcactg ctcagcgaga tggttctgcc tcccctgagg accctatcaa gattttcgag    1860
atgccccgag gatggtacgc tcaggagact accttcgtcc ctcgacgatc ctctactaac    1920
gagacttctc aggaggatga cggttggctc gtctgctacg tgttcgatga ggccactggc    1980 cttcacccttt ccaccggaga ggttctccct ggcgcttcct ccgagctgtg gatcattgat    2040
gccaagctca tgtcccgagt cgtttgccga atcaagctcc cccagcgagt cccttacgga    2100
ctccacggca ctctctttac cgaggagcag attgcctctc agaagcctat cgacccttct    2160
caggtccgat cctgggctct gtctatcaac cttgccgatc ccttctcctc ttccgccctt    2220
ggctctaccg tgtactccgc cgctggtaag gctgccacct ccaagtttaa gaaccgagag    2280
gagacttacg ctgccttcat caaggaccct atccgaatcg gcgcttggtg ggtcaagcga    2340
aacatcgagc tcctgattgc ttaa                                           2364
```

```
<210> SEQ ID NO 21
<211> LENGTH: 325
<212> TYPE: PRT
<213> ORGANISM: Fusarium fujikuroi

<400> SEQUENCE: 21

Met Thr Thr Lys Tyr Thr Ser Val His Glu Ser Pro Asn Gly Pro Gly
1               5                   10                  15

Asp Ala Arg Pro Thr Ala Ser Gln Ile Ile Asp Asp Tyr Asn Leu Glu
            20                  25                  30

Gly Glu Leu Ser Gly Lys Thr Val Leu Val Thr Gly Cys Ser Ser Gly
        35                  40                  45

Ile Gly Val Glu Thr Ala Arg Ala Ile Tyr Arg Thr Gly Ala Thr Leu
    50                  55                  60

Tyr Leu Thr Ala Arg Asp Val Asp Lys Ala Lys Thr Val Leu Pro Asp
65                  70                  75                  80

Leu Val Asp Thr Ser Arg Val His Phe Leu His Leu Asp Leu Asn Ser
                85                  90                  95

Leu Glu Ser Val Arg Gly Phe Ala Glu Asn Phe Lys Ser Lys Ser Thr
            100                 105                 110

Gln Leu His Ile Leu Ile Glu Asn Ala Gly Val Met Ala Cys Pro Glu
        115                 120                 125

Gly Arg Thr Val Asp Gly Phe Glu Thr Gln Phe Gly Ile Asn His Leu
    130                 135                 140

Ala His Phe Leu Leu Phe Tyr Leu Leu Lys Asp Thr Leu Leu Asn Ser
145                 150                 155                 160

Ser Thr Pro Ala Phe Asn Ser Arg Val Val Ile Leu Ser Ser Cys Ala
```

-continued

```
                    165             170             175
His Gln Ala Gly Ser Val His Leu Asn Asn Leu Ser Leu Glu Gly Gly
                180             185             190

Tyr Glu Pro Trp Lys Ser Tyr Gly Gln Ser Lys Thr Ala Asn Leu Trp
            195             200             205

Thr Ala Arg Glu Ile Glu Lys Arg Phe Gly Ala Ser Gly Ile His Ser
        210             215             220

Trp Ala Val His Pro Gly Ser Ile Ala Thr Glu Leu Gln Arg His Val
    225             230             235             240

Ser Asp Glu Leu Lys Gln Lys Trp Ala Asp Asp Lys Glu Gly Ala Lys
                245             250             255

Leu Trp Lys Ser Thr Glu Gln Gly Ala Ala Thr Thr Val Leu Ala Ala
                260             265             270

Val Ser Pro Glu Leu Glu Gly Lys Gly Gly Leu Tyr Leu Glu Asp Thr
            275             280             285

Gln Val Ala Lys Pro Pro Ala Arg Gly Met Phe Gly Val Ala Asp Trp
        290             295             300

Ala Tyr Asp Glu Asp Gly Pro Ser Lys Leu Trp Ala Lys Ser Leu Glu
    305             310             315             320

Leu Leu Lys Leu Gln
                325
```

<210> SEQ ID NO 22
<211> LENGTH: 978
<212> TYPE: DNA
<213> ORGANISM: Artificial Sequence
<220> FEATURE:
<223> OTHER INFORMATION: Yarrowia codon optimized FfRDH12

<400> SEQUENCE: 22

```
atgaccacta agtacacttc cgttcacgag tctcccaacg ccctggtga cgctcgaccc       60 accgcttccc agattatcga cgattacaac cttgagggag agctttctgg caagactgtt      120
ctcgtcaccg gctgttcctc tggtattggt gttgagactg cccgagctat ttaccgaact      180
ggtgccaccc tttacctcac tgcccgagat gtcgataagg ccagaccgt tcttcccgac      240 cttgttgaca cttcccgagt ccactttctc caccttgacc ttaactctct ggagtctgtt      300
cgaggttttg ctgagaactt caagtctaag tccactcagc ttcacattct catcgagaac      360
gctggcgtga tggcctgtcc cgagggccga accgtcgatg gttttgagac tcagtttggt      420
atcaaccacc ttgctcactt tctcctcttt tacctcctca aggataccct tctcaactct      480
tctacccccg ctttcaactc ccgagttgtc atcctctctt cttgtgctca ccaggctggt      540
tccgttcacc ttaacaacct gtctcttgag ggtggatacg agccttggaa gtcttacggc      600
cagtccaaga ctgccaacct ttggactgcc cgagagatcg agaagcgatt tggtgcttcc      660
ggtatccact cttgggctgt caccccggt tccatcgcta ctgagcttca gcgacacgtt       720
tccgacgagc ttaagcagaa gtgggctgac gataaggagg tgccaagct gtggaagtcc      780 accgagcagg gtgccgccac cactgtcctt gctgctgttt cccctgagct tgagggtaag      840
ggcggtcttt accttgagga tacccaggtt gccaagcccc tgcccgagg aatgtttggt      900 gttgctgact gggcttacga tgaggatggc ccctctaagc tctgggccaa gtctcttgag      960
ctccttaagc tccagtaa                                                    978
```

<210> SEQ ID NO 23
<211> LENGTH: 299

-continued

```
<212> TYPE: PRT
<213> ORGANISM: Homo sapiens

<400> SEQUENCE: 23

Met Ala Pro Ser Ile Arg Lys Phe Phe Ala Gly Gly Val Cys Arg Thr
1               5                   10                  15

Asn Val Gln Leu Pro Gly Lys Val Val Val Ile Thr Gly Ala Asn Thr
            20                  25                  30

Gly Ile Gly Lys Glu Thr Ala Arg Glu Leu Ala Ser Arg Gly Ala Arg
        35                  40                  45

Val Tyr Ile Ala Cys Arg Asp Val Leu Lys Gly Glu Ser Ala Ala Ser
    50                  55                  60

Glu Ile Arg Val Asp Thr Lys Asn Ser Gln Val Leu Val Arg Lys Leu
65                  70                  75                  80

Asp Leu Ser Asp Thr Lys Ser Ile Arg Ala Phe Ala Glu Gly Phe Leu
                85                  90                  95

Ala Glu Glu Lys Gln Leu His Ile Leu Ile Asn Asn Ala Gly Val Met
            100                 105                 110

Met Cys Pro Tyr Ser Lys Thr Ala Asp Gly Phe Glu Thr His Leu Gly
        115                 120                 125

Val Asn His Leu Gly His Phe Leu Leu Thr Tyr Leu Leu Leu Glu Arg
    130                 135                 140

Leu Lys Val Ser Ala Pro Ala Arg Val Val Asn Val Ser Ser Val Ala
145                 150                 155                 160

His His Ile Gly Lys Ile Pro Phe His Asp Leu Gln Ser Glu Lys Arg
                165                 170                 175

Tyr Ser Arg Gly Phe Ala Tyr Cys His Ser Lys Leu Ala Asn Val Leu
                180                 185                 190

Phe Thr Arg Glu Leu Ala Lys Arg Leu Gln Gly Thr Gly Val Thr Thr
            195                 200                 205

Tyr Ala Val His Pro Gly Val Val Arg Ser Glu Leu Val Arg His Ser
    210                 215                 220

Ser Leu Leu Cys Leu Leu Trp Arg Leu Phe Ser Pro Phe Val Lys Thr
225                 230                 235                 240

Ala Arg Glu Gly Ala Gln Thr Ser Leu His Cys Ala Leu Ala Glu Gly
                245                 250                 255

Leu Glu Pro Leu Ser Gly Lys Tyr Phe Ser Asp Cys Lys Arg Thr Trp
            260                 265                 270

Val Ser Pro Arg Ala Arg Asn Asn Lys Thr Ala Glu Arg Leu Trp Asn
        275                 280                 285

Val Ser Cys Glu Leu Leu Gly Ile Arg Trp Glu
    290                 295

<210> SEQ ID NO 24
<211> LENGTH: 900
<212> TYPE: DNA
<213> ORGANISM: Artificial Sequence
<220> FEATURE:
<223> OTHER INFORMATION: Saccharomyces HsRDH12 codon optimized

<400> SEQUENCE: 24
atggctccat ctatcagaaa gttctttgct ggtggtgttt gtcgtaccaa tgtccaattg        60
ccaggtaagg ttgttgtcat cactggtgct aacactggta ttggtaagga aactgctaga       120
gaattagctt ccagaggtgc cagagtctac attgcttgtc gtgatgtctt gaagggtgaa       180
tctgctgctt ctgaaatcag agttgacacc aagaactctc aagtcttggt tagaaagttg       240
```

-continued

```
gacttgtctg acaccaaatc catcagagct ttcgctgaag gtttcttggc tgaagaaaag    300
caattgcaca tttttgatcaa caacgctggt gtcatgatgt gtccatactc caagactgct    360
gatggttttg aaacccactt gggtgtcaac catttgggtc acttcttgtt gacttacttg    420
ttgttggaaa gattgaaagt ttctgcccca gcccgtgttg tcaacgtttc ttctgttgct    480
catcacatcg gtaagattcc attccacgat ttgcaatctg aaaagcgtta ctccagaggt    540
ttcgcttact gtcactccaa attggctaac gtcttattca ccagagaatt ggccaagaga    600
ttacaaggta ctggtgttac cacttacgct gtccacccag gtgttgtcag atccgaattg    660
gttagacact cttctttgtt gtgtctatta tggagattat tctctccatt cgtcaagacc    720
gccagagaag gtgctcaaac ctctttgcac tgtgctttgg ccgaaggttt ggaacctttg    780
tccggtaagt acttctctga ctgtaagaga acctgggttt ccccaagagc tagaaacaac    840
aagactgccg aaagattatg gaacgtttcc tgtgaattgt tgggtatcag atgggagtaa    900

<210> SEQ ID NO 25

<400> SEQUENCE: 25

000

<210> SEQ ID NO 26
<211> LENGTH: 12545
<212> TYPE: DNA
<213> ORGANISM: Artificial Sequence
<220> FEATURE:
<223> OTHER INFORMATION: Cas9 hom3 plasmid 8549: Concatenation of 3
      sequences

<400> SEQUENCE: 26
ggttccgctt cctcgctcac tgactcgctg cgctcggtcg ttcggctgcg gcgagcggta     60
tcagctcact caaaggcggt aatacggtta tccacagaat cagggggataa cgcaggaaag    120 aacatgtgag caaaaggcca gcaaaaggcc aggaaccgta aaaaggccgc gttgctggcg    180 ttttttccata ggctccgccc ccctgacgag catcacaaaa atcgacgctc aagtcagagg    240
tggcgaaacc cgacaggact ataaagatac caggcgtttc ccccctggaag ctccctcgtg    300 cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaaccccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc    1020
gtgtagataa ctacgatacg ggagggctta ccatctggcc ccagtgctgc aatgataccg    1080
cgagacccac gctcaccggc tccagattta tcagcaataa accagccagc cggaagggcc    1140
```

-continued

```
gagcgcagaa gtggtcctgc aactttatcc gcctccatcc agtctattaa ttgttgccgg     1200
gaagctagag taagtagttc gccagttaat agtttgcgca acgttgttgc cattgctgca     1260
ggcatcgtgg tgtcacgctc gtcgtttggt atggcttcat tcagctccgg ttcccaacga     1320
tcaaggcgag ttacatgatc ccccatgttg tgcaaaaaag cggttagctc cttcggtcct     1380
ccgatcgttg tcagaagtaa gttggccgca gtgttatcac tcatggttat ggcagcactg     1440
cataattctc ttactgtcat gccatccgta agatgctttt ctgtgactgg tgagtactca     1500
accaagtcat tctgagaata gtgtatgcgg cgaccgagtt gctcttgccc ggcgtcaaca     1560
cgggataata ccgcgccaca tagcagaact ttaaaagtgc tcatcattgg aaaacgttct     1620
tcggggcgaa aactctcaag gatcttaccg ctgttgagat ccagttcgat gtaacccact     1680
cgtgcaccca actgatcttc agcatctttt actttcacca gcgtttctgg gtgagcaaaa     1740
acaggaaggc aaaatgccgc aaaaaaggga ataagggcga cacggaaatg ttgaatactc     1800
atactcttcc tttttcaata ttattgaagc atttatcagg gttattgtct catgagcgga     1860
tacatatttg aatgtattta gaaaaataaa caaatagggg ttccgcgcac atttccccga     1920
aaagtgccac ctgacgtcta agaaaccatt attatcatga cattaaccta taaaaatagg     1980
cgtatcacga ggccctttcg tctggcctag gaagcgactt ccaatcgctt tgcatatcca     2040
gtaccacacc cacaggcgtt tgtgctactc tactgatagc aatagatgcg tcataattgg     2100
ttggcccgct gagcctccac aggatactat tgcacatacc ctggtcatgt gcagatcagc     2160
tcatttgtgg agactctgga gtaacttaga cgacgcctgg ttcaattgcc gcaatgtgcg     2220
cccacgcaga taatgtattg aggggtggag cgcctcttgg ggacttgctg tacttgtacg     2280
ggatattaaa cgcactcagc aagaccatga cgtaaaacac acctactgta cgatacgtac     2340
tgtaggtatt gtactcgtac ccggtactac aaatagtacg atactatacg gagtgtattt     2400
gtaccttgat atacgactgg cggagtgaag agaaggagtt gaacaagacc agatggggat     2460
atcagcccca gtgctttgta ttacaagtac gagtacttaa tagatactgt aaggctattg     2520
atacggatgg cagtaagtca ttgagtaagc aattgtggcc cagcatctcc cctacgtact     2580
tgtaccatac cccatggaga caccaatggt ctttcacgca cactgtcgtg tgctgtatcg     2640
cagaatcggg tgtccaacca aatgccgtta cccccacgtc acagccgata gacagataca     2700
ccatcaatac cagcaggttg tatcatgcgg ttggctgaag gtaagctgat tggtctaaaa     2760
actgtagctg tcctaattca acgagcgcta tttggggcca accacctcgg ccaagcggcc     2820
tttaatctgc gtgccccaga ggcgtctaat gaggctctgg ccgccactgt aggagtgttt     2880
ctctgtgcgc acacgcagtt ttgagtttgg gcgactttcc cttttcccca attgcgtaca     2940
cacacagctc cgagctaagc gctgtccttg aaccttctcc ctcttttccc tcttttctc      3000 ttcccttcc cctcctccac attaaggcca aatcctgaat tgcaccaact agtacaacga      3060
caacaatgga caagaagtac tccatcggtt tggacattgg tactaactct gtcggctggg     3120
ccgtcatcac cgacgagtac aaggttccct ccaagaagtt caaggtcctt ggcaacaccg     3180
accgacactc tatcaagaag aacctgatcg gtgctctgct gttcgactct ggcgagactg     3240
ccgaggccac ccgactgaag cgaaccgctc gacgccgata cacccgacga aagaaccgaa     3300
tctgttacct ccaggagatc ttcagcaacg agatggctaa ggtcgacgac tccttcttcc     3360
accgactcga ggagtctttc ctggtcgaag aggataagaa gcacgagcga caccccatct     3420
tcggcaacat tgttgatgag gttgcctacc atgagaagta ccccaccatc taccacctcc     3480
gaaagaagct cgtcgactcc actgacaagg ctgacctccg actcatctac cttgctctcg     3540
```

-continued

```
cccacatgat caagttccga ggtcacttcc tcattgaggg tgatctcaac cccgacaact   3600
ccgacgttga caagctgttc atccagctcg tccagaccta caaccagctc tttgaggaga   3660
accctatcaa cgcttctggt gttgacgcca aggccattct ctccgcccga ctctctaagt   3720
cccgacgact cgagaacctc attgcccagc tgcccggcga aagaagaac ggcctcttcg   3780 gtaacctgat tgctctctct cttggtctga cccccaactt caagtccaac tttgacctcg   3840
ccgaggacgc caagctccag ctgtccaagg acacctacga tgacgatctg gacaacctcc   3900
tggcccagat cggtgaccag tacgccgatc tcttccttgc cgccaagaac ctctccgacg   3960
ccatcctgct ctccgacatc ctccgagtca acaccgagat taccaaggct cctctgtctg   4020
cctctatgat caagcgatac gacgagcacc accaggatct cactcttctc aaggctctcg   4080
tccgacagca gctccccgag aagtacaagg agattttctt tgaccagtcc aagaacggtt   4140
acgctggcta cattgacggt ggtgcttccc aggaagagtt ttacaagttc atcaagccta   4200
ttctggagaa gatggacggt accgaggagc tgctcgtcaa gctcaaccga gaggacctcc   4260
ttcgaaagca gcgaaccttc gataacggct ccatccccca ccagatccac ctgggtgagc   4320
tccacgccat tctccgaaga caagaggact tctacccctt cctaaaggat aaccgagaga   4380
agatcgagaa gattctcacc ttccgaatcc cctactacgt cggtcccctc gctcgaggta   4440
actcccgatt tgcttggatg acccgaaagt ccgaggagac tatcaccccc tggaactttg   4500
aagaggtagt cgacaagggt gcctccgccc agtctttcat tgagcggatg accaacttcg   4560
ataagaacct ccccaacgag aaggtccttc ccaagcactc tctcctctac gagtacttca   4620
ccgtctacaa cgagctgacc aaggtcaagt acgttaccga gggcatgcga aagcccgctt   4680
tcctctctgg tgagcagaag aaggccattg tcgacctcct gttcaagact aaccgaaaag   4740
tcaccgtcaa gcagctcaag gaagactact tcaagaagat tgagtgcttc gactccgtcg   4800
agatttccgg tgtcgaggac cgattcaacg cctccctcgg cacctaccac gatcttctga   4860
agatcatcaa ggacaaggac tttcttgata acgaggagaa cgaggacatt ctcgaggaca   4920
tcgtcctcac cctcaccctt ttcgaggatc gagagatgat cgaggagcga ctcaagacct   4980
acgcccatct cttcgacgac aaggtcatga agcaactcaa gcgacgacga tacactggct   5040
ggggccgact ttcccgaaag ctcatcaacg gcatccgaga caagcagtct ggcaagacca   5100
tcctggactt cctgaagtcc gacggtttcg ccaaccgaaa cttcatgcag ctcatccacg   5160
acgactctct taccttcaaa gaggatatcc agaaggccca ggtttctggc cagggcgact   5220
ccctccacga gcacattgcc aacctcgccg gatcccccgc catcaaaaag ggtatcctcc   5280
agaccgtcaa ggttgtcgac gaactcgtga aggtcatggg ccgacacaag cccgagaaca   5340
tcgttatcga gatggcccga gagaaccaga ccacccagaa gggtcagaag aactcccgag   5400
agcgaatgaa gcgaatcgaa gagggtatca aggagctcgg ttcccagatt ctcaaggagc   5460
accccgtcga gaacacccag ctccagaacg agaaactcta cctgtactac ctccagaatg   5520
gccgagacat gtacgttgac caggagctcg acatcaaccg actctccgac tacgacgtcg   5580
accacattgt tcctcagtcc ttcctcaagg acgactccat cgacaacaag gttctgaccc   5640
gatctgacaa gaaccgaggt aagtccgaca cgttccctc cgaagaggtc gttaagaaga   5700
tgaagaacta ctggcgacag cttctcaacg ccaaactgat cacccagcga aagtttgaca   5760
acctcaccaa ggccgagcga ggtggtctgt ccgagctgga caaggccggc ttcattaagc   5820
gacagctggt cgagactcga cagatcacca agcacgtcgc ccagatcctc gactcccgaa   5880
```

-continued

```
tgaacaccaa gtacgacgag aacgacaagc tcatccggga ggtcaaggtc atcaccctga    5940
agtctaagct tgtctccgac ttccgaaagg acttccagtt ctacaaggtc cgagagatca    6000
acaactacca ccacgcccac gacgcctacc tcaacgccgt tgttggtacc gccctcatca    6060
agaagtatcc caagctcgag tccgagttcg tttacggcga ctacaaggtt tacgatgtcc    6120
gaaagatgat tgccaagtcc gagcaggaga tcggtaaggc caccgccaag tactttttct    6180
actccaacat catgaatttc ttcaagaccg agatcactct cgccaacggt gagattcgaa    6240
agcgacccct gattgagact aatggtgaga ctggtgagat cgtctgggat aagggccgag    6300
acttcgccac cgtccgaaag gtcctgtcca tgcccaggt caacattgtc aagaagaccg     6360
aggtccagac cggtggcttc tccaaggagt ccattctccc caagcgaaac tccgacaaac    6420
tcatcgcccg taagaaggac tgggatccga agaagtacgg tggtttcgat tctcccaccg    6480
ttgcctactc cgtcctcgtt gttgctaaag tcgagaaggg taagtctaag aaactcaagt    6540
ccgtgaagga gctactcggt atcaccatca tggagcgatc ttcttttgag aagaacccca    6600
ttgacttcct cgaggccaag ggttacaaag aggtcaagaa ggacctgatt atcaagctgc    6660
ccaagtactc cctctttgag ctcgagaacg gccgaaagcg aatgctggct tccgctggtg    6720
agctgcagaa gggcaacgag ctcgctctgc cctccaagta cgtcaacttc ctctacctgg    6780
cctcccacta cgagaagctc aagggctccc ccgaggacaa cgagcagaag cagctgttcg    6840
ttgagcagca caagcactac ctcgacgaga tcatcgagca gatctccgag ttctccaagc    6900
gagtcatcct cgctgacgcc aaccttgata aggttctctc tgcttacaac aagcaccggg    6960
acaagcccat ccgagagcag gccgagaata tcatccacct cttcactctc accaacctcg    7020
gcgctcctgc tgccttcaag tacttcgaca ccaccattga ccgaaagagg tacacctcca    7080
ccaaggaagt cctcgacgcc accctgatcc accagtccat caccggcctc tacgaaaccc    7140
gaatcgacct ctcccagctc ggcggtgact ctcgagccga ccccaagaag aagcgaaaag    7200
tctaaatatc cgaagatcaa gagcgaagca agttgtaagt ccaggacatg tttcccgccc    7260
acgcgagtga tttataacac ctctcttttt tgacacccgc tcgccttgaa attcatgtca    7320
cataaattat agtcaacgac gtttgaataa cttgtcttgt agttcgatga tgatcatatg    7380
attacattaa tagtaattac tgtatttgat atatatacta attacaatag tacatattag    7440
aacatacaat agttagtgcc gtgaagtggc ttaaaatacc gcgagtcgat tacgtaatat    7500
tattacctct tgcccatcga acgtacaagt actcctctgt tctctccttc ctttgctttg    7560
tgcacgaaga actgcggtca ggtgacacaa ctttttccat ctcagggtgt gtcgcgtgtg    7620
cttcatccaa actttagttg gggttcgggt tcgcgcgaga tgatcacgtg ccctgatttg    7680
gtgtcgtccc ccgtcgcgct cgcgcacgtga tttatttatt tccggtggct gctgtctacg    7740
cggggccttc tctgcccttc tgtttcaacc ttcgggcggt tctcgtaacc agcagtagca    7800
atccatttcg aaactcaaag agctaaaaac gttaaacctc agcagtcgct cgacgaatgg    7860
gctgcggttg ggaagcccac gaggcctata gccagagcct cgagttgaca ggagcccaga    7920
cgccttttcc aacggcaact tttatataaa atggcaatgt attcatgcaa ttgcggccgt    7980
gtcaggttgg agacactgga ccacactctc cattgcttcc tgaggagatg gatcattgct    8040
agtgcatcta cgcgcagcaa tcccgcaagc tcgacaaccg tagatgggct ttggtgggcc    8100
aatcaattac gcaacccgca cgttaaattg tatgaggaag gaaggccacg gtacaaagtg    8160
ggtggtcttc acccagtggt tgttggtggc gtcatgcaga ccatgcattg gggatagcac    8220
agggttgggg tgtcttgtgg actcaatggg tgaaaggaga tggaaaaggg cggtgaaaag    8280
```

-continued

```
tggtagaatc gaaatccctg acgtcaattt ataaagtaaa atgcgtttct gccattttgc    8340
tcccctcctt ctttcgcaat cgcctcccca aaagttgtcg tggcagtaca catgcttgca    8400
tacaatgaag ctaatccggc ttgctcagta gttgctatat ccaggcatgg tgtgaaaccc    8460
ctcaaagtat atataggagc ggtgagcccc agtctggggt cttttctctc catctcaaaa    8520
ctactttctc acaatgtgtg ccctgatgag tccgtgagga cgaaacgagt aagctcgtcg    8580
gcacagtaga tgtgaagcgg ttttagagct agaaatagca agttaaaata aggctagtcc    8640
gttatcaact tgaaaaagtg gcaccgagtc ggtgcttttg gccggcatgg tcccagcctc    8700
ctcgctggcg ccggctgggc aacatgcttc ggcatggcga atgggactaa acttcgagct    8760
aatccagtag cttacgttac ccaggggcag gtcaactggc tagccacgag tctgtcccag    8820
gtcgcaattt agtgtaataa acaatatata tattgagtct aaagggaatt gtagctattg    8880
tgattgtgtg attttcgtct tgctggttct tattgtgtcc cattcgtttc atcctgatga    8940
ggacccctgg aaccggtgtt ttcttagtct ctgcaatcgc tagtcttgtt gctatgacag    9000
ttgcgtcgac actattcagg tcatctatcg gttattctga tattataata cctccggatc    9060
gatgtacctg atttatactt gcagcaatgt ttacttctta tcgatcctgg atggcggcgt    9120
tagtatcgaa tcgacagcag tatagcgacc agcattcaca tacgattgac gcatgatatt    9180
actttctgcg cacttaactt cgcatctggg cagatgatgt cgaggcgaaa aaaaatataa    9240
atcacgctaa catttgatta aaatagaaca actacaatat aaaaaaacta tacaaatgac    9300
aagttcttga aaacaagaat ctttttattg tcagtactga tttaaaagaa ctcgtcgagc    9360
atgaggtgga actggagctt gttcatgtcg gggttgtcga taccgtactt ctggaagagt    9420
cgcttctgca gagaggggga gaactcaccg agacagttcc agaggatggc cagatcctgg    9480
tatcggtcag caataccgac tcggccgaca tcaatgcagc caatgagctt accctcgtca    9540
aagatgaggt tgtcgagaga gaagtcaccg tgggtgacaa cagagtcggg ggagaagggg    9600
agcagcttgt gcatctcctt ccagacctgc tcgacgggcc agccgtttcg ctcgtcgtca    9660
aagtcggaag catcgaccag accgttgttc attcgggact gggcctgggc gagtcggaag    9720
actcggtcgg agttgaaggg gcagttgcag acggggatgg agtggagtcg tcgcaggaag    9780
acggccagag catcgacaat gttctcaccg gagtcggggt actcctcgag aacctggaag    9840
gcagtcttac cggggatggc agtggtgagg agccaggcgt cgtcggggt tcggatgaag    9900 tgcttgatgg tgggcagagg catgaactcg gtgagccagt tgagtcggac catctcgtcg    9960
gtgacgtcgt tggcaacaga gcccttaccg tgcttgagga acagctcggg agcatcgggc    10020
ttaccgtaga gtcggtagat ggtggcaccg gactggccaa cgttgtctcg ggcccacttg    10080
tagccgtaga ggtcggcgtc catgttggag ttaagtcggg gtcgggaaac gtgggtcttc    10140
tccttgccca ttgttgttta tgttcggatg tgatgtgaga actgtatcct agcaagattt    10200
taaaaggaag tatatgaaag aagaacctca gtggcaaatc ctaaccttt atatttctct    10260 acagggccgc ggcgtgggga caattcaacg cgtctgtgag gggagcgttt ccctgctcgc    10320
aggtctgcag cgaggagccg taattttttgc ttcgcgccgt gcggccatca aaatgtatgg    10380
atgcaaatga ttatacatgg ggatgtatgg gctaaatgta cgggcgacag tcacatcatg    10440
cccctgagct gcgcacgtca agactgtcaa ggagggtatt ctgggcctgg atccgaattt    10500
tcagaaccta atttatctgt taccoggcct gtggctcgca cagcttaaaa atggtcaaac    10560
tttccccttc ttgtctttttt ttcctcacat tcatcaggtt cttgtcttga tctttcaagt    10620
```

-continued

```
gagtattaat taccgacctt ggttcttcat tgggagagca ttggaagccg tggtgcagca    10680
accacaaaac ggttcttccc cttcgatacc ttcttgcctg cctttcaata caagtcggct    10740
cgattagcgg tggtcgcccc cgccagcgga gaacatggaa ctaacccaga atgagagcta    10800
agtggagaaa gaagagagtc agacgactca agcgaaagcg ccgcaaggtc cgagctcgat    10860
ccaaataagc ggtttttaac ggagatttaa cactaaatcg aagaactttt cccgtttcat    10920
ttgcgaatga gctcgttaac aaaatccccc agttttttta tccagctgta aggattgaca    10980
ttagtaatga attattgttt ggtatattta aatctgtagt tcctttctgt ccgtgtcggc    11040
aactgtcgta ctcgtgattt acttgtattg acgaatactt actgtagcgc actctgctgc    11100
tactggtcgt aaggatgtgc tatttcggtg tatggtgggt tttttggggg tcggaaccga    11160
agactgttac acgggcacgg ctcgttgtgt acacgcacag agctcttgcg agtcatgttg    11220
tagctagctc gtcgtgttca ggaactgttc gatggttcgg agagagtcgc cgcccagaac    11280
atacgcgcac cgatgtcagc agacagcctt attacaagta tattcaagca agtatatccg    11340
tagggtgcgg gtgatttgga tctaaggttc gtactcaaca ctcacgagca gcttgcctat    11400
gttacatcct tttatcagac ataacataat tggagtttac ttacacacgg ggtgtacctg    11460
tatgagcacc acctacaatt gtagcactgg tacttgtaca aagaatttat tcgtacgaat    11520
cacagggacg gccgccctca ccgaaccagc gaatacctca gcggtcccct gcagtgactc    11580
aacaaagcga tatgaacatc ttgcgatggt atcctgctga tagtttttac tgtacaaaca    11640
cctgtgtagc tccttctagc attttttaagt tattcacacc tcaggggag ggataaatta    11700 aataaattcc aaaagcgaag atcgagaaac taaattaaaa ttccaaaaac gaagttggaa    11760 cacaacccc cgaaaaaaaa caacaaacaa aaaacccaac aaaataaaca aaaacaaaat    11820
aaatatataa ctaccagtat ctgactaaaa gttcaaatac tcgtacttac aacaaataga    11880
aatgagccgg ccaaaattct gcagaaaaaa atttcaaaca agtactggta taattaaatt    11940
aaaaaacaca tcaaagtatc ataacgttag ttattttatt ttatttaata aaagaaaaca    12000
acaagatggg ctcaaaactt tcaacttata cgatacatac caaataacaa tttagtattt    12060
atctaagtgc ttttcgtaga taatggaata caaatggata tccagagtat acacatggat    12120
agtatacact gacacgacaa ttctgtatct ctttatgtta actactgtga ggcattaaat    12180
agagcttgat atataaaatg ttacatttca cagtctgaac ttttgcagat tacctaattt    12240
ggtaagatat taattatgaa ctgaaagttg atggcatccc taaatttgat gaaagatgaa    12300
attgtaaatg aggtggtaaa agagctacag tcgttttgtt ttgagatacc atcatctcta    12360
acgaaatatc tattaaaaat ctcagtgtga tcatgagtca ttgccatcct ggaaaatgtc    12420
atcatggctg atatttctaa ctgtttactt gagataaata tatatttaca agaacttccc    12480
ttgaaattaa tttagatata aaatgtttgc gggcaagtta ctacgaggaa taaattatat    12540
ctaga                                                                12545
```

```
<210> SEQ ID NO 27
<211> LENGTH: 9543
<212> TYPE: DNA
<213> ORGANISM: Artificial Sequence
<220> FEATURE:
<223> OTHER INFORMATION: expression vector

<400> SEQUENCE: 27
cctgctagcg tcgacggcca ttatggccga gccctaaatc tgtgttatac tgttgaaatg       60
tgttgattcc accaaacgac attaagaacc aactattgct tgaacttttt ttgatggctt      120
```

-continued

```
agcagatttg aactattaag aaggacttct ccagtattgt atatattgaa gaaaaccatc    180
tgaagttgca acatttgaat ttttcctatg acgttttttt ttcctcgctt catcaatatt    240
tttcagtttt ccatgttgag gccataatct gggttaactc gaattgacaa gtatatagtc    300
aagctggagg tatgaagtac gtaacattta aagagcattg agacgatatt ctgttcatga    360
taactataat tttaaatatg aagttacgct aattgcaaag tagcaaaaaa tttggacgag    420
tccggaatcg aaccggagac ctctcccatg ctaagggagc gcgctaccga ctacgccaca    480
cgcccatttc ttattgtaat ttctagtcac tgtaaaaagt gaaatcagtt taaaatgaaa    540
gtgtctatca aaacttatta tccactatca agtaattact catgactagt tttggtaccg    600
ttcgtataat gtatgctata cgaagttata agctttcgac actggatggc ggcgttagta    660
tcgaatcgac agcagtatag cgaccagcat tcacatacga ttgacgcatg atattacttt    720
ctgcgcactt aacttcgcat ctgggcagat gatgtcgagg cgaaaaaaaa tataaatcac    780
gctaacattt gattaaaata gaacaactac aatataaaaa aactatacaa atgcaaagtt    840
cttgaaaaca agaatctttt tattgtcagc atgcttattc ctttgccctc ggacgagtgc    900
tggggcgtcg gttccacta tcggcgagta cttctacaca gccatcggtc cagacggccg    960
cgcttctgcg ggcgatttgt gtacgcccga cagtcccggc tccggatcgg acgattgcgt   1020
cgcatcgacc ctgcgcccaa gctgcatcat cgaaattgcc gtcaaccaag ctctgataga   1080
gttggtcaag accaatgcgg agcatatacg cccggagccg cggcgatcct gcaagctccg   1140
gatgcctccg ctcgaagtag cgcgtctgct gctccataca agccaaccac ggcctccaga   1200
agaagatgtt ggcgacctcg tattgggaat ccccgaacat cgcctcgctc cagtcaatga   1260
ccgctgttat gcggccattg tccgtcagga cattgttgga gccgaaatcc gcgtgcacga   1320
ggtgccggac ttcggggcag tcctcggccc aaagcatcag ctcatcgaga gcctgcgcga   1380
cggacgcact gacggtgtcg tccatcacag tttgccagtg atacacatgg ggatcagcaa   1440
tcgcgcatat gaaatcacgc catgtagtgt attgaccgat tccttgcggt ccgaatgggc   1500
cgaacccgct cgtctggcta agatcggccg cagcgatggc atccattgcc tccgcgaccg   1560
gctgtagaac agcgggcagt tcggtttcag gcaggtcttg caacgtgaca ccctgtgcac   1620
ggcgggagat gcaataggtc aggctctcgc tgaactcccc aatgtcaagc acttccggaa   1680
tcgggagcgc ggccgatgca aagtgccgat aaacataacg atctttgtag aaaccatcgg   1740
cgcagctatt tacccgcagg acatatccac gccctcctac atcgaagctg aaagcacgag   1800
attcttcgcc ctccgagagc tgcatcaggt cggagacgct gtcgaacttt tcgatcagaa   1860
acttctcgac agacgtcgcg gtgagttcag gctttttacc catggttgtt tatgttcgga   1920
tgtgatgtga gaactgtatc ctagcaagat tttaaaagga agtatatgaa agaagaacct   1980
cagtggcaaa tcctaacctt ttatatttct ctacaggggc gcggcgtggg gacaattcaa   2040
cgcgtctgtg aggggagcgt ttccctgctc gcaggtttgc agcgaggagc cgtaattttt   2100
gcttcgcgcc gtgcggccat caaaatgtat ggatgcaaat gattatacat ggggatgtat   2160
gggctaaatg tacgggcgac agtcacatca tgcccctgag ctgcgcacgt caagactgtc   2220
aaggagggta ttctgggcct ccatgtcgct ggccgggtga cccggcgggg acaaggcaag   2280
ctaagcttat aacttcgtat aatgtatgct atacgaacgg taaccggtgc catttcaaag   2340
aatacgtaaa taattaatag tagtgatttt cctaacttta tttagtcaaa aaattagcct   2400
tttaattctg ctgtaacccg tacatgccca aaatagggggg cgggttacac agaatatata   2460
```

```
acatcgtagg tgtctgggtg aacagtttat tcctggcatc cactaaatat aatggagccc    2520 gcttttttaag ctggcatcca gaaaaaaaaa gaatcccagc accaaaatat tgtttttcttc    2580 accaaccatc agttcatagg tccattctct tagcgcaact acagagaaca ggggcacaaa    2640
caggcaaaaa acgggcacaa cctcaatgga gtgatgcaac ctgcctggag taaatgatga    2700
cacaaggcaa ttgacccacg catgtatcta tctcattttc ttacaccttc tattaccttc    2760
tgctctctct gatttggaaa aagctgaaaa aaaaggttga aaccagttcc ctgaaattat    2820
tcccctactt gactaataag tatataaaga cggtaggtat tgattgtaat tctgtaaatc    2880
tatttcttaa acttcttaaa ttctactttt atagttagtc tttttttttag ttttaaaaca    2940 ccaagaactt agtttcgaat aaacacacat aaggatccat ggctgccggt gtcttcaagt    3000 ctttttatgcg tgacttcttc gctgtcaaat acgacgaaca acgtaacgat ccacaagccg    3060
aacgtttgga cggtaacggt cgtttgtacc caaactgctc ctccgatgtc tggttgcgtt    3120
cctgcgaacg tgaaatcgtt gatccaatcg aaggtcacca ctccggtcac atccctaagt    3180
ggatttgcgg ttccttgttg cgtaacggtc ctggttcctg gaaggtcggt gacatgacct    3240
tcggtcactt gttcgactgc tccgccttgt tgcacagatt cgccattcgt aacggtcgtg    3300
tcacctacca aaaccgtttc gttgacaccg aaaccttgcg taagaaccgt tccgcccaac    3360
gtatcgtcgt caccgaattt ggtactgctg ctgtcccaga tccatgccac tccatcttcg    3420
atagattcgc cgctatttttc cgtccagatt ccggtactga caactccatg atttccattt    3480
atccattcgg tgaccaatac tatactttca ccgaaacccc atttatgcat agaattaacc    3540
catgcacttt ggccaccgaa gccagaatct gcaccaccga cttcgtcggt gtcgtcaacc    3600
acacttccca ccctcatgtc ttgccttccg gtactgtcta caacttgggt actaccatga    3660
ccagatctgg tccagcctac actatttttgt ccttcccaca cggtgaacaa atgttcgaag    3720
acgctcatgt cgtcgccacc ttgccatgca gatggaagtt gcacccaggt tatatgcaca    3780
ccttcggttt gaccgaccat tacttcgtta tcgtcgaaca accattgtct gtctccttga    3840
ccgaatacat taaggcccaa ttgggtggtc aaaatttgtc tgcctgtttg aagtggttcg    3900
aagaccgtcc aaccttattc cacttgattg atcgtgtctc cggtaagttg gtccaaacct    3960
acgaatccga agccttcttc tacttgcaca tcatcaactg tttcgaacgt gacggtcacg    4020
tcgtcgttga catctgttcc taccgtaacc ctgaaatgat caactgcatg tacttggaag    4080
ccatcgctaa tatgcaaacc aatccaaact atgctacctt gttccgtggt agacctttga    4140
gattcgtctt gccattgggt actatccctc cagcctccat cgccaagcgt ggtttggtca    4200
agtccttctc cttggctggt ttatccgctc cacaagtctc tcgtaccatg aagcactccg    4260
tttcccaata cgctgatatc acttacatgc ctaccaatgg taagcaagcc actgctggtg    4320
aagaatcccc aaagcgtgat gctaagcgtg tcgttacga agaagaaaac ttagtcaact    4380
tggttaccat ggaaggttcc caagccgaag ccttccaagg tactaatggt atccaattgc    4440
gtccagaaat gttgtgcgat tggggttgcg aaactcctag aatctactat gaacgttaca    4500
tgggtaagaa ctaccgttac ttctacgcca tctcttccga cgttgatgct gtcaacccag    4560
gtactttgat caaggtcgat gtctggaata agtcctgttt gacctggtgc gaagaaaacg    4620
tctacccttc cgaacctatc tttgtccctt ccctgaccc aaagtccgaa gacgacggtg    4680
tcatcttggc ctccatggtc ttgggtggtt tgaacgaccg ttacgtcggt ttgatcgttt    4740
tgtgcgctaa aaccatgacc gaattgggta gatgcgattt ccataccaat ggtcctgtcc    4800
ctaagtgctt gcatggttgg tttgctccta acgccattta agaattcgcg ggggatctcc    4860
```

```
catgtctcta ctggtggtgg tgcttctttg gaattattgg aaggtaagga attgccaggt    4920
gttgctttct tatccgaaaa gaaataaatt gaattgaatt gaaatcgtag atcaattttt    4980
ttcttttctc tttccccatc ctttacgcta aaataatagt ttattttatt ttttgaatat    5040
tttttattta tatacgtata tatagactat tatttatctt ttaatgatta ttaagatttt    5100
tattaaaaaa aaattcgctc ctctttttaat gcctttatgc agtttttttt tcccattcga    5160
tatttctatg ttcgggttca gcgtattta agtttaataa ctcgaaaatt ctgcgttcga    5220
gagctctgtc ggaagaggaa ccacctaccc tctatagtct agcatccatc ttattacata    5280
tacgatgtag aaatatgaca taaaggtaaa gattggaaag ctgccatcaa atttaatggg    5340
ggtggaacgc acgacttgat aatgcaatag gataatgagt gacaacatat aaagtggaac    5400
gagaaaccat aatattatta tgaagaatca tcgatattgt ccaaattgta ttgttatgga    5460
aatggtattc aacaactatc tcaaaagtca cctatttctc gtgctttttcg cattctatca    5520 cctgtattat tatatttcat caaaaagatg aatcatccaa tgtaaatgac acacaaatgt    5580
gcaagtgcca agctattaag tggaataatg gccttgttat ttaatggtaa gagccttctg    5640
aggccaatct gccttcacgt acacaaccac cttgttagga acaataatac caacatagtt    5700
tggccgtgat ggcctaggag gtagagggcc caattcgccc tatagtgagt cgtattacaa    5760
ttcactggcc gtcgttttac aacgtcgtga ctgggaaaac cctggcgtta cccaacttaa    5820
tcgccttgca gcacatcccc ctttcgccag ctggcgtaat agcgaagagg cccgcaccga    5880
tcgcccttcc caacagttgc gcagcctgaa tggcgaatgg acgcgccctg tagcggcgca    5940
ttaagcgcgg cgggtgtggt ggttacgcgc agcgtgaccg ctacacttgc cagcgcccta    6000
gcgcccgctc ctttcgcttt cttcccttcc tttctcgcca cgttcgccgg ctttccccgt    6060
caagctctaa atcgggggct ccctttaggg ttccgattta gtgctttacg gcacctcgac    6120
cccaaaaaac ttgattaggg tgatggttca cgtagtgggc catcgccctg atagacggtt    6180
tttcgccctt tgacgttgga gtccacgttc tttaatagtg gactcttgtt ccaaactgga    6240
acaacactca accctatctc ggtctattct tttgatttat aagggatttt gccgatttcg    6300
gcctattggt taaaaaatga gctgatttaa caaaaattta acgcgaattt taacaaaatt    6360
cagggcgcaa gggctgctaa aggaagcgga acacgtagaa agccagtccg cagaaacggt    6420
gctgaccccg gatgaatgtc agctactggg ctatctggac aagggaaaac gcaagcgcaa    6480
agagaaagca ggtagcttgc agtgggctta catggcgata gctagactgg gcggttttat    6540
ggacagcaag cgaaccggaa ttgccagctg gggcgccctc tggtaaggtt gggaagccct    6600
gcaaagtaaa ctggatggct ttcttgccgc caaggatctg atggcgcagg ggatcaagat    6660
ctgatcaaga gacaggatga ggatcgtttc gcatgattga acaagatgga ttgcacgcag    6720
gttctccggc cgcttgggtg gagaggctat tcggctatga ctgggcacaa cagacaatcg    6780
gctgctctga tgccgccgtg ttccggctgt cagcgcaggg gcgcccggtt cttttttgtca    6840 agaccgacct gtccggtgcc ctgaatgaac tgcaggacga ggcagcgcgg ctatcgtggc    6900
tggccacgac gggcgttcct tgcgcagctg tgctcgacgt tgtcactgaa gcgggaaggg    6960
actggctgct attgggcgaa gtgccggggc aggatctcct gtcatccac cttgctcctg    7020 ccgagaaagt atccatcatg gctgatgcaa tgcggcggct gcatacgctt gatccggcta    7080
cctgcccatt cgaccaccaa gcgaaacatc gcatcgagcg agcacgtact cggatggaag    7140
ccggtcttgt cgatcaggat gatctggacg aagagcatca ggggctcgcg ccagccgaac    7200
```

-continued

```
tgttcgccag gctcaaggcg cgcatgcccg acggcgagga tctcgtcgtg acccatggcg     7260
atgcctgctt gccgaatatc atggtggaaa atggccgctt ttctggattc atcgactgtg     7320
gccggctggg tgtggcggac cgctatcagg acatagcgtt ggctacccgt gatattgctg     7380
aagagcttgg cggcgaatgg gctgaccgct tcctcgtgct ttacggtatc gccgctcccg     7440
attcgcagcg catcgccttc tatcgccttc ttgacgagtt cttctgaatt gaaaaaggaa     7500
gagtatgagt attcaacatt tccgtgtcgc ccttattccc tttttttgcgg catttttgcct     7560 tcctgttttt gctcacccag aaacgctggt gaaagtaaaa gatgctgaag atcagttggg     7620
tgcacgagtg ggttacatcg aactggatct caacagcggt aagatccttg agagttttcg     7680
ccccgaagaa cgttttccaa tgatgagcac ttttaaagtt ctgctatgtg gcgcggtatt     7740
atcccgtatt gacgccgggc aagagcaact cggtcgccgc atacactatt ctcagaatga     7800
cttggttgag tactcaccag tcacagaaaa gcatcttacg gatggcatga cagtaagaga     7860
attatgcagt gctgccataa ccatgagtga taacactgcg gccaacttac ttctgacaac     7920
gatcggagga ccgaaggagc taaccgcttt tttgcacaac atgggggatc atgtaactcg     7980
ccttgatcgt tgggaaccgg agctgaatga agccatacca aacgacgagc gtgacaccac     8040
gatgcctgta gcaatggcaa caacgttgcg caaactatta actggcgaac tacttactct     8100
agcttcccgg caacaattaa tagactggat ggaggcggat aaagttgcag gaccacttct     8160
gcgctcggcc cttccggctg gctggtttat tgctgataaa tctggagccg gtgagcgtgg     8220
gtctcgcggt atcattgcag cactggggcc agatggtaag ccctcccgta tcgtagttat     8280
ctacacgacg gggagtcagg caactatgga tgaacgaaat agacagatcg ctgagatagg     8340
tgcctcactg attaagcatt ggtaactgtc agaccaagtt tactcatata ctttagat     8400 tgatttaaaa cttcattttt aatttaaaag gatctaggtg aagatccttt ttgataatct     8460
catgaccaaa atcccttaac gtgagttttc gttccactga gcgtcagacc ccgtagaaaa     8520
gatcaaagga tcttcttgag atccttttttt tctgcgcgta atctgctgct tgcaaacaaa     8580
aaaaccaccg ctaccagcgg tggtttgttt gccggatcaa gagctaccaa ctctttttcc     8640
gaaggtaact ggcttcagca gagcgcagat accaaatact gttcttctag tgtagccgta     8700
gttaggccac cacttcaaga actctgtagc accgcctaca tacctcgctc tgctaatcct     8760
gttaccagtg gctgctgcca gtggcgataa gtcgtgtctt accgggttgg actcaagacg     8820
atagttaccg gataaggcgc agcggtcggg ctgaacgggg ggttcgtgca cacagcccag     8880
cttggagcga acgacctaca ccgaactgag atacctacag cgtgagctat gagaaagcgc     8940
cacgcttccc gaagggagaa aggcggacag gtatccggta agcggcaggg tcggaacagg     9000
agagcgcacg agggagcttc caggggggaaa cgcctggtat ctttatagtc ctgtcgggtt     9060
tcgccacctc tgacttgagc gtcgattttt gtgatgctcg tcaggggggc ggagcctatg     9120
gaaaaacgcc agcaacgcgg cctttttacg gttcctggcc ttttgctggc cttttgctca     9180
catgttcttt cctgcgttat cccctgattc tgtggataac cgtattaccg cctttgagtg     9240
agctgatacc gctcgccgca gccgaacgac cgagcgcagc gagtcagtga gcgaggaagc     9300
ggaagagcgc ccaatacgca aaccgcctct ccccgcgcgt tggccgattc attaatgcag     9360
ctggcacgac aggtttcccg actggaaagc gggcagtgag cgcaacgcaa ttaatgtgag     9420
ttagctcact cattaggcac cccaggcttt acactttatg cttccggctc gtatgttgtg     9480
tggaattgtg agcggataac aatttcacac aggaaacagc tatgaccatg attacgccaa     9540
gct                                                                  9543
```

```
<210> SEQ ID NO 28
<211> LENGTH: 8580
<212> TYPE: DNA
<213> ORGANISM: Artificial Sequence
<220> FEATURE:
<223> OTHER INFORMATION: expression vector

<400> SEQUENCE: 28
cctgctagcg tcgacggcca ttatggccga gccctaaatc tgtgttatac tgttgaaatg      60
tgttgattcc accaaacgac attaagaacc aactattgct tgaacttttt ttgatggctt     120
agcagatttg aactattaag aaggacttct ccagtattgt atatattgaa gaaaaccatc     180
tgaagttgca acatttgaat ttttcctatg acgttttttt ttcctcgctt catcaatatt     240
tttcagtttt ccatgttgag gccataatct gggttaactc gaattgacaa gtatatagtc     300
aagctggagg tatgaagtac gtaacattta aagagcattg agacgatatt ctgttcatga     360
taactataat tttaaatatg aagttacgct aattgcaaag tagcaaaaaa tttggacgag     420
tccggaatcg aaccggagac ctctcccatg ctaagggagc gcgctaccga ctacgccaca     480
cgcccatttc ttattgtaat ttctagtcac tgtaaaaagt gaaatcagtt taaaatgaaa     540
gtgtctatca aaacttatta tccactatca agtaattact catgactagt tttggtaccg     600
ttcgtataat gtatgctata cgaagttata agctttcgac actggatggc ggcgttagta     660
tcgaatcgac agcagtatag cgaccagcat tcacatacga ttgacgcatg atattacttt     720
ctgcgcactt aacttcgcat ctgggcagat gatgtcgagg cgaaaaaaaa tataaatcac     780
gctaacattt gattaaaata gaacaactac aatataaaaa aactatacaa atgacaagtt     840
cttgaaaaca agaatctttt tattgtcagc atgcttattc ctttgccctc ggacgagtgc     900
tggggcgtcg gtttccacta tcggcgagta cttctacaca gccatcggtc cagacggccg     960
cgcttctgcg ggcgatttgt gtacgcccga cagtcccggc tccggatcgg acgattgcgt    1020
cgcatcgacc ctgcgcccaa gctgcatcat cgaaattgcc gtcaaccaag ctctgataga    1080
gttggtcaag accaatgcgg agcatatacg cccggagccg cggcgatcct gcaagctccg    1140
gatgcctccg ctcgaagtag cgcgtctgct gctccataca agccaccac ggcctccaga    1200 agaagatgtt ggcgacctcg tattgggaat ccccgaacat cgcctcgctc cagtcaatga    1260
ccgctgttat gcggccattg tccgtcagga cattgttgga gccgaaatcc gcgtgcacga    1320
ggtgccggac ttcggggcag tcctcggccc aaagcatcag ctcatcgaga gcctgcgcga    1380
cggacgcact gacggtgtcg tccatcacag tttgccagtg atacacatgg ggatcagcaa    1440
tcgcgcatat gaaatcacgc catgtagtgt attgaccgat tccttgcggt ccgaatgggc    1500 cgaaccgct cgtctggcta agatcggccg cagcgatggc atccattgcc tccgcgaccg    1560
gctgtagaac agcgggcagt tcggtttcag gcaggtcttg caacgtgaca ccctgtgcac    1620
ggcgggagat gcaataggtc aggctctcgc tgaactcccc aatgtcaagc acttccggaa    1680
tcgggagcgc ggccgatgca aagtgccgat aaacataacg atctttgtag aaaccatcgg    1740
cgcagctatt tacccgcagg acatatccac gccctcctac atcgaagctg aaagcacgag    1800
attcttcgcc ctccgagagc tgcatcaggt cggagacgct gtcgaacttt cgatcagaa    1860 acttctcgac agacgtcgcg gtgagttcag gctttttacc catggttgtt tatgttcgga    1920
tgtgatgtga gaactgtatc ctagcaagat tttaaaagga agtatatgaa agaagaacct    1980
cagtggcaaa tcctaacctt ttatatttct ctacagggggc gcggcgtggg gacaattcaa    2040
```

-continued

```
cgcgtctgtg aggggagcgt ttccctgctc gcaggtttgc agcgaggagc cgtaattttt    2100
gcttcgcgcc gtgcggccat caaaatgtat ggatgcaaat gattatacat ggggatgtat    2160
gggctaaatg tacgggcgac agtcacatca tgcccctgag ctgcgcacgt caagactgtc    2220
aaggagggta ttctgggcct ccatgtcgct ggccgggtga cccggcgggg acaaggcaag    2280
ctaagcttat aacttcgtat aatgtatgct atacgaacgg taaccggtgc catttcaaag    2340
aatacgtaaa taattaatag tagtgatttt cctaacttta tttagtcaaa aaattagcct    2400
tttaattctg ctgtaacccg tacatgccca aaatagggg cgggttacac agaatatata    2460
acatcgtagg tgtctgggtg aacagtttat tcctggcatc cactaaatat aatggagccc    2520 gcttttaag ctggcatcca gaaaaaaaaa gaatcccagc accaaaatat tgttttcttc    2580
accaaccatc agttcatagg tccattctct tagcgcaact acagagaaca ggggcacaaa    2640
caggcaaaaa acgggcacaa cctcaatgga gtgatgcaac ctgcctggag taaatgatga    2700
cacaaggcaa ttgacccacg catgtatcta tctcattttc ttacaccttc tattaccttc    2760
tgctctctct gatttggaaa aagctgaaaa aaaaggttga aaccagttcc ctgaaattat    2820
tcccctactt gactaataag tatataaaga cggtaggtat tgattgtaat tctgtaaatc    2880
tatttcttaa acttcttaaa ttctactttt atagttagtc ttttttttag ttttaaaaca    2940
ccaagaactt agtttcgaat aaacacacat aaggatccat ggccccatcc attcgtaagt    3000
tctttgctgg tggtgtctgt agaaccaacg tccaattgcc aggtaaggtt gtcgtcatca    3060
ctggtgccaa cactggtatc ggtaaggaaa ccgccagaga attggcctcc cgtggtgcca    3120
gagtctatat tgcctgtcgt gacgttttga agggtgaatc cgctgcttcc gaaattcgtg    3180
ttgataccaa gaactcccaa gtcttggtcc gtaagttgga cttgtccgac actaagtcta    3240
tccgtgcttt cgctgaaggt ttcttggccg aagaaaagca attgcacatc ttgattaaca    3300
acgctggtgt tatgatgtgt ccttactcta agactgctga tggtttcgaa acccacttgg    3360
gtgtcaacca cttgggtcac ttcttgttga cctacttgtt gttggaacgt ttgaaagtct    3420
ccgctccagc cagagtcgtt aacgtttcct ccgtcgccca tcacatcggt aagatcccat    3480
tccacgactt gcaatccgaa aagcgttact cccgtggttt tgcttactgc cactccaagt    3540
tggccaacgt cttgtttacc cgtgaattgg ccaagcgttt gcaaggtact ggtgtcacca    3600
cctacgccgt tcacccaggt gtcgtccgtt ccgaattggt ccgtcactcc tccttgttgt    3660
gcttgttgtg gcgtttgttc tccccattcg tcaaaaccgc cagagaaggt gcccaaacct    3720
ccttgcactg tgccttggcc gaaggtttgg aacctttgtc cggtaagtac ttctctgact    3780
gcaagcgtac ctgggtttcc cctagagcca gaaacaacaa gactgccgaa cgtttgtgga    3840
acgtttcctg cgaattgttg ggtattcgtt gggaataaga attcgcgggg gatctcccat    3900
gtctctactg gtggtggtgc ttctttggaa ttattggaag gtaaggaatt gccaggtgtt    3960 gcttttcttat ccgaaaagaa ataaattgaa ttgaattgaa atcgtagatc aattttttc    4020 ttttctcttt ccccatcctt tacgctaaaa taatagttta ttttatttt tgaatatttt    4080 ttatttatat acgtatatat agactattat ttatctttta atgattatta agatttttat    4140
taaaaaaaaa ttcgctcctc ttttaatgcc tttatgcagt ttttttttcc cattcgatat    4200
ttctatgttc gggttcagcg tatttttaagt ttaataactc gaaaattctg cgttcgagag    4260
ctctgtcgga agaggaacca cctaccctct atagtctagc atccatctta ttacatatac    4320
gatgtagaaa tatgacataa aggtaaagat tggaaagctg ccatcaaatt taatggggggt    4380 ggaacgcacg acttgataat gcaataggat aatgagtgac aacatataaa gtggaacgag    4440
```

```
aaaccataat attattatga agaatcatcg atattgtcca aattgtattg ttatggaaat    4500
ggtattcaac aactatctca aaagtcacct atttctcgtg cttttcgcat tctatcacct    4560
gtattattat atttcatcaa aaagatgaat catccaatgt aaatgacaca caaatgtgca    4620
agtgccaagc tattaagtgg aataatggcc ttgttattta atggtaagag ccttctgagg    4680
ccaatctgcc ttcacgtaca caaccacctt gttaggaaca ataataccaa catagtttgg    4740
ccgtgatggc ctaggaggta gagggcccaa ttcgccctat agtgagtcgt attacaattc    4800
actggccgtc gttttacaac gtcgtgactg ggaaaaccct ggcgttaccc aacttaatcg    4860
ccttgcagca catccccctt cgccagctg gcgtaatagc gaagaggccc gcaccgatcg    4920
cccttcccaa cagttgcgca gcctgaatgg cgaatggacg cgccctgtag cggcgcatta    4980
agcgcggcgg gtgtggtggt tacgcgcagc gtgaccgcta cacttgccag cgccctagcg    5040
cccgctcctt tcgctttctt cccttccttt ctcgccacgt tcgccggctt tccccgtcaa    5100
gctctaaatc gggggctccc tttagggttc cgatttagtg ctttacggca cctcgacccc    5160
aaaaaacttg attagggtga tggttcacgt agtgggccat cgccctgata gacggttttt    5220
cgccctttga cgttggagtc cacgttcttt aatagtggac tcttgttcca aactggaaca    5280
acactcaacc ctatctcggt ctattctttt gatttataag ggattttgcc gatttcggcc    5340
tattggttaa aaaatgagct gatttaacaa aaatttaacg cgaattttaa caaaattcag    5400
ggcgcaaggg ctgctaaagg aagcggaaca cgtagaaagc cagtccgcag aaacggtgct    5460
gacccgggat gaatgtcagc tactgggcta tctggacaag ggaaaacgca agcgcaaaga    5520
gaaagcaggt agcttgcagt gggcttacat ggcgatagct agactgggcg gttttatgga    5580
cagcaagcga accggaattg ccagctgggg cgccctctgg taaggttggg aagccctgca    5640
aagtaaactg gatggctttc ttgccgccaa ggatctgatg gcgcagggga tcaagatctg    5700
atcaagagac aggatgagga tcgtttcgca tgattgaaca agatggattg cacgcaggtt    5760
ctccggccgc ttgggtggag aggctattcg gctatgactg ggcacaacag acaatcggct    5820
gctctgatgc cgccgtgttc cggctgtcag cgcaggggcg cccggttctt tttgtcaaga    5880
ccgacctgtc cggtgccctg aatgaactgc aggacgagg agcgcggcta tcgtggctgg    5940
ccacgacggg cgttccttgc gcagctgtgc tcgacgttgt cactgaagcg ggaagggact    6000
ggctgctatt gggcgaagtg ccggggcagg atctcctgtc atcccacctt gctcctgccg    6060
agaaagtatc catcatggct gatgcaatgc ggcggctgca tacgcttgat ccggctacct    6120
gcccattcga ccaccaagcg aaacatcgca tcgagcgagc acgtactcgg atggaagccg    6180
gtcttgtcga tcaggatgat ctggacgaag agcatcaggg gctcgcgcca gccgaactgt    6240
tcgccaggct caaggcgcgc atgcccgacg gcgaggatct cgtcgtgacc catggcgatg    6300
cctgcttgcc gaatatcatg gtggaaaatg gccgcttttc tggattcatc gactgtggcc    6360
ggctgggtgt ggcggaccgc tatcaggaca tagcgttggc tacccgtgat attgctgaag    6420
agcttggcgg cgaatgggct gaccgcttcc tcgtgcttta cggtatcgcc gctcccgatt    6480
cgcagcgcat cgccttctat cgccttcttg acgagttctt ctgaattgaa aaaggaagag    6540
tatgagtatt caacatttcc gtgtcgccct tattcccttt tttgcggcat tttgccttcc    6600
tgtttttgct cacccagaaa cgctggtgaa agtaaaagat gctgaagatc agttgggtgc    6660
acgagtgggt tacatcgaac tggatctcaa cagcggtaag atccttgaga gttttcgccc    6720
cgaagaacgt tttccaatga tgagcacttt taaagttctg ctatgtggcg cggtattatc    6780
```

```
ccgtattgac gccgggcaag agcaactcgg tcgccgcata cactattctc agaatgactt    6840
ggttgagtac tcaccagtca cagaaaagca tcttacggat ggcatgacag taagagaatt    6900
atgcagtgct gccataacca tgagtgataa cactgcggcc aacttacttc tgacaacgat    6960
cggaggaccg aaggagctaa ccgctttttt gcacaacatg ggggatcatg taactcgcct    7020
tgatcgttgg gaaccggagc tgaatgaagc cataccaaac gacgagcgtg acaccacgat    7080
gcctgtagca atggcaacaa cgttgcgcaa actattaact ggcgaactac ttactctagc    7140
ttcccggcaa caattaatag actggatgga ggcggataaa gttgcaggac cacttctgcg    7200
ctcggccctt ccggctggct ggtttattgc tgataaatct ggagccggtg agcgtgggtc    7260
tcgcggtatc attgcagcac tggggccaga tggtaagccc tcccgtatcg tagttatcta    7320
cacgacgggg agtcaggcaa ctatggatga acgaaataga cagatcgctg agataggtgc    7380
ctcactgatt aagcattggt aactgtcaga ccaagtttac tcatatatac tttagattga    7440
tttaaaactt catttttaat ttaaaaggat ctaggtgaag atcctttttg ataatctcat    7500
gaccaaaatc ccttaacgtg agttttcgtt ccactgagcg tcagaccccg tagaaaagat    7560
caaaggatct tcttgagatc ctttttttct gcgcgtaatc tgctgcttgc aaacaaaaaa    7620
accaccgcta ccagcggtgg tttgtttgcc ggatcaagag ctaccaactc tttttccgaa    7680
ggtaactggc ttcagcagag cgcagatacc aaatactgtt cttctagtgt agccgtagtt    7740
aggccaccac ttcaagaact ctgtagcacc gcctacatac ctcgctctgc taatcctgtt    7800
accagtggct gctgccagtg gcgataagtc gtgtcttacc gggttggact caagacgata    7860
gttaccggat aaggcgcagc ggtcgggctg aacggggggt tcgtgcacac agcccagctt    7920
ggagcgaacg acctacaccg aactgagata cctacagcgt gagctatgag aaagcgccac    7980
gcttcccgaa gggagaaagg cggacaggta tccggtaagc ggcagggtcg aacaggaga    8040 gcgcacgagg gagcttccag ggggaaacgc ctggtatctt tatagtcctg tcgggtttcg    8100
ccacctctga cttgagcgtc gatttttgtg atgctcgtca gggggggcgga gcctatggaa    8160 aaacgccagc aacgcggcct ttttacggtt cctggccttt tgctggcctt ttgctcacat    8220
gttctttcct gcgttatccc ctgattctgt ggataaccgt attaccgcct ttgagtgagc    8280
tgataccgct cgccgcagcc gaacgaccga gcgcagcgag tcagtgagcg aggaagcgga    8340
agagcgccca atacgcaaac cgcctctccc cgcgcgttgg ccgattcatt aatgcagctg    8400
gcacgacagg tttcccgact ggaaagcggg cagtgagcgc aacgcaatta atgtgagtta    8460
gctcactcat taggcacccc aggctttaca ctttatgctt ccggctcgta tgttgtgtgg    8520
aattgtgagc ggataacaat ttcacacagg aaacagctat gaccatgatt acgccaagct    8580
```

<210> SEQ ID NO 29

<400> SEQUENCE: 29

000

<210> SEQ ID NO 30

<400> SEQUENCE: 30

000

<210> SEQ ID NO 31
<211> LENGTH: 5712
<212> TYPE: DNA
<213> ORGANISM: Artificial Sequence
<220> FEATURE:
<223> OTHER INFORMATION: expression vector

<400> SEQUENCE: 31

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatcga ctacgtcgta aggccgtttc tgacagagta aaattcttga gggaactttc     240
accattatgg gaaatggttc aagaaggtat tgacttaaac tccatcaaat ggtcaggtca     300
ttgagtgttt tttatttgtt gtattttttt tttttagag aaaatcctcc aatatcaaat      360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttttct ccttcttgat aaatgtatgt    540
agattgcgta tatagtttcg tctaccctat gaacatattc cattttgtaa tttcgtgtcg     600
tttctattat gaatttcatt tataaagttt atgtacacct aggatccgtc gacactggat     660
ggcggcgtta gtatcgaatc gacagcagta tagcgaccag cattcacata cgattgacgc     720
atgatattac tttctgcgca cttaacttcg catctgggca gatgatgtcg aggcgaaaaa     780
aaatataaat cacgctaaca tttgattaaa atagaacaac tacaatataa aaaaactata     840
caaatgacaa gttcttgaaa acaagaatct ttttattgtc agtactaggg gcagggcatg     900
ctcatgtaga gcgcctgctc gccgtccgag gcggtgccgt cgtacagggc ggtgtccagg     960
ccgcagaggg tgaaccccat ccgccggtac gcgtggatcg ccggtgcgtt gacgttggtg    1020
acctccagcc agaggtgccc ggcgccccgc tcgcgggcga actccgtcgc gagccccatc    1080
aacgcgcgcc cgacccgtg cccccggtgc tccggggcga cctcgatgtc ctcgacggtc    1140
agccggcggt tccagccgga gtacgagacg accacgaagc ccgccaggtc gccgtcgtcc    1200
ccgtacgcga cgaacgtccg ggagtccggg tcgccgtcct ccccggcgtc cgattcgtcg    1260
tccgattcgt cgtcgggaa caccttggtc aggggcgggt ccaccggcac ctcccgcagg    1320
gtgaagccgt ccccggtggc ggtgacgcgg aagacggtgt cggtggtgaa ggacccatcc    1380
agtgcctcga tggcctcggc gtcccccggg acactggtgc ggtaccggta agccgtgtcg    1440
tcaagagtgg tcattttaca tggttgttta tgttcggatg tgatgtgaga actgtatcct    1500
agcaagattt taaaaggaag tatatgaaag aagaacctca gtggcaaatc ctaaccttttt   1560 atatttctct acaggggcgc ggcgtgggga caattcaacg cgtctgtgag gggagcgttt    1620
ccctgctcgc aggtctgcag cgaggagccg taattttttgc ttcgcgccgt gcggccatca    1680
aaatgtatgt atgcaaatga ttatacatgg ggatgtatgg gctaaatgta cgggcgacag    1740
tcacatcatg cccctgagct gcgcacgtca agactgtcaa ggagggtatt ctgggcctcc    1800
atgtcgctgg ccgggtgacc cggcggggac gaggccttaa gttcgaacgt acgagctccg    1860
gcattgcgaa taccgctttc cacaaacatt gctcaaaagt atctctttgc tatatatctc    1920
tgtgctatat ccctatataa cctacccatc caccttttcgc tccttgaact tgcatctaaa   1980
ctcgacctct acattttttta tgtttatctc tagtattact ctttagacaa aaaaattgta   2040
gtaagaacta ttcatagagt gaatcgaaaa caatacgaaa atgtaaacat ttcctatacg    2100
tagtatatag agacaaaata gaagaaaccg ttcataattt tctgaccaat gaagaatcat    2160
caacgctatc actttctgtt cacaaagtat gcgcaatcca catcggtata gaatataatc    2220
```

-continued

```
ggggatgcct ttatcttgaa aaaatgcacc cgcagcttcg ctagtaatca gtaaacgcgg    2280
gaagtggagt caggcttttt ttatggaaga gaaaatagac accaaagtag ccttcttcta    2340
accttaacgg acctacagtg caaaaagtta tcaagagact gcattataga gcgcacaaag    2400
gagaaaaaaa gtaatctaag atgctttgtt agaaaaatag cgctctcggg atgcattttt    2460
gtagaacaaa aaagaagtat agattctttg ttggtaaaat agcgctctcg cgttgcattt    2520
ctgttctgta aaaatgcagc tcagattctt tgtttgaaaa attagcgctc tcgcgttgca    2580
tttttgtttt acaaaaatga agcacagatt cttcgttggt aaaatagcgc tttcgcgttg    2640
catttctgtt ctgtaaaaat gcagctcaga ttctttgttt gaaaaattag cgctctcgcg    2700
ttgcattttt gttctacaaa atgaagcaca gatgcttcgt taacaaagat atgctattga    2760
agtgcaagat ggaaacgcag aaaatgaacc ggggatgcga cgtgcaagat tacctatgca    2820
atagatgcaa tagtttctcc aggaaccgaa atacatacat tgtcttccgt aaagcgctag    2880
actatatatt attatacagg ttcaaatata ctatctgttt cagggaaaac tcccaggttc    2940
ggatgttcaa aattcaatga tgggtaacaa gtacgatcgt aaatctgtaa aacagtttgt    3000
cggatattag gctgtatctc ctcaaagcgt attcgaatat cattgagaag ctgcagcgtc    3060
acatcggata ataatgatgg cagccattgt agaagtgcct tttgcatttc tagtctcttt    3120
ctcggtctag ctagttttac tacatcgcga agatagaatc ttagatcaca ctgcctttgc    3180
tgagctggat caatagagta acaaaagagt ggtaaggcct cgttaaagga caaggacctg    3240
agcggaagtg tatcgtacag tagacggagt atactaggta tagtctatag tccgtggaat    3300
taattctcat gtttgacagc ttatcatcga taatccggag ctagcatgcg ccgctctag    3360 aactagtgga tcccccgggc tgcaggaatt cgatatcaag cttatcgata ccgtcgacct    3420
cgaggggggg cccggtaccc agcttttgtt ccctttagtg agggttaatt ccgagcttgg    3480
cgtaatcatg gtcatagctg tttcctgtgt gaaattgtta tccgctcaca attccacaca    3540
acataggagc cggaagcata aagtgtaaag cctggggtgc ctaatgagtg aggtaactca    3600
cattaattgc gttgcgctca ctgcccgctt tccagtcggg aaacctgtcg tgccagctgc    3660
attaatgaat cggccaacgc gcggggagag gcggtttgcg tattgggcgc tcttccgctt    3720
cctcgctcac tgactcgctg cgctcggtcg ttcggctgcg gcgagcggta tcagctcact    3780
caaaggcggt aatacggtta tccacagaat caggggataa cgcaggaaag aacatgtgag    3840
caaaaggcca gcaaaaggcc aggaaccgta aaaaggccgc gttgctggcg ttttttccata    3900 ggctcggccc ccctgacgag catcacaaaa atcgacgctc aagtcagagg tggcgaaacc    3960
cgacaggact ataaagatac caggcgttcc ccctggaag ctccctcgtg cgctctcctg    4020
ttccgaccct gccgcttacc ggatacctgt ccgcctttct cccttcggga agcgtggcgc    4080
tttctcaatg ctcacgctgt aggtatctca gttcggtgta ggtcgttcgc tccaagctgg    4140
gctgtgtgca cgaaccccc gttcagcccg accgctgcgc cttatccggt aactatcgtc    4200
ttgagtccaa cccggtaaga cacgacttat cgccactggc agcagccact ggtaacagga    4260
ttagcagagc gaggtatgta ggcggtgcta cagagttctt gaagtggtgg cctaactacg    4320
gctacactag aaggacagta tttggtatct gcgctctgct gaagccagtt accttcggaa    4380
aaagagttgg tagctcttga tccggcaaac aaaccaccgc tggtagcggt ggtttttttg    4440
tttgcaagca gcagattacg cgcagaaaaa aaggatctca agaagatcct ttgatctttt    4500
ctacggggtc tgacgctcag tggaacgaaa actcacgtta agggattttg gtcatgagat    4560
tatcaaaaag gatcttcacc tagatccttt taaattaaaa atgaagtttt aaatcaatct    4620
```

-continued

```
aaagtatata tgagtaaact tggtctgaca gttaccaatg cttaatcagt gaggcaccta    4680
tctcagcgat ctgtctattt cgttcatcca tagttgcctg actgcccgtc gtgtagataa    4740
ctacgatacg ggagggctta ccatctggcc ccagtgctgc aatgataccg cgagacccac    4800
gctcaccggc tccagattta tcagcaataa accagccagc cggaagggcc gagcgcagaa    4860
gtggtcctgc aactttatcc gcctccatcc agtctattaa ttgttgccgg gaagctagag    4920
taagtagttc gccagttaat agtttgcgca acgttgttgc cattgctaca ggcatcgtgg    4980
tgtcacgctc gtcgtttggt atggcttcat tcagctccgg ttcccaacga tcaaggcgag    5040
ttacatgatc ccccatgttg tgaaaaaaag cggttagctc cttcggtcct ccgatcgttg    5100
tcagaagtaa gttggccgca gtgttatcac tcatggttat ggcagcactg cataattctc    5160
ttactgtcat gccatccgta agatgctttt ctgtgactgg tgagtactca accaagtcat    5220
tctgagaata gtgtatgcgg cgaccgagtt gctcttgccc ggcgtcaata cgggataata    5280
ccgcgccaca tagcagaact ttaaaagtgc tcatcattgg aaaacgttct cggggcgaa     5340 aactctcaag gatcttaccg ctgttgagat ccagttcgat gtaacccact cgtgcaccca    5400
actgatcttc agcatctttt actttcacca gcgtttctgg gtgagcaaaa acaggaaggc    5460
aaaatgccgc aaaaaaggga ataagggcga cacggaaatg ttgaatactc atactcttcc    5520
tttttcaata ttattgaagc atttatcagg gttattgtct catgagcgga tacatatttg    5580
aatgtattta gaaaaataaa caaataggggg ttccgcgcac atttccccga aaagtgccac    5640
ctgacgtcta agaaaccatt attatcatga cattaaccta taaaaatagg cgtatcacga    5700
ggccctttcg tc                                                        5712
```

```
<210> SEQ ID NO 32
<211> LENGTH: 11742
<212> TYPE: DNA
<213> ORGANISM: Artificial Sequence
<220> FEATURE:
<223> OTHER INFORMATION: expression vector

<400> SEQUENCE: 32
```

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagt tagttctggt ccattggtga aagtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
ggcaagaata ccaagagttc ctcggtttgc cagttattaa aagactcgta tttccaaaag     840
actgcaacat actactcagt gcagcttcac agaaacctca ttcgtttatt cccttgtttg     900
```

-continued

```
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa tttttgttaa atcagctcat ttttaaccca ataggccgaa     1320
atcggcaaaa tcccttataa atcaaaagaa tagaccgaga tagggttgag tgttgttcca     1380
gtttggaaca agagtccact attaaagaac gtggactcca acgtcaaagg gcgaaaaacc     1440
gtctatcagg gcgatggccc actacgtgaa ccatcaccct aatcaagttt tttggggtcg     1500
aggtgccgta aagcactaaa tcggaaccct aaagggagcc cccgatttag agcttgacgg     1560
ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctggcgaaag ggggatgtgc tgcaaggcga     1800
ttaagttggg taacgccagg gttttcccag tcacgacgtt gtaaaacgac ggccagtgag     1860
cgcgcgtaat acgactcact ataggggcgaa ttgggtacct tttcttttttt tgcggtcacc     1920 cccatgtggc ggggaggcag aggagtaggt agagcaacga atcctactat ttatccaaat     1980
tagtctagga actcttttttc tagatttttt agatttgagg gcaagcgctg ttaacgactc     2040
agaaatgtaa gcactacgga gtagaacgag aaatccgcca taggtggaaa tcctagcaaa     2100
atcttgctta ccctagctag cctcaggtaa gctagcctta gcctgtcaaa ttttttttcaa     2160 aatttggtaa gtttctacta gcaaagcaaa cacggttcaa caaaccgaaa actccactca     2220
ttatacgtgg aaaccgaaac aaaaaaacaa aaaccaaaat actcgccaat gagaaagttg     2280
ctgcgtttct actttcgagg aagaggaact gagaggattg actacgaaag gggcaaaaac     2340
gagtcgtatt ctcccattat tgtctgctac cacgcggtct agtagaataa gcaaccagtc     2400
aacgctaaga caggtaatca aaataccagt ctgctggcta cgggctagtt tttacctctt     2460
ttagaaccca ctgtaaaagt ccgttgtaaa gcccgttctc actgttggcg ttttttttttt     2520 tttggtttag tttcttattt ttcattttttt tctttcatga ccaaaaacaa acaaatctcg     2580
cgatttgtac tgcggccact ggggcgtggc caaaaaaatg acaaatttag aaaccttagt     2640
ttctgatttt tcctgttatg aggagatatg ataaaaaata ttactgcttt attgtttttt     2700
ttttatctac tgaaatagag aaacttaccc aaggaggagg caaaaaaaag agtatatata     2760
cagcagctac cattcagatt ttaatatatt cttttctctt cttctacact attattataa     2820
taattttact atattcattt ttagcttaaa acctcataga atattattct tcagtcactc     2880
gcttaaatac ttatcaaaaa tggacaagaa atactctatt ggtttggata tcgggaccaa     2940
ctccgtcggt tgggctgtca tcaccgacga atacaaggtt ccatccaaga aattcaaggt     3000
cttgggtaac actgacagac actctatcaa gaagaatttg atcggtgctt tgttgttcga     3060
ctccggtgaa accgctgaag ctaccagatt gaagcgtacc gctcgtcgta gatacactag     3120
acgtaaaaac cgtatttgtt acttgcaaga aatctttttct aacgaaatgg ccaaggttga     3180
cgactctttc ttccacagat tggaagaatc tttcttggtt gaagaagaca gaagcacga     3240 aagacatcca atcttcggta acatcgttga cgaagttgct taccacgaaa aatacccctac     3300
```

-continued

```
catctaccat ttgagaaaga agttggtcga ttccaccgac aaggctgatt tgagattgat    3360
ctatttggcc ttggctcaca tgatcaagtt cagaggtcac ttcttgattg aaggtgactt    3420
gaacccagac aactctgacg tcgacaaatt gttcatccaa ttggtccaaa cctacaacca    3480
attattcgag gaaaacccaa ttaacgcttc tggtgttgat gctaaggcca tcttatctgc    3540
ccgtttgtcc aagtctagac gtttggaaaa cttgattgct caattgcctg gtgaaaagaa    3600
aaacggtttg ttcggtaact tgatcgcttt gtccttgggt ttgaccccaa acttcaagtc    3660
caacttcgac ttggctgaag atgccaagtt gcaattgtcc aaggacacct acgacgacga    3720
cttagacaac ttgttggctc aaatcggtga ccaatacgcc gacttgttct ggctgccaa     3780 aaacttatct gacgctatct tgttgtctga catcttgaga gttaacactg aaattaccaa    3840
ggctccattg tctgcttcta tgatcaaaag atacgacgaa caccaccaag atctgacttt    3900
gttgaaggct ttggttagac aacaattgcc agaaaagtac aaggaaatct tcttcgacca    3960
atccaaaaat ggttacgccg gttacattga cggtggtgct tctcaggaag aattctacaa    4020
gttcatcaag ccaattttgg aaaagatgga tggtactgaa gaattattgg ttaagttgaa    4080
cagagaagac ttattgagaa agcaacgtac cttcgataac ggttctatcc cacaccaaat    4140
ccacttgggt gaattgcacg ccattttgag aagacaggaa gatttctatc cattcctaaa    4200
ggacaacaga gaaaagatcg aaaagatctt aactttcaga atcccatact acgtcggtcc    4260
attggccaga ggtaattcta gattcgcttg gatgaccaga aagtctgaag aaaccatcac    4320
cccatggaac ttcgaagaag tcgtcgacaa gggtgcttct gcccaatctt tcatcgaaag    4380
aatgaccaac tttgataaga acttgccaaa cgagaaggtc ttgccaaagc actctttgtt    4440
gtacgaatac ttcaccgtct acaacgaatt aaccaaggtt aaatacgtta ctgaaggtat    4500
gagaaagcca gctttcctat ccggtgaaca aaagaaggct attgttgact tgttgtttaa    4560
gaccaacaga aaggtcactg ttaagcaatt gaaggaagac tacttcaaga agattgaatg    4620
tttcgattcc gtcgaaatct ccggtgttga agaccgtttc aatgcttctt tgggcaccta    4680
ccacgatttg ttaaagatca tcaaggacaa ggactttta gataacgaag aaaacgaaga    4740
catcttggaa gatatcgttt tgaccttgac tcttttcgag gacagagaaa tgattgaaga    4800
gagattgaag acctacgctc acttgttcga cgataaagtt atgaagcaac taaagagaag    4860
aagatacact ggttggggta gattgtccag aaagttgatt aacggtatca gagacaagca    4920
atccggtaag actattttag acttttttgaa atccgatggt ttcgctaaca gaaactttat    4980
gcaattgatt cacgacgatt ctttgacttt caaggaagac attcaaaaag cccaagtctc    5040
tggtcaaggt gattctttgc acgaacacat cgctaacttg gctggttctc cagctattaa    5100
gaagggtatc ttacaaaccg tcaaggtcgt tgatgaattg gtcaaagtca tgggtagaca    5160
caagccagaa aatattgtca tcgaaatggc tagagaaaac caaactactc aaaagggtca    5220
aaagaactct agagaacgta tgaagagaat tgaagaaggt atcaaggagt tgggttctca    5280
aattttgaaa gaacacccag tcgaaaacac tcaattacaa aacgaaaagc tatacttgta    5340
ctacttgcaa aacggtcgtg acatgtacgt cgaccaagaa ttggatatca acagattgtc    5400
tgactacgat gtcgatcata tcgtcccaca atcgttcttg aaggacgatt ccattgacaa    5460
caaagttttg actagatctg acaagaacag aggtaagtct gataacgttc catctgaaga    5520
agttgttaag aagatgaaga actactggag acaattgttg aatgctaagt tgatcactca    5580
aagaaagttc gacaacttga ccaaggctga aagaggtggt ttgtccgaat tggacaaagc    5640
```

-continued

```
cggtttcatc aagagacaat tagtcgaaac tagacaaatc accaagcatg ttgctcaaat    5700
cttggattcc agaatgaaca ctaagtacga tgaaaacgac aaaactaatta gagaagttaa    5760 ggtcatcact ttgaagtcta agttggtttc tgacttcaga aaggacttcc aattttacaa    5820
ggtcagagaa atcaacaact accatcacgc tcacgatgcc tacttgaacg ctgttgtcgg    5880
tactgcctta atcaaaaagt acccaaagtt ggaatctgaa ttcgtttacg gtgactacaa    5940
ggtttacgat gttagaaaga tgatcgccaa gtctgaacaa gaaattggta aggccactgc    6000
taagtacttc ttctactcta acatcatgaa cttttttcaag actgaaatca ctttagctaa    6060
cggtgaaatt agaaagcgtc cattgattga aaccaatggt gaaactggtg aaattgtctg    6120
ggacaagggt agagatttcg ctaccgtcag aaaggttttg tctatgccac aagttaacat    6180
cgtcaagaag actgaagttc aaactggtgg tttctctaag gaatccattt tgccaaagag    6240
aaactctgac aagttgattg ctagaaagaa ggactgggat cctaagaagt acggtggttt    6300
cgactctcca actgttgctt actccgtttt ggtcgttgct aaggttgaaa agggtaagtc    6360
taagaagttg aagtctgtta aggaattgtt gggtatcacc atcatggaaa gatcctcctt    6420
cgaaaagaac ccaatcgact tttttggaagc taagggttac aaggaagtca gaaggattt    6480 gatcattaag ttaccaaaat actccttgtt cgaattggaa aacggtagaa agagaatgtt    6540
ggcctccgct ggtgaactac aaaaaaggtaa cgaattggct ttaccatcta agtacgttaa    6600
cttcttgtac ttggcttccc actacgaaaa gttgaaaggt tccccagaag acaacgaaca    6660
aaagcaattg tttgttgaac aacacaagca ctacttggat gaaattattg aacaaatctc    6720
cgaattctcc aagagagtca ttttggctga tgctaactta gataaggttt tatccgctta    6780
caacaagcac agagacaaac caatcagaga acaagctgaa aacatcattc atttgttcac    6840
tttaaccaac ttgggtgctc cagctgcttt caaatacttc gacactacca ttgacagaaa    6900
gagatacact tccaccaaag aagtttttaga tgctactttg attcaccaat ctattaccgg    6960
tttgtacgaa accagaattg acttgtctca attgggtggt gattccagag ctgatccaaa    7020
gaagaagaga aaggtgtaaa ggagttaaag gcaaagtttt cttttctaga gccgttccca    7080
caaataatta tacgtatatg cttcttttcg tttactatat atctatattt acaagccttt    7140
attcactgat gcaatttgtt tccaaatact tttttggaga tctcataact agatatcatg    7200
atggcgcaac ttggcgctat cttaattact ctggctgcca ggcccgtgta gagggccgca    7260
agaccttctg tacgccatat agtctctaag aacttgaaca agtttctaga cctattgccg    7320
cctttcggat cgctattgtt gcggccgcca gctgaagctt cgtacgctgc aggtcgacga    7380
attctaccgt tcgtataatg tatgctatac gaagttatag atctgtttag cttgcctcgt    7440
ccccgccggg tcaccggcc agcgacatgg aggcccagaa taccctcctt gacagtcttg    7500
acgtgcgcag ctcaggggca tgatgtgact gtcgcccgta catttagccc atacatcccc    7560
atgtataatc atttgcatcc atacatttg atggccgcac ggcgcgaagc aaaaattacg    7620
gctcctcgct gcagacctgc gagcaggaa acgctcccct cacagacgcg ttgaattgtc    7680
cccacgccgc gcccctgtag agaaatataa aaggttagga tttgccactg aggttcttct    7740
ttcatatact tccttttaaa atcttgctag gatacagttc tcacatcaca tccgaacata    7800
aacaaccatg ggtaaggaaa agactcacgt ttcgaggccg cgattaaatt ccaacatgga    7860
tgctgattta tatgggtata aatgggctcg cgataatgtc gggcaatcag gtgcgacaat    7920
ctatcgatty tatgggaagc ccgatgcgcc agagttgttt ctgaaacatg gcaaaggtag    7980
cgttgccaat gatgttacag atgagatggt cagactaaac tggctgacgg aatttatgcc    8040
```

-continued

```
tcttccgacc atcaagcatt ttatccgtac tcctgatgat gcatggttac tcaccactgc      8100
gatccccggc aaaacagcat tccaggtatt agaagaatat cctgattcag gtgaaaatat      8160
tgttgatgcg ctggcagtgt tcctgcgccg gttgcattcg attcctgttt gtaattgtcc      8220
ttttaacagc gatcgcgtat ttcgtctcgc tcaggcgcaa tcacgaatga ataacggttt      8280
ggttgatgcg agtgattttg atgacgagcg taatggctgg cctgttgaac aagtctggaa      8340
agaaatgcat aagcttttgc cattctcacc ggattcagtc gtcactcatg gtgatttctc      8400
acttgataac cttatttttg acgaggggaa attaataggt tgtattgatg ttggacgagt      8460
cggaatcgca gaccgatacc aggatcttgc catcctatgg aactgcctcg gtgagttttc      8520
tccttcatta cagaaacggc ttttttcaaaa atatggtatt gataatcctg atatgaataa      8580
attgcagttt catttgatgc tcgatgagtt tttctaatca gtactgacaa taaaaagatt      8640 cttgtttttca agaacttgtc atttgtatag ttttttttata ttgtagttgt tctattttaa      8700
tcaaatgtta gcgtgattta tatttttttt cgcctcgaca tcatctgccc agatgcgaag      8760
ttaagtgcgc agaaagtaat atcatgcgtc aatcgtatgt gaatgctggt cgctatactg      8820
ctgtcgattc gatactaacg ccgccatcca gtgtcgaaaa cgagctcata acttcgtata      8880
atgtatgcta tacgaacggt agaattcgaa tcagatccac tagtggccta tgcggccgcc      8940
accgcggtgg agctccagct tttgttccct ttagtgaggg ttaattgcgc gcttggcgta      9000
atcatggtca tagctgtttc ctgtgtgaaa ttgttatccg ctcacaattc cacacaacat      9060
aggagccgga agcataaagt gtaaagcctg gggtgcctaa tgagtgaggt aactcacatt      9120
aattgcgttg cgctcactgc ccgctttcca gtcgggaaac ctgtcgtgcc agctgcatta      9180
atgaatcggc caacgcgcgg ggagaggcgg tttgcgtatt gggcgctctt ccgcttcctc      9240
gctcactgac tcgctgcgct cggtcgttcg gctgcggcga gcggtatcag ctcactcaaa      9300
ggcggtaata cggttatcca cagaatcagg ggataacgca ggaaagaaca tgtgagcaaa      9360
aggccagcaa aaggccagga accgtaaaaa ggccgcgttg ctggcgtttt tccataggct      9420
ccgcccccct gacgagcatc acaaaaatcg acgctcaagt cagaggtggc gaaacccgac      9480
aggactataa agataccagg cgtttccccc tggaagctcc ctcgtgcgct ctcctgttcc      9540
gaccctgccg cttaccggat acctgtccgc ctttctccct tcgggaagcg tggcgctttc      9600
tcatagctca cgctgtaggt atctcagttc ggtgtaggtc gttcgctcca agctgggctg      9660
tgtgcacgaa ccccccgttc agcccgaccg ctgcgcctta ccggtaact atcgtcttga      9720 gtccaacccg gtaagacacg acttatcgcc actggcagca gccactggta acaggattag      9780
cagagcgagg tatgtaggcg gtgctacaga gttcttgaag tggtggccta actacggcta      9840
cactagaagg acagtatttg gtatctgcgc tctgctgaag ccagttacct tcggaaaaag      9900
agttggtagc tcttgatccg gcaaacaaac caccgctggt agcggtggtt ttttgtttg      9960 caagcagcag attacgcgca gaaaaaaagg atctcaagaa gatcctttga tcttttctac     10020
ggggtctgac gctcagtgga acgaaaactc acgttaaggg attttggtca tgagattatc     10080
aaaaaggatc ttcacctaga tccttttaaa ttaaaaatga agttttaaat caatctaaag     10140
tatatatgag taaacttggt ctgacagtta ccaatgctta atcagtgagg cacctatctc     10200
agcgatctgt ctatttcgtt catccatagt tgcctgactc cccgtcgtgt agataactac     10260
gatacgggag ggcttaccat ctggccccag tgctgcaatg ataccgcgag acccacgctc     10320
accggctcca gatttatcag caataaacca gccagccgga agggccgagc gcagaagtgg     10380
```

-continued

```
tcctgcaact ttatccgcct ccatccagtc tattaattgt tgccgggaag ctagagtaag    10440
tagttcgcca gttaatagtt tgcgcaacgt tgttgccatt gctacaggca tcgtggtgtc    10500
acgctcgtcg tttggtatgg cttcattcag ctccggttcc caacgatcaa ggcgagttac    10560
atgatccccc atgttgtgca aaaaagcggt tagctccttc ggtcctccga tcgttgtcag    10620
aagtaagttg gccgcagtgt tatcactcat ggttatggca gcactgcata attctcttac    10680
tgtcatgcca tccgtaagat gcttttctgt gactggtgag tactcaacca agtcattctg    10740
agaatagtgt atgcggcgac cgagttgctc ttgcccggcg tcaatacggg ataataccgc    10800
gccacatagc agaactttaa aagtgctcat cattggaaaa cgttcttcgg ggcgaaaact    10860
ctcaaggatc ttaccgctgt tgagatccag ttcgatgtaa cccactcgtg cacccaactg    10920
atcttcagca tcttttactt tcaccagcgt ttctgggtga gcaaaaacag gaaggcaaaa    10980
tgccgcaaaa aagggaataa gggcgacacg gaaatgttga atactcatac tcttcctttt    11040
tcaatattat tgaagcattt atcagggtta ttgtctcatg agcggataca tatttgaatg    11100
tatttagaaa aataaacaaa taggggttcc gcgcacattt ccccgaaaag tgccacctgg    11160
gtccttttca tcacgtgcta taaaaataat tataatttaa attttttaat ataaatatat    11220
aaattaaaaa tagaaagtaa aaaaagaaat taaagaaaaa atagtttttg ttttccgaag    11280
atgtaaaaga ctctaggggg atcgccaaca aatactacct tttatcttgc tcttcctgct    11340
ctcaggtatt aatgccgaat tgtttcatct tgtctgtgta gaagaccaca cacgaaaatc    11400
ctgtgatttt acattttact tatcgttaat cgaatgtata tctatttaat ctgcttttct    11460
tgtctaataa atatatatgt aaagtacgct ttttgttgaa attttttaaa cctttgttta    11520 ttttttttc ttcattccgt aactcttcta ccttctttat ttactttcta aaatccaaat    11580 acaaacata aaaataaata aacacagagt aaattcccaa attattccat cattaaaaga    11640
tacgaggcgc gtgtaagtta caggcaagcg atccgtccta agaaaccatt attatcatga    11700
cattaaccta taaaaatagg cgtatcacga ggccctttcg tc    11742
```

<210> SEQ ID NO 33
<211> LENGTH: 2872
<212> TYPE: DNA
<213> ORGANISM: Artificial Sequence
<220> FEATURE:
<223> OTHER INFORMATION: expression cassette

<400> SEQUENCE: 33

```
atccgtacac gtttgtgccg aacccgaagt attgcaacag gtcgaagttc gtgcttagtc      60
aaaaaattag cctttttaatt ctgctgtaac ccgtacatgc ccaaaatagg gggcgggtta     120
cacagaatat ataacatcgt aggtgtctgg gtgaacagtt tattcctggc atccactaaa     180
tataatggag cccgcttttt aagctggcat ccagaaaaaa aaagaatccc agcaccaaaa     240
tattgttttc ttcaccaacc atcagttcat aggtccattc tcttagcgca actacagaga     300 acagggcac aaacaggcaa aaaacgggca caacctcaat ggagtgatgc aacctgcctg     360
gagtaaatga tgacacaagg caattgaccc acgcatgtat ctatctcatt ttcttacacc     420
ttctattacc ttctgctctc tctgatttgg aaaaagctga aaaaaaaggt tgaaaccagt     480
tccctgaaat tattccccta cttgactaat aagtatataa agacggtagg tattgattgt     540
aattctgtaa atctatttct taaacttctt aaattctact tttatagtta gtctttttttt    600 tagttttaaa acaccaagaa cttagtttcg aataaacaca cataaacaaa caaaatggct     660
gctggtgttt tcaagtcttt catgagagat ttctttgctg tcaagtacga tgaacaaaga    720
```

```
aacgacccac aagctgaaag attggatggt aacggtagat tatacccaaa ctgttcctct      780
gatgtctggt tgagatcttg tgaaagagaa atcgtcgacc caattgaagg tcaccactct      840
ggtcacatcc caaaatggat ctgtggttct ttgttgagaa atggtccagg ttcctggaag      900
gtcggtgaca tgactttcgg tcatttgttc gactgttctg ctttgttgca ccgtttcgcc      960
atcagaaacg gtcgtgtcac ttaccaaaac agatttgttg acactgaaac tttgagaaag     1020
aacagatctg ctcaaagaat tgtcgttact gaattcggta ctgctgccgt tccagaccca     1080
tgtcactcca ttttcgacag atttgctgcc atcttcagac cagactccgg tactgacaac     1140
tccatgatct ccatctaccc attcggtgac caatactaca ctttcaccga aaccccattc     1200
atgcacagaa tcaacccatg taccttggcc actgaagcta gaatctgtac caccgatttc     1260
gttggtgttg tcaaccacac ttcccaccct cacgtcttgc catctggtac tgtttacaac     1320
ttgggtacca ccatgaccag atccggtcca gcttacacta tcttgtcttt cccacacggt     1380
gaacaaatgt ttgaagatgc tcacgtcgtt gccactttac catgtagatg gaaattacat     1440
ccaggttaca tgcacacttt cggtttgact gaccattact tcgtcattgt tgaacaacca     1500
ttgtccgtct ccttgactga atacatcaag gctcaattag gtggtcaaaa cttgtctgct     1560
tgtttgaaat ggttcgaaga tcgtccaact ttgttccatt tgattgacag agtttctggt     1620
aagttggtcc aaacctacga atctgaagct ttcttctact tgcacattat taactgtttc     1680
gaaagagatg gtcacgttgt tgttgacatc tgttcctaca gaaacccaga aatgatcaac     1740
tgtatgtact tggaagctat cgccaacatg caaaccaacc caaactacgc tactttattc     1800
agaggtagac cattgagatt tgtcttgcct ctaggtacca ttccaccagc ttccattgcc     1860
aagagaggtt tggttaagtc tttctctttg gctggtctat ctgctccaca agttccagaa     1920
accatgaagc actctgtttc ccaatacgct gacatcacct acatgccaac caacggtaag     1980
caagctaccg ctggtgaaga atctccaaag agagatgcta agagaggtcg ttacgaagaa     2040
gaaaacttgg ttaacttggt caccatggaa ggttctcaag ctgaagcctt ccaaggtact     2100
aacggtattc aattgcgtcc agaaatgttg tgtgactggg gttgtgaaac cccaagaatt     2160
tactacgaaa gatacatggg taagaactac cgttatttct acgctatctc ttctgatgtc     2220
gatgctgtca acccaggtac tttaatcaag gtcgatgtct ggaacaaatc ttgtttgacc     2280
tggtgtgaag aaaacgttta cccatctgaa cctatcttcg ttccatcccc agacccaaag     2340
tccgaagatg acggtgttat cttggcttct atggttttgg gtggtttgaa cgacagatac     2400
gttggtttga ttgtcttgtg tgccaagacc atgactgaat taggtagatg tgacttccac     2460
accaacggtc ctgttccaaa gtgtttgcac ggttggttcg ctccaaatgc gatataaaag     2520 ctttgatta agccttctag tccaaaaaac acgttttttt gtcatttatt tcattttctt     2580
agaatagttt agtttattca ttttatagtc acgaatgttt tatgattcta tatagggttg     2640
caaacaagca tttttcattt tatgttaaaa caatttcagg tttacctttt attctgcttg     2700
tggtgacgcg tgtatccgcc cgctcttttg gtcacccatg tatttaattg cataaataat     2760
tcttaaaagt ggagctagtc tatttctatt tacatacctc tcatttctca tttcctcccc     2820
tcacccgatc ccgaagaaag tccaactcca gttcgattcc ctgctttcga gt              2872
```

<210> SEQ ID NO 34
<211> LENGTH: 1909
<212> TYPE: DNA
<213> ORGANISM: Artificial Sequence
<220> FEATURE:

<223> OTHER INFORMATION: expression cassette

<400> SEQUENCE: 34

```
acccgatccc gaagaaagtc caactccagt tcgattccct gctttcgagt gtgcgggcca        60
gaaaaaggaa gtgtttccct ccttcttgaa ttgatgttac cctcataaag cacgtggcct       120
cttatcgaga aagaaattac cgtcgctcgt gatttgtttg caaaaagaac aaaactgaaa       180
aaacccagac acgctcgact tcctgtcttc ctattgattg cagcttccaa tttcgtcaca       240
caacaaggtc ctagcgacgg ctcacaggtt ttgtaacaag caatcgaagg ttctggaatg       300
gcgggaaagg gtttagtacc acatgctatg atgcccactg tgatctccag agcaaagttc       360
gttcgatcgt actgttactc tctctctttc aaacagaatt gtccgaatcg tgtgacaaca       420
acagcctgtt ctcacacact cttttcttct aaccaagggg gtggtttagt ttagtagaac       480
ctcgtgaaac ttacatttac atatatataa acttgcataa attggtcaat gcaagaaata       540
catatttggt cttttctaat tcgtagtttt tcaagttctt agatgctttc tttttctctt       600
ttttacagat catcaaggaa gtaattatct acttttaca acaaatataa aacaatggct        660
ccatctatca gaaagttctt tgctggtggt gtttgtcgta ccaatgtcca attgccaggt       720
aaggttgttg tcatcactgg tgctaacact ggtattggta aggaaactgc tagagaatta       780
gcttccagag gtgccagagt ctacattgct tgtcgtgatg tcttgaaggg tgaatctgct       840
gcttctgaaa tcagagttga caccaagaac tctcaagtct tggttagaaa gttggacttg       900
tctgacacca aatccatcag agctttcgct gaaggtttct tggctgaaga aaagcaattg       960
cacattttga tcaacaacgc tggtgtcatg atgtgtccat actccaagac tgctgatggt      1020
tttgaaaccc acttgggtgt caaccatttg ggtcacttct tgttgactta cttgttgttg      1080
gaaagattga agtttctgc cccagcccgt gttgtcaacg tttcttctgt tgctcatcac      1140
atcggtaaga ttccattcca cgatttgcaa tctgaaaagc gttactccag aggtttcgct      1200
tactgtcact ccaaattggc taacgtctta ttcaccagag aattggccaa gagattacaa      1260
ggtactggtg ttaccactta cgctgtccac ccaggtgttg tcagatccga attggttaga      1320
cactcttctt tgttgtgtct attatggaga ttattctctc cattcgtcaa gaccgccaga      1380
gaaggtgctc aaacctcttt gcactgtgct ttggccgaag gtttggaacc tttgtccggt      1440
aagtacttct ctgactgtaa gagaacctgg gtttccccaa gagctagaaa caacaagact      1500
gccgaaagat tatggaacgt ttcctgtgaa ttgttgggta tcagatggga gtaaagtctg      1560
aagaatgaat gatttgatga tttctttttc cctccatttt tcttactgaa tatatcaatg      1620
atatagactt gtatagttta ttatttcaaa ttaagtagct atatatagtc aagataacgt      1680
ttgtttgaca cgattacatt attcgtcgac atcttttttc agcctgtcgt ggtagcaatt      1740
tgaggagtat tattaattga ataggttcat tttgcgctcg cataaacagt tttcgtcagg      1800
gacagtatgt tggaatgagt ggtaattaat ggtgacatga catgttatag caataccct       1860 cctcggatcg gccagttggg agcaaggtgg tacttctgtc gtcgtattt                   1909
```

```
<210> SEQ ID NO 35
<211> LENGTH: 2689
<212> TYPE: DNA
<213> ORGANISM: Artificial Sequence
<220> FEATURE:
<223> OTHER INFORMATION: expression cassette
```

<400> SEQUENCE: 35

```
tcctcggatc ggccagttgg gagcaaggtg gtacttctgt cgtcgtattt gtgcgtgtcg        60
```

-continued

```
acgctgcggg tatagaaagg gttctttact ctatagtacc tcctcgctca gcatctgctt    120
cttcccaaag atgaacgcgg cgttatgtca ctaacgacgt gcaccaactt gcggaaagtg    180
gaatcccgtt ccaaaactgg catccactaa ttgatacatc tacacaccgc acgccttttt    240
tctgaagccc actttcgtgg actttgccat atgcaaaatt catgaagtgt gataccaagt    300
cagcatacac ctcactaggg tagtttcttt ggttgtattg atcatttggt tcatcgtggt    360
tcattaattt ttttctcca ttgctttctg gctttgatct tactatcatt tggatttttg    420
tcgaaggttg tagaattgta tgtgacaagt ggcaccaagc atatataaaa aaaaaaagca    480
ttatcttcct accagagttg attgttaaaa acgtatttat agcaaacgca attgtaatta    540
attcttattt tgtatctttt cttcccttgt ctcaatcttt tatttttatt ttatttttct    600
tttcttagtt tctttcataa caccaagcaa ctaatactat aacatacaat aataatgggt    660
gatttggatg ctagaggtac ttctgctcat ccagaattat ctgaaagacc atctatcatg    720
ccatccatgt ccgatatcca agacccatct ggtgacgaca aggccactcc aagaggttct    780
gctgctggtt tgcctcaatt ggaattggct ggtcacgcta gaagattggg tcacttggaa    840
aacttctttg ctgtccaaca ccgtcaacaa atctactcct ctttcgctgt cttctgtgaa    900
ttcgacaccg cttgttcttt ggctcaattg gcttctgccg ttagaaacgt ttgtctatcc    960
aacccattat tgttgcacac cgtcgaacca aagcatccag atatcgctgg tttctaccat   1020
tccgatgaat acttgtccag accatggcca caacacgact acatgagagt tttgagagaa   1080
gtccacgttg ctgatgtcgt tatgaacggt caaaaggaac acgctcacgt tgtcagagat   1140
gctgtcgatg tcttccaagc tcacggtaac caagttacct ctgaattgtt ggaattgatg   1200
acccaaatcg aaattccaca cgcttctcaa actagaccat cctggagatt gttgtgtttc   1260
ccacacggtg aagctaacag atggagaacc tttgcctttg tctccaacca ttgttcctct   1320
gacggtctat ctggtttgaa cttcttccgt gacttgcaaa aggaattagc ccacggtcca   1380
acctctggtg ctccaggtgc cccaggtgct tctggtgtta tcttcgacta cgctcaagat   1440
gctgctactt tgccaaagtt gcctcctcca attgaccaaa aattggacta cagaccatcc   1500
aagaaggctt tgttgggttt gttggctggt aagttcgtca gagaaaaatt gggttacgtc   1560
tctgctgctc caccaaccac tccaacttct gacttggctc acccagaagg tcaccaatac   1620
tactgttact tggttaacgt cccaacttct tctgttgccc acatcaagac ccaagttaga   1680
gaaaacgtcc cacacaagtg taccttgacc ccattcttac aagcctgttg gttggtttct   1740
ttgttcaaat acggtcgtgt tttctccggt tcctggttgg aaagatacac cgatgttttg   1800
gttgccatga acaccagaca attattacca gaagacttgg aattgcaaag acaatacaga   1860
tacggttcta acgtcggtgg tgttcgttac aactacccaa ttgctccatt ggacgtcaga   1920
gacaacgatc aaaagttctg gtctttagtc gaatcttaca gattggcttt gtccgatgct   1980
cgtgacaaga acgattattt gtacgctttg ggtgctttga tgttgccaga aatctacgaa   2040
aagaagaacg ttgacgctgt cgttaatgac accatcttga accaaagaag atctggtact   2100
ttgatttcta acgttggtta cgttagagac gaacaaccaa ctgctttcgc tatcaagaac   2160 cacgtttttca gccaaggtgt tggtgccaac agaaacgctt tcgtcttgaa catctgtgcc   2220
actgaccaag gtggtttgaa tattgccatc tccattgcca agggtacttt ggcttccaga   2280
caagaaggtc aagaattatg tgacattttc aaatccactc tattaagatt ctaaagcgaa   2340
tttcttatga tttatgattt ttattattaa ataagttata aaaaaaataa gtgtatacaa   2400
```

-continued

```
atttttaaagt gactcttagg ttttaaaacg aaaattctta ttcttgagta actctttcct    2460
gtaggtcagg ttgctttctc aggtatagca tgaggtcgct cttattgacc acacctctac    2520
cggcatgccg agcaaatgcc tgcaaatcgc tccccatttc acccaattgt agatatgcta    2580
actccagcaa tgagttgatg aatctcggtg tgtattttat gtcctcagag gacaacctca    2640
cagaactttg gacagccgat tgggaaatac gaaactggga aggagaaga                 2689
```

```
<210> SEQ ID NO 36
<211> LENGTH: 2689
<212> TYPE: DNA
<213> ORGANISM: Artificial Sequence
<220> FEATURE:
<223> OTHER INFORMATION: expression cassette

<400> SEQUENCE: 36
```

```
tcctcggatc ggccagttgg gagcaaggtg gtacttctgt cgtcgtattt gtgcgtgtcg      60
acgctgcggg tatagaaagg gttctttact ctatagtacc tcctcgctca gcatctgctt     120
cttcccaaag atgaacgcgg cgttatgtca ctaacgacgt gcaccaactt gcggaaagtg     180
gaatcccgtt ccaaaactgg catccactaa ttgatacatc tacacaccgc acgccttttt     240
tctgaagccc actttcgtgg actttgccat atgcaaaatt catgaagtgt gataccaagt     300
cagcatacac ctcactaggg tagtttcttt ggttgtattg atcatttggt tcatcgtggt     360
tcattaattt ttttctcca ttgctttctg gctttgatct tactatcatt tggattttg      420 tcgaaggttg tagaattgta tgtgacaagt ggcaccaagc atatataaaa aaaaaaagca     480
ttatcttcct accagagttg attgttaaaa acgtatttat agcaaacgca attgtaatta     540
attcttattt tgtatctttt cttcccttgt ctcaatcttt tattttttatt ttatttttct    600 tttcttagtt tctttcataa caccaagcaa ctaatactat aacatacaat aataatgggt     660
gatttggatg ctagaggtac ttctgctcat ccagaattat ctgaaagacc atctatcatg     720
ccatccatgt ccgatatcca agacccatct ggtgacgaca aggccactcc aagaggttct     780
gctgctggtt tgcctcaatt ggaattggct ggtcacgcta gaagattggg tcacttggaa     840
aacttctttg ctgtccaaca ccgtcaacaa atctactcct cttctcgctgt cttctgtgaa     900 ttcgacaccg cttgttcttt ggctcaattg gcttctgccg ttagaaacgt ttgtctatcc     960
aacccattat tgttgcacac cgtcgaacca aagcatccag atatcgctgg tttctaccat    1020
tccgatgaat acttgtccag accatggcca caacacgact acatgagagt tttgagagaa    1080
gtccacgttg ctgatgtcgt tatgaacggt caaaaggaac acgctcacgt tgtcagagat    1140
gctgtcgatg tcttccaagc tcacggtaac caagttacct ctgaattgtt ggaattgatg    1200
acccaaatcg aaattccaca cgcttctcaa actagaccat cctggagatt gttgtgtttc    1260
ccacacggtg aagctaacag atggagaacc tttgcctttg tctccaacca ttgttcctct    1320
gacggtctat ctggtttgaa cttcttccgt gacttgcaaa aggaattagc ccacggtcca    1380
acctctggtg ctccaggtgc cccaggtgct tctggtgtta tcttcgacta cgctcaagat    1440
gctgctactt tgccaaagtt gcctcctcca attgaccaaa aattggacta cagaccatcc    1500
aagaaggctt tgttgggttt gttggctggt aagttcgtca gagaaaaatt gggttacgtc    1560
tctgctgctc caccaaccac tccaacttct gacttggctc acccagaagg tcaccaatac    1620
tactgttact tggttaacgt cccaacttct tctttggccc acatcaagac ccaagttaga    1680
gaaaacgtcc cacacaagtg taccttgacc ccattcttac aagcctgttg gttggtttct    1740
ttgttcaaat acggtcgtgt tttctccggt tcctggttgg aaagatacac cgatgttttg    1800
```

-continued

```
gttgccatga acaccagaca attattacca gaagacttgg aattgcaaag acaatacaga    1860
tacggttcta acgtcggtgg tgttcgttac aactacccaa ttgctccatt ggacgtcaga    1920
gacaacgatc aaaagttctg gtctttagtc gaatcttaca gattggcttt gtccgatgct    1980
cgtgacaaga acgattattt gtacgctttg ggtgctttga tgttgccaga aatctacgaa    2040
aagaagaacg ttgacgctgt cgttaatgac accatcttga accaaagaag acaaggtact    2100
ttgatttcta acgttggtta cgttagagac gaacaaccaa ctgctttcgc tatcaagaac    2160
cacgttttca gccaaggtgt tggtgccaac agaaacgctt tcgtcttgaa catctgtgcc    2220
actgaccaag gtggtttgaa tattgccatc tccattgcca agggtacttt ggcttccaga    2280
caagaaggtc aagaattatg tgacattttc aaatccactc tattaagatt ctaaagcgaa    2340
tttcttatga tttatgattt ttattattaa ataagttata aaaaaaataa gtgtatacaa    2400
attttaaagt gactcttagg ttttaaaacg aaaattctta ttcttgagta actctttcct    2460
gtaggtcagg ttgctttctc aggtatagca tgaggtcgct cttattgacc acacctctac    2520
cggcatgccg agcaaatgcc tgcaaatcgc tccccatttc acccaattgt agatatgcta    2580
actccagcaa tgagttgatg aatctcggtg tgtattttat gtcctcagag gacaacctca    2640
cagaactttg gacagccgat tgggaaatac gaaactggga aggagaaga    2689
```

<210> SEQ ID NO 37
<211> LENGTH: 2689
<212> TYPE: DNA
<213> ORGANISM: Artificial Sequence
<220> FEATURE:
<223> OTHER INFORMATION: expression cassette

<400> SEQUENCE: 37

```
tcctcggatc ggccagttgg gagcaaggtg gtacttctgt cgtcgtattt gtgcgtgtcg      60
acgctgcggg tatagaaagg gttctttact ctatagtacc tcctcgctca gcatctgctt     120
cttcccaaag atgaacgcgg cgttatgtca ctaacgacgt gcaccaactt gcggaaagtg     180
gaatcccgtt ccaaaactgg catccactaa ttgatacatc tacacaccgc acgccttttt     240
tctgaagccc actttcgtgg actttgccat atgcaaaatt catgaagtgt gataccaagt     300
cagcatacac ctcactaggg tagtttcttt ggttgtattg atcatttggt tcatcgtggt     360
tcattaattt tttttctcca ttgctttctg gctttgatct tactatcatt tggatttttg     420
tcgaaggttg tagaattgta tgtgacaagt ggcaccaagc atatataaaa aaaaaaagca     480
ttatcttcct accagagttg attgttaaaa acgtatttat agcaaacgca attgtaatta     540
attcttattt tgtatctttt cttcccttgt ctcaatcttt tatttttatt ttattttct     600 tttcttagtt tctttcataa caccaagcaa ctaatactat aacatacaat aataatgggt     660
gatttggatg ctagaggtac ttctgctcat ccagaattat ctgaaagacc atctatcatg     720
ccatccatgt ccgatatcca agacccatct ggtgacgaca aggccactcc aagaggttct     780
gctgctggtt tgcctcaatt ggaattggct ggtcacgcta aagattggg tcacttggaa     840 aacttctttg ctgtccaaca ccgtcaacaa atctactcct ctttcgctgt cttctgtgaa     900
ttcgacaccg cttgttcttt ggctcaattg gcttctgccg ttagaaacgt ttgtctatcc     960
aacccattat tgttgcacac cgtcgaacca aagcatccag atatcgctgg tttctaccat    1020
tccgatgaat acttgtccag accatggcca caacacgact acatgagagt tttgagagaa    1080
gtccacgttg ctgatgtcgt tatgaacggt caaaaggaac acgctcacgt tgtcagagat    1140
```

-continued

```
gctgtcgatg tcttccaagc tcacggtaac caagttacct ctgaattgtt ggaattgatg      1200
acccaaatcg aaattccaca cgcttctcaa actagaccat cctggagatt gttgtgtttc      1260
ccacacggtg aagctaacag atggagaacc tttgcctttg tctccaacca ttgttcctct      1320
gacggtctat ctggtttgaa cttcttccgt gacttgcaaa aggaattagc ccacggtcca      1380
acctctggtg ctccaggtgc cccaggtgct tctggtgtta tcttcgacta cgctcaagat      1440
gctgctactt tgccaaagtt gcctcctcca attgaccaaa aattggacta cagaccatcc      1500
aagaaggctt tgttgggttt gttggctggt aagttcgtca gagaaaaatt gggttacgtc      1560
tctgctgctc caccaaccac tccaacttct gacttggctc acccagaagg tcaccaatac      1620
tactgttact tggttaacgt cccaacttct tctgttgccc acatcaagac ccaagttaga      1680
gaaaacgtcc cacacaagtg taccttgacc ccattcttac aagcctgttg gttggtttct      1740
ttgttcaaat acggtcgtgt tttctccggt tcctggttgg aaagatacac cgatgttttg      1800
gttgccatga acaccagaca attattacca gaagacttgg aattgcaaag acaatacaga      1860
tacggttcta acatcggtgg tgttcgttac aactacccaa ttgctccatt ggacgtcaga      1920
gacaacgatc aaaagttctg gtctttagtc gaatcttaca gattggcttt gtccgatgct      1980
cgtgacaaga acgattattt gtacgctttg ggtgctttga tgttgccaga aatctacgaa      2040
aagaagaacg ttgacgctgt cgttaatgac accatcttga accaaagaag acaaggtact      2100
ttgatttcta acgttggtta cgttagagac gaacaaccaa ctgctttcgc tatcaagaac      2160 cacgtttttca gccaaggtgt tggtgccaac agaaacgctt tcgtcttgaa catctgtgcc      2220
actgaccaag gtggtttgaa tattgccatc tccattgcca agggtacttt ggcttccaga      2280
caagaaggtc aagaattatg tgacatttttc aaatccactc tattaagatt ctaaagcgaa      2340
tttcttatga tttatgattt ttattattaa ataagttata aaaaaaataa gtgtatacaa      2400 atttttaaagt gactcttagg ttttaaaacg aaaattctta ttcttgagta actctttcct      2460
gtaggtcagt tttgctttctc aggtatagca tgaggtcgct cttattgacc acacctctac      2520
cggcatgccg agcaaatgcc tgcaaatcgc tccccatttc acccaattgt agatatgcta      2580
actccagcaa tgagttgatg aatctcggtg tgtattttat gtcctcagag gacaacctca      2640
cagaactttg gacagccgat tgggaaatac gaaactggga aggagaaga                  2689
```

```
<210> SEQ ID NO 38
<211> LENGTH: 2689
<212> TYPE: DNA
<213> ORGANISM: Artificial Sequence
<220> FEATURE:
<223> OTHER INFORMATION: expression cassette

<400> SEQUENCE: 38
```

```
tcctcggatc ggccagttgg gagcaaggtg gtacttctgt cgtcgtattt gtgcgtgtcg        60
acgctgcggg tatagaaagg gttctttact ctatagtacc tcctcgctca gcatctgctt       120
cttcccaaag atgaacgcgg cgttatgtca ctaacgacgt gcaccaactt gcggaaagtg       180
gaatcccgtt ccaaaactgg catccactaa ttgatacatc tacacaccgc acgcctttttt      240 tctgaagccc actttcgtgg actttgccat atgcaaaatt catgaagtgt gataccaagt       300
cagcatacac ctcactaggg tagtttcttt ggttgtattg atcatttggt tcatcgtggt       360
tcattaattt ttttttctcca ttgctttctg gctttgatct tactatcatt tggattttttg     420 tcgaaggttg tagaattgta tgtgacaagt ggcaccaagc atatataaaa aaaaaaagca       480
ttatcttcct accagagttg attgttaaaa acgtatttat agcaaacgca attgtaatta       540
```

-continued

```
attcttattt tgtatctttt cttcccttgt ctcaatcttt tatttttatt ttattttct       600 tttcttagtt tctttcataa caccaagcaa ctaatactat aacatacaat aataatgggt       660
gatttggatg ctagaggtac ttctgctcat ccagaattat ctgaaagacc atctatcatg       720
ccatccatgt ccgatatcca agacccatct ggtgacgaca aggccactcc aagaggttct       780
gctgctggtt tgcctcaatt ggaattggct ggtcacgcta gaagattggg tcacttggaa       840
aacttctttg ctgtccaaca ccgtcaacaa atctactcct ctttcgctgt cttctgtgaa       900
ttcgacaccg cttgttcttt ggctcaattg gcttctgccg ttagaaacgt ttgtctatcc       960
aacccattat tgttgcacac cgtcgaacca aagcatccag atatcgctgg tttctaccat      1020
tccgatgaat acttgtccag accatggcca caacacgact acatgagagt tttgagagaa      1080
gtccacgttg ctgatgtcgt tatgaacggt caaaaggaac acgctcacgt tgtcagagat      1140
gctgtcgatg tcttccaagc tcacggtaac caagttacct ctgaattgtt ggaattgatg      1200
acccaaatcg aaattccaca cgcttctcaa actagaccat cctggagatt gttgtgtttc      1260
ccacacggtg aagctaacag atggagaacc tttgcctttg tctccaacca ttgttcctct      1320
gacggtctat ctggtttgaa cttcttccgt gacttgcaaa aggaattagc ccacggtcca      1380
acctctggtg ctccaggtgc cccaggtgct tctggtgtta tcttcgacta cgctcaagat      1440
gctgctactt tgccaaagtt gcctcctcca attgaccaaa aattggacta cagaccatcc      1500
aagaaggctt tgttgggttt gttggctggt aagttcgtca gagaaaaatt gggttacgtc      1560
tctgctgctc caccaaccac tccaacttct gacttggctc acccagaagg tcaccaatac      1620
tactgttact tggttaacgt cccaacttct tctgttgccc acatcaagac ccaagttaga      1680
gaaaacgtcc cacacaagtg taccttgacc ccattcttac aagcctgttg gttggtttct      1740
ttgttcaaat acggtcgtgt tttctccggt tcctggttgg aaagatacac cgatgttttg      1800
gttgccatga acaccagaca attattacca gaagacttgg aattgcaaag acaatacaga      1860
tacggttcta acgtcggtgc tgttcgttac aactacccaa ttgctccatt ggacgtcaga      1920
gacaacgatc aaaagttctg gtctttagtc gaatcttaca gattggcttt gtccgatgct      1980
cgtgacaaga acgattattt gtacgctttg ggtgctttga tgttgccaga aatctacgaa      2040
aagaagaacg ttgacgctgt cgttaatgac accatcttga accaaagaag acaaggtact      2100
ttgatttcta cgttggtta cgttagagac gaacaaccaa ctgctttcgc tatcaagaac      2160
cacgttttca gccaaggtgt tggtgccaac agaaacgctt tcgtcttgaa catctgtgcc      2220
actgaccaag gtggtttgaa tattgccatc tccattgcca agggtacttt ggcttccaga      2280
caagaaggtc aagaattatg tgacattttc aaatccactc tattaagatt ctaaagcgaa      2340
tttcttatga tttatgattt ttattattaa ataagttata aaaaaaataa gtgtatacaa      2400
attttaaagt gactcttagg ttttaaaacg aaaattctta ttcttgagta actctttcct      2460
gtaggtcagt tgctttctc aggtatagca tgaggtcgct cttattgacc acacctctac        2520
cggcatgccg agcaaatgcc tgcaaatcgc tccccatttc acccaattgt agatatgcta      2580
actccagcaa tgagttgatg aatctcggtg tgtattttat gtcctcagag gacaacctca      2640
cagaactttg gacagccgat tgggaaatac gaaactggga aggagaaga                  2689
```

<210> SEQ ID NO 39
<211> LENGTH: 2689
<212> TYPE: DNA
<213> ORGANISM: Artificial Sequence
<220> FEATURE:

-continued

<223> OTHER INFORMATION: expression cassette

<400> SEQUENCE: 39

```
tcctcggatc ggccagttgg gagcaaggtg gtacttctgt cgtcgtattt gtgcgtgtcg        60
acgctgcggg tatagaaagg gttctttact ctatagtacc tcctcgctca gcatctgctt       120
cttcccaaag atgaacgcgg cgttatgtca ctaacgacgt gcaccaactt gcggaaagtg       180
gaatcccgtt ccaaaactgg catccactaa ttgatacatc tacacaccgc acgcctttt       240 tctgaagccc actttcgtgg actttgccat atgcaaaatt catgaagtgt gataccaagt       300
cagcatacac ctcactaggg tagtttcttt ggttgtattg atcatttggt tcatcgtggt       360
tcattaattt ttttttctcca ttgctttctg gctttgatct tactatcatt tggatttttg       420
tcgaaggttg tagaattgta tgtgacaagt ggcaccaagc atatataaaa aaaaaaagca       480
ttatcttcct accagagttg attgttaaaa acgtatttat agcaaacgca attgtaatta       540
attcttattt tgtatctttt cttcccttgt ctcaatcttt tattttatt ttatttttct       600 tttcttagtt tctttcataa caccaagcaa ctaatactat aacatacaat aataatgggt       660
gatttggatg ctagaggtac ttctgctcat ccagaattat ctgaaagacc atctatcatg       720
ccatccatgt ccgatatcca agacccatct ggtgacgaca aggccactcc aagaggttct       780
gctgctggtt tgcctcaatt ggaattggct ggtcacgcta gaagattggg tcacttggaa       840
aacttctttg ctgtccaagc tcgtcaacaa atctactcct ctttcgctgt cttctgtgaa       900
ttcgacaccg cttgttcttt ggctcaattg gcttctgccg ttagaaacgt ttgtctatcc       960
aacccattat tgttgcacac cgtcgaacca aagcatccag atatcgctgg tttctaccat      1020
tccgatgaat acttgtccag accatggcca caacacgact acatgagagt tttgagagaa      1080
gtccacgttg ctgatgtcgt tatgaacggt caaaaggaac acgctcacgt tgtcagagat      1140
gctgtcgatg tcttccaagc tcacggtaac caagttacct ctgaattgtt ggaattgatg      1200
acccaaatcg aaattccaca cgcttctcaa actagaccat cctggagatt gttgtgtttc      1260
ccacacggtg aagctaacag atggagaacc tttgcctttg tctccaacca ttgttcctct      1320
gacggtctat ctggtttgaa cttcttccgt gacttgcaaa aggaattagc ccacggtcca      1380
acctctggtg ctccaggtgc cccaggtgct tctggtgtta tcttcgacta cgctcaagat      1440
gctgctactt tgccaaagtt gcctcctcca attgaccaaa aattggacta cagaccatcc      1500
aagaaggctt tgttgggttt gttggctggt aagttcgtca gagaaaaatt gggttacgtc      1560
tctgctgctc caccaaccac tccaacttct gacttggctc acccagaagg tcaccaatac      1620
tactgttact tggttaacgt cccaacttct tctgttgccc acatcaagac ccaagttaga      1680
gaaaacgtcc cacacaagtg taccttgacc ccattcttac aagcctgttg gttggtttct      1740
ttgttcaaat acggtcgtgt tttctccggt tcctggttgg aaagatacac cgatgttttg      1800
gttgccatga caccagaca attattacca gaagacttgg aattgcaaag acaatacaga      1860
tacggttcta acatcggtgg tgttcgttac aactacccaa ttgctccatt ggacgtcaga      1920
gacaacgatc aaaagttctg gtctttagtc gaatcttaca gattggcttt gtccgatgct      1980
cgtgacaaga acgattattt gtacgctttg ggtgctttga tgttgccaga aatctacgaa      2040
aagaagaacg ttgacgctgt cgttaatgac accatcttga accaaagaag acaaggtact      2100
ttgatttcta acgttggtta cgttagagac gaacaaccaa ctgctttcgc tatcaagaac      2160
cacgttttca gccaaggtgt tggtgccaac agaaacgctt cgtcttgaa catctgtgcc      2220 actgaccaag gtggtttgaa tattgccatc tccattgcca agggtacttt ggcttccaga      2280
```

-continued

```
caagaaggtc aagaattatg tgacattttc aaatccactc tattaagatt ctaaagcgaa      2340
tttcttatga tttatgattt ttattattaa ataagttata aaaaaaataa gtgtatacaa      2400
attttaaagt gactcttagg ttttaaaacg aaaattctta ttcttgagta actctttcct      2460
gtaggtcagg ttgctttctc aggtatagca tgaggtcgct cttattgacc acacctctac      2520
cggcatgccg agcaaatgcc tgcaaatcgc tccccatttc acccaattgt agatatgcta      2580
actccagcaa tgagttgatg aatctcggtg tgtattttat gtcctcagag gacaacctca      2640
cagaactttg gacagccgat tgggaaatac gaaactggga aggagaaga                 2689
```

<210> SEQ ID NO 40
<211> LENGTH: 2689
<212> TYPE: DNA
<213> ORGANISM: Artificial Sequence
<220> FEATURE:
<223> OTHER INFORMATION: expression cassette

<400> SEQUENCE: 40

```
tcctcggatc ggccagttgg gagcaaggtg gtacttctgt cgtcgtattt gtgcgtgtcg        60
acgctgcggg tatagaaagg gttctttact ctatagtacc tcctcgctca gcatctgctt       120
cttcccaaag atgaacgcgg cgttatgtca ctaacgacgt gcaccaactt gcggaaagtg       180
gaatcccgtt ccaaaactgg catccactaa ttgatacatc tacacaccgc acgccttttt       240
tctgaagccc actttcgtgg actttgccat atgcaaaatt catgaagtgt gataccaagt       300
cagcatacac ctcactaggg tagtttcttt ggttgtattg atcatttggt tcatcgtggt       360
tcattaattt ttttttctcca ttgctttctg gctttgatct tactatcatt tggattttttg      420 tcgaaggttg tagaattgta tgtgacaagt ggcaccaagc atatataaaa aaaaaaagca       480
ttatcttcct accagagttg attgttaaaa acgtatttat agcaaacgca attgtaatta       540
attcttattt tgtatctttt cttcccttgt ctcaatcttt tattttttatt ttatttttct       600 tttcttagtt tctttcataa caccaagcaa ctaatactat aacatacaat aataatgggt       660
gatttggatg ctagaggtac ttctgctcat ccagaattat ctgaaagacc atctatcatg       720
ccatccatgt ccgatatcca agacccatct ggtgacgaca aggccactcc aagaggttct       780
gctgctggtt tgcctcaatt ggaattggct ggtcacgcta gaagattggg tcacttggaa       840
aacttctttg ctgtccaaca ccgtcaacaa atctactcct ctttcgctgt cttctgtgaa       900
ttcgacaccg cttgttcttt ggctcaattg gcttctgccg ttagaaacgt ttgtctatcc       960
aacccattat tgttgcacac cgtcgaacca aagcatccag atatcgctgg tttctaccat      1020
tccgatgaat acttgtccag accatggcca caacacgact acatgagagt tttgagagaa      1080
gtccacgttg ctgatgtcgt tatgaacggg caaaaggaac acgctcacgt tgtcagagat      1140
gctgtcgatg tcttccaagc tcacggtaac caagttacct ctgaattgtt ggaattgatg      1200
acccaaatcg aaattccaca cgcttctcaa actagaccat cctggagatt gttgtgtttc      1260
ccacacggtg aagctaacag atggagaacc tttgcctttg tctccaacca ttgttcctct      1320
gacggtctat ctggtttgaa cttcttccgt gacttgcaaa aggaattagc ccacggtcca      1380
acctctggtc tccaggtgc cccaggtgct tctggtgtta tcttcgacta cgctcaagat      1440
gctgctactt tgccaaagtt gcctcctcca attgaccaaa aattggacta cagaccatcc      1500
aagaaggctt tgttgggttt gttggctggt aagttcgtca gagaaaaatt gggttacgtc      1560
tctgctgctc caccaaccac tccaacttct gacttggctc acccagaagg tcaccaatac      1620
```

-continued

```
tactgttact tggttaacgt cccaacttct tctgttgccc acatcaagac ccaagttaga    1680
gaaaacgtcc cacacaagtg taccttgacc ccattcttac aagcctgttg gttggtttct    1740
ttgttcaaat acggtcgtgt tttctccggt tcctggttgg aaagatacac cgatgttttg    1800
gttgccatga acaccagaca attattacca gaagacttgg aattgcaaag acaatacaga    1860
tacggttcta acatcggtgc tgttcgttac aactacccaa ttgctccatt ggacgtcaga    1920
gacaacgatc aaaagttctg gtctttagtc gaatcttaca gattggcttt gtccgatgct    1980
cgtgacaaga acgattattt gtacgctttg ggtgctttga tgttgccaga aatctacgaa    2040
aagaagaacg ttgacgctgt cgttaatgac accatcttga accaaagaag acaaggtact    2100
ttgatttcta acgttggtta cgttagagac gaacaaccaa ctgctttcgc tatcaagaac    2160 cacgtttttca gccaaggtgt tggtgccaac agaaacgctt tcgtcttgaa catctgtgcc    2220
actgaccaag gtggtttgaa tattgccatc tccattgcca agggtacttt ggcttccaga    2280
caagaaggtc aagaattatg tgacattttc aaatccactc tattaagatt ctaaagcgaa    2340
tttcttatga tttatgattt ttattattaa ataagttata aaaaaaataa gtgtatacaa    2400
attttaaagt gactcttagg ttttaaaacg aaaattctta ttcttgagta actctttcct    2460
gtaggtcagg ttgctttctc aggtatagca tgaggtcgct cttattgacc acacctctac    2520
cggcatgccg agcaaatgcc tgcaaatcgc tccccatttc acccaattgt agatatgcta    2580
actccagcaa tgagttgatg aatctcggtg tgtattttat gtcctcagag gacaacctca    2640
cagaactttg gacagccgat tgggaaatac gaaactggga aggagaaga              2689
```

```
<210> SEQ ID NO 41
<211> LENGTH: 2689
<212> TYPE: DNA
<213> ORGANISM: Artificial Sequence
<220> FEATURE:
<223> OTHER INFORMATION: expression cassette

<400> SEQUENCE: 41
```

```
tcctcggatc ggccagttgg gagcaaggtg gtacttctgt cgtcgtattt gtgcgtgtcg      60
acgctgcggg tatagaaagg gttctttact ctatagtacc tcctcgctca gcatctgctt     120
cttcccaaag atgaacgcgg cgttatgtca ctaacgacgt gcaccaactt gcggaaagtg     180
gaatcccgtt ccaaaactgg catccactaa ttgatacatc tacacaccgc acgcctttt     240 tctgaagccc actttcgtgg actttgccat atgcaaaatt catgaagtgt gataccaagt     300
cagcatacac ctcactaggg tagtttcttt ggttgtattg atcatttggt tcatcgtggt     360
tcattaattt ttttttctcca ttgctttctg ctttgatct tactatcatt tggatttttg     420
tcgaaggttg tagaattgta tgtgacaagt ggcaccaagc atatataaaa aaaaaaagca     480
ttatcttcct accagagttg attgttaaaa acgtatttat agcaaacgca attgtaatta     540
attcttattt tgtatctttt cttcccttgt ctcaatcttt tattttttatt ttattttttct     600 tttcttagtt tctttcataa caccaagcaa ctaaatactat aacatacaat aataatgggt     660
gatttggatg ctagaggtac ttctgctcat ccagaattat ctgaaagacc atctatcatg     720
ccatccatgt ccgatatcca agacccatct ggtgacgaca aggccactcc aagaggttct     780
gctgctggtt tgcctcaatt ggaattggct ggtcacgcta gaagattggg tcacttggaa     840
aacttctttg ctgtccaaca ccgtcaacaa atctactcct ctttcgctgt cttctgtgaa     900
ttcgacaccg cttgttcttt ggctcaattg gcttctgccg ttagaaacgt ttgtctatcc     960
aacccattat tgttgcacac cgtcgaacca aagcatccag atatcgctgg tttctaccat    1020
```

-continued

```
tccgatgaat acttgtccag accatggcca caacacgact acatgagagt tttgagagaa   1080
gtccacgttg ctgatgtcgt tatgaacggt caaaaggaac acgctcacgt tgtcagagat   1140
gctgtcgatg tcttccaagc tcacggtaac caagttacct ctgaattgtt ggaattgatg   1200
acccaaatcg aaattccaca cgcttctcaa actagaccat cctggagatt gttgtgtttc   1260
ccacacggtg aagctaacag atggagaacc tttgcctttg tctccaacca ttgttcctct   1320
gacggtctat ctggtttgaa cttcttccgt gacttgcaaa aggaattagc ccacggtcca   1380
acctctggtg ctccaggtgc cccaggtgct tctggtgtta tcttcgacta cgctcaagat   1440
gctgctactt tgccaaagtt gcctcctcca attgaccaaa aattggacta cagaccatcc   1500
aagaaggctt tgttgggttt gttggctggt aagttcgtca gagaaaaatt gggttacgtc   1560
tctgctgctc caccaaccac tccaacttct gacttggctc acccagaagg tcaccaatac   1620
tactgttact tggttaacgt cccaacttct tctgttgccc acatcaagac ccaagttaga   1680
gaaaacgtcc cacacaagtg taccttgacc ccattcttac aagcctgttg gttggtttct   1740
ttgttcaaat acggtcgtgt tttctccggt tcctggttgg aaagatacac cgatgttttg   1800
gttgccatga acaccagaca attattacca gaagacttgg aattgcaaag acaatacaga   1860
tacggttcta acatcggtgc tgttcgttac aactacccaa ttgctccatt ggacgtcaga   1920
gacaacgatc aaaagttctg gtctttagtc gaatcttaca gattggcttt gtccgatgct   1980
cgtgacaaga acgattattt gtacgctttg ggtgctttga tgttgccaga aatctacgaa   2040
aagaagaacg ttgacgctgt cgttaatgac accatcttga accaaagaag acaaggtact   2100
ttgttgtcta acgttggtta cgttagagac gaacaaccaa ctgctttcgc tatcaagaac   2160
cacgttttca gccaaggtgt tggtgccaac agaaacgctt cgtcttgaa catctgtgcc   2220 actgaccaag gtggtttgaa tattgccatc tccattgcca agggtacttt ggcttccaga   2280
caagaaggtc aagaattatg tgacattttc aaatccactc tattaagatt ctaaagcgaa   2340
tttcttatga tttatgattt ttattattaa ataagttata aaaaaaataa gtgtatacaa   2400
attttaaagt gactcttagg ttttaaaacg aaaattctta ttcttgagta actctttcct   2460
gtaggtcagg ttgctttctc aggtatagca tgaggtcgct cttattgacc acacctctac   2520
cggcatgccg agcaaatgcc tgcaaatcgc tccccatttc acccaattgt agatatgcta   2580
actccagcaa tgagttgatg aatctcggtg tgtatttat gtcctcagag acaacctca   2640 cagaactttg gacagccgat tgggaaatac gaaactggga aggagaaga               2689
```

```
<210> SEQ ID NO 42
<211> LENGTH: 2689
<212> TYPE: DNA
<213> ORGANISM: Artificial Sequence
<220> FEATURE:
<223> OTHER INFORMATION: expression cassette

<400> SEQUENCE: 42
```

```
tcctcggatc ggccagttgg gagcaaggtg gtacttctgt cgtcgtattt gtgcgtgtcg     60
acgctgcggg tatagaaagg gttctttact ctatagtacc tcctcgctca gcatctgctt    120
cttcccaaag atgaacgcgg cgttatgtca ctaacgacgt gcaccaactt gcggaaagtg    180
gaatcccgtt ccaaaactgg catccactaa ttgatacatc tacacaccgc acgccttttt    240
tctgaagccc actttcgtgg actttgccat atgcaaaatt catgaagtgt gataccaagt    300
cagcatacac ctcactaggg tagtttcttt ggttgtattg atcatttggt tcatcgtggt    360
```

-continued

```
tcattaattt ttttctccca ttgctttctg gctttgatct tactatcatt tggatttttg        420
tcgaaggttg tagaattgta tgtgacaagt ggcaccaagc atatataaaa aaaaaaagca        480
ttatcttcct accagagttg attgttaaaa acgtatttat agcaaacgca attgtaatta        540
attcttattt tgtatctttt cttcccttgt ctcaatcttt tatttttatt ttatttttct        600
tttcttagtt tctttcataa caccaagcaa ctaatactat aacatacaat aataatgggt        660
gatttggatg ctagaggtac ttctgctcat ccagaattat ctgaaagacc atctatcatg        720
ccatccatgt ccgatatcca agacccatct ggtgacgaca aggccactcc aagaggttct        780
gctgctggtt tgcctcaatt ggaattggct ggtcacgcta gaagattggg tcacttggaa        840
aacttctttg ctgtccaagc tcgtcaacaa atctactcct ctttcgctgt cttctgtgaa        900
ttcgacaccg cttgttcttt ggctcaattg gcttctgccg ttagaaacgt ttgtctatcc        960
aacccattat tgttgcacac cgtcgaacca aagcatccag atatcgctgg tttctaccat       1020
tccgatgaat acttgtccag accatggcca caacacgact acatgagagt tttgagagaa       1080
gtccacgttg ctgatgtcgt tatgaacggt caaaaggaac acgctcacgt tgtcagagat       1140
gctgtcgatg tcttccaagc tcacggtaac caagttacct ctgaattgtt ggaattgatg       1200
acccaaatcg aaattccaca cgcttctcaa actagaccat cctggagatt gttgtgtttc       1260
ccacacggtg aagctaacag atggagaacc tttgcctttg tctccaacca ttgttcctct       1320
gacggtctat ctggtttgaa cttcttccgt gacttgcaaa aggaattagc ccacggtcca       1380
acctctggtg ctccaggtgc cccaggtgct tctggtgtta tcttcgacta cgctcaagat       1440
gctgctactt tgccaaagtt gcctcctcca attgaccaaa aattggacta cagaccatcc       1500
aagaaggctt tgttgggttt gttggctggt aagttcgtca gagaaaaatt gggttacgtc       1560
tctgctgctc caccaaccac tccaacttct gacttggctc acccagaagg tcaccaatac       1620
tactgttact tggttaacgt cccaacttct tctgttgccc acatcaagac ccaagttaga       1680
gaaaacgtcc cacacaagtg taccttgacc ccattcttac aagcctgttg gttggtttct       1740
ttgttcaaat acggtcgtgt tttctccggt tcctggttgg aaagatacac cgatgttttg       1800
gttgccatga acaccagaca attattacca gaagacttgg aattgcaaag acaatacaga       1860
tacggttcta acatcggtgc tgttcgttac aactacccaa ttgctccatt ggacgtcaga       1920
gacaacgatc aaaagttctg gtctttagtc gaatcttaca gattggcttt gtccgatgct       1980
cgtgacaaga acgattattt gtacgctttg ggtgctttga tgttgccaga aatctacgaa       2040
aagaagaacg ttgacgctgt cgttaatgac accatcttga accaaagaag acaaggtact       2100
ttgttgtcta acgttggtta cgttagagac gaacaaccaa ctgctttcgc tatcaagaac       2160
cacgttttca gccaaggtgt tggtgccaac agaaacgctt tcgtcttgaa catctgtgcc       2220
actgaccaag gtggtttgaa tattgccatc tccattgcca agggtacttt ggcttccaga       2280
caagaaggtc aagaattatg tgacattttc aaatccactc tattaagatt ctaaagcgaa       2340
tttcttatga tttatgattt ttattattaa ataagttata aaaaaaataa gtgtatacaa       2400
attttaaagt gactcttagg ttttaaaacg aaaattctta ttcttgagta actctttcct       2460
gtaggtcagt ttgctttctc aggtatagca tgaggtcgct cttattgacc acacctctac       2520
cggcatgccg agcaaatgcc tgcaaatcgc tccccatttc acccaattgt agatatgcta       2580
actccagcaa tgagttgatg aatctcggtg tgtattttat gtcctcagag gacaacctca       2640
cagaactttg gacagccgat tgggaaatac gaaactggga aggagaaga               2689
```

```
<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
atccgtacac gtttgtgccg                                                    20

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
actcgaaagc agggaatcga ac                                                 22

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
aaatacgacg acagaagtac c                                                  21

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
tcctcggatc ggccagttg                                                     19

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
tcctcggatc ggccagttg                                                     19

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
tcttctcctt cccagtttcg                                                    20

<210> SEQ ID NO 49
<211> LENGTH: 320
<212> TYPE: DNA
<213> ORGANISM: Artificial Sequence
<220> FEATURE:
<223> OTHER INFORMATION: FW primer donor DNA flank sequence
```

-continued

```
<400> SEQUENCE: 49
gtctgcatag gagccttctg caattactca tctcatcgta ttcgtcataa cccgttacgt    60
aactgatttg accaagaagc gtaatgaaaa ttttgagcgg acgccgaaac gttgtttttt   120
ttttgcttta gtccagataa taaccttta taattttctt tttagggagg aagaccggtc    180
taagctctta gaggttctcg catacccaag taaaagctaa gaccgaagca aacacgcagg   240
ataattttcc ggtttactct cactgcagct atccgtacac gtttgtgccg aacccgaagt   300
attgcaacag gtcgaagttc                                              320

<210> SEQ ID NO 50
<211> LENGTH: 668
<212> TYPE: DNA
<213> ORGANISM: Artificial Sequence
<220> FEATURE:
<223> OTHER INFORMATION: donor DNA flank sequence

<400> SEQUENCE: 50
acagaacttt ggacagccga ttgggaaata cgaaactggg aaggagaaga catcttgatt    60
tatgtcttgt ttgaggagat ttcggataaa tattcttcga ggggaaaatg tcgtaaaaat   120
aaaaacaata aagaaacaaa acgattaaaa gaaaaactca accatcctca aaagtcctcc   180
tctttttttt cacgtgctgc gctgatgtaa gcagcaggac atggcaggaa gaaaatcgga   240
gaattgtggc cgcgacacct gacaaacaat cctcaggcaa atgtaaaatt gtacatgaaa   300
ggctgcgtag tcaatgtctt agaaggccgg cccgcatgat ccagaagcag accataaaaa   360
aaataaaaat tcgcggtctg gcagcaggca taagatgcat agcgttatcc taaatgacat   420
cacgatgata aatcctccgc cgcatgatgc ttttgatttg cctaagggcc tgccatcgtg   480
ctggctcaaa ctattgaggg tcaacatacc ttgaaaatcc aagtaaaagg atggatatcg   540
ttatactaaa agcaacacag aaaaggtcca cgtcagttcc acacaataac atttacgtag   600
tgttcacgcg aagcagttac atctcaacta acataattgc tggtgagcct acaacactgc   660
atgcgtaa                                                            668

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
gtctgcatag gagccttctg                                                20

<210> SEQ ID NO 52
<211> LENGTH: 70
<212> TYPE: DNA
<213> ORGANISM: Artificial Sequence
<220> FEATURE:
<223> OTHER INFORMATION: REV primer

<400> SEQUENCE: 52
gaacttcgac ctgttgcaat acttcgggtt cggcacaaac gtgtacggat agctgcagtg    60
agagtaaacc                                                          70

<210> SEQ ID NO 53
<211> LENGTH: 78
<212> TYPE: DNA
<213> ORGANISM: Artificial Sequence
```

-continued

```
<220> FEATURE:
<223> OTHER INFORMATION: primer

<400> SEQUENCE: 53
acagaacttt ggacagccga ttgggaaata cgaaactggg aaggagaaga catcttgatt      60
tatgtcttgt ttgaggag                                                    78

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
ttacgcatgc agtgttgtag gc                                               22

<210> SEQ ID NO 55
<211> LENGTH: 553
<212> TYPE: DNA
<213> ORGANISM: Artificial Sequence
<220> FEATURE:
<223> OTHER INFORMATION: expression cassette

<400> SEQUENCE: 55
catgtttgac agcttatcat cgataatccg gagctagcat gcggccgctc tagaactagt      60
ggatcccccg ggctgcagtc tttgaaaaga taatgtatga ttatgctttc actcatattt     120
atacagaaac ttgatgtttt ctttcgagta tatacaaggt gattacatgt acgtttgaag     180
tacaactcta gattttgtag tgccctcttg ggctagcggt aaaggtgcgc attttttcac     240
accctacaat gttctgttca aaagattttg gtcaaacgct gtagaagtga aagttggtgc     300
gcatgtttcg gcgttcgaaa cttctccgca gtgaaagata aatgatcgga gagaaaggcc     360
cgggcgtgtt ttagagctag aaatagcaag ttaaaataag gctagtccgt tatcaacttg     420
aaaaagtggc accgagtcgg tggtgctttt tttgtttttt atgtctgggg ggcccggtac     480
ccagcttttg ttccctttag tgagggttaa ttccgagctt ggcgtaatca tggtcatagc     540
tgtttcctgt gtg                                                        553

<210> SEQ ID NO 56
<211> LENGTH: 20
<212> TYPE: DNA
<213> ORGANISM: Artificial Sequence
<220> FEATURE:
<223> OTHER INFORMATION: genomic target sequence

<400> SEQUENCE: 56
ggagagaaag gcccgggcgt                                                  20

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
catgtttgac agcttatcat c                                                21

<210> SEQ ID NO 58
<211> LENGTH: 21
<212> TYPE: DNA
```

-continued

```
<213> ORGANISM: Artificial Sequence
<220> FEATURE:
<223> OTHER INFORMATION: primer

<400> SEQUENCE: 58
cacacaggaa acagctatga c                                              21

<210> SEQ ID NO 59
<211> LENGTH: 73
<212> TYPE: DNA
<213> ORGANISM: Artificial Sequence
<220> FEATURE:
<223> OTHER INFORMATION: primer

<400> SEQUENCE: 59
tcttaaccca actgcacaga acaaaaacct gcaggaaacg aagataaatc ccggtgccat     60
ttcaaagaat acg                                                       73

<210> SEQ ID NO 60
<211> LENGTH: 78
<212> TYPE: DNA
<213> ORGANISM: Artificial Sequence
<220> FEATURE:
<223> OTHER INFORMATION: primer

<400> SEQUENCE: 60
gctctaattt gtgagtttag tatacatgca tttacttata atacagtttt tcgaacgcag     60
aattttcgag ttattaaa                                                  78
```

ACETYL-TRANSFERASES

This application is the U.S. national phase of International Application No. PCT/EP2019/087183 filed 30 Dec. 2019, which designated the U.S. and claims priority to CH Patent Application No. 01616/18 filed 31 Dec. 2018, the entire contents of each of which are hereby incorporated by reference.

The present invention is related to production of retinyl acetate generated via enzymatic conversion of retinol, said process including the use of modified enzymes with improved activity.

Retinyl acetate is an important intermediate or precursor for production of retinoids, particularly such as vitamin A. Retinoids, including vitamin A, are one of very important and indispensable nutrient factors for human beings which must be supplied via diet. Retinoids promote well-being of humans, inter alia in respect of vision, the immune system and growth.

Current chemical production methods for retinoids, particularly vitamin A and precursors thereof, have some undesirable characteristics such as e.g. high-energy consumption, complicated purification steps and/or undesirable by-products. Therefore, over the past decades, other approaches to manufacture retinoids, particularly vitamin A and precursors thereof, have been investigated, including microbial conversion steps, which would be more economical as well as ecological.

In general, the biological systems that produce retinoids are industrially intractable and/or produce the compounds at such low levels that its isolation on industrial scale is not practicable of economic interest. There are several reasons for this, including instability of the retinoids in such biological systems or the relatively high production of by-products.

Acetylation of carotenoids, such as e.g. astaxanthin or zeaxanthin, by action of Atf1 from *Saccharomyces bayanus* has been previously reported (WO2014096992), with acetylation of for instance zeaxanthin in the range of up to 90%. However, these acetyl transferase enzymes usually have different substrate specificities for different alcohol substrates, which is determined by the local structural environment of the alcohol function on the molecule that is to be acetylated. For example, the hydroxy group to be acetylated in carotenoids, such as e.g. zeaxanthin, is located on the beta-ionone ring structure, whereas the hydroxy group to be acetylated in retinol is not located on the ionone ring structure but located at the other end on the $CH_2$ carbon at the end of the polyene chain of the molecule. Due to this different local molecular context of the acetylated hydroxy group it is very difficult to make predictions on acetylation of retinols from data on acetylation of carotenoids: as shown in Example 2, use of ATF1 from *S. bayanus* resulted in only about 10% retinyl acetate as compared to up to 90% acetylation with zeaxanthin as substrate.

Surprisingly, we now found that modification of certain amino acids in acetyl transferases, particularly ATF1, can boost acetylation of retinoids, particularly the formation of retinyl acetate, leading to conversion ratios which are increased by at least about 0.2-fold, such as in a range of about 0.2 to about 4× or more compared to the respective wild-type, particularly with retinyl acetate formation in the range of at least about 50 to 90%, based on the total retinoids obtainable by growing the respective host cell on glucose.

Particularly, the present invention is related to a modified enzyme involved in acetylation of retinol into retinyl acetate, particularly fungal enzyme comprising one or more modification(s), such as amino acid substitution(s), in a sequence with at least about 20%, such as 25, 30, 35, 40, 45, 50, 55, 60, 65, 70, 75, 80, 85, 90, 92, 95, 97, 98, 99% or up to 100% identity to SEQ ID NO:1, said one or more amino acid substitution(s) being located at position(s) corresponding to amino acid residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof, in the polypeptide according to SEQ ID NO:1.

The use of such modified enzyme in a process for production of retinoids, wherein said modified enzyme is expressed, particularly heterologous expressed, in a suitable host cell, particularly fungal host cell capable of retinol production, leads to an increase in retinyl acetate in the range of at least about 0.2, 0.3, 0.4, 0.5, 1, 1.2, 1.5, 2, 2.5, 3, 3.5, 4, 4.5, 5, 6, 7, 8, 9, 10, 12, 15, 20, 25× based on total retinoids present in/produced by the modified host cell as compared to a non-modified host cell obtainable in fermentation with glucose as carbon source, such as e.g. in a fed-batch process for 80, 90, 100, 110, 120, 130 h under suitable culture conditions.

Furthermore surprisingly, the expression of said modified acetyl transferases, particular ATF1, in a retinol-producing host cell, particularly fungal host cell, can boost the amount of total retinoids produced by said host cell, with an increase by at least about 1, 2, 3, 4, 5, 6× more total retinoids compared to a host cell cultivated under the same conditions but expressing the corresponding wild-type/non-modified enzymes as defined herein, such as e.g. in fed-batch fermentation using glucose as carbon source, particularly fed-batch of e.g. 80, 90, 100, 110, 120, 130 h under suitable culture conditions.

The terms modified "acetyl transferase", "retinol acetylating enzyme", "enzyme having retinol acetylating activity", "ATF" or "ATF1" are used interchangeably herein and refer to enzymes of EC class [EC 2.3.1.84] which are capable of catalyzing the conversion of retinol into retinyl acetate, with particularly at least about 50 to 90% in the acetylated form based on total retinoids.

Suitable enzymes which can be used to generate the modified ATFs according to the present invention are obtainable from fungal enzymes comprising a highly conserved partial amino acid sequence of at least 7 amino acid residues selected from [NDEHCS]-H-x(3)-D-[GA](motifs are in Prosite syntax, as defined in prosite.expasy.org/scanprosite/scanprosite_doc.html), wherein "x" denotes an arbitrary amino acid and with the central histidine being part of the enzyme's binding pocket, preferably wherein the 7 amino acid motif is selected from [NDE]-H-x(3)-D-[GA], more preferably selected from [ND]-H-x(3)-D-[GA], most preferably selected from N—H-x(3)-D-[GA] corresponding to position N218 to G224 in the polypeptide according to SEQ ID NO:1. Examples of such non-modified enzymes might be selected from yeast, such as Lachancea, *Saccharomyces* or Wickerhamomyces, particularly from *L. mirantina, L. fermentati, S. bayanus,* or *W. anomalus*, such as e.g. LmATF1 according to SEQ ID NO:1, SbATF1 according to SEQ ID NO:5, LfATF1 according to SEQ ID NO:9, LffATF1 according to SEQ ID NO:7, Wa1ATF1 according to SEQ ID NO:11 or Wa3ATF1 according to SEQ ID NO:13.

Modified ATFs as defined herein are capable of converting retinol into retinyl acetate, particularly with conversion ratios of at least about 50%, preferably 52, 55, 60, 65, 70, 75, 80, 85, 90, 92, 95 or even 100% (based on the total amount of retinoids produced by said host cell) towards generation of retinyl acetate, such as e.g. obtainable via expression of a modified LmATF1 under suitable culture conditions including but not limited to cultivation on glucose, galactose or xylose. A preferred modified isoform is ATF1, such as a polypeptide with at least 20% identity to SEQ ID NO:1 comprising one or more amino acid substitution(s) on one or more position(s) as defined herein.

The enzymes as defined herein are used in the conversion of retinol into retinyl acetate, wherein the substrate (i.e. retinol) can be either cis-, trans- or a mix of cis-/trans-retinol in any possible ratio. Preferably, the retinol-mix to be used as substrate has high percentage of trans-retinol, such as e.g. about 65 to 98% of trans-isomer based on total retinols in the host cell. Acetylation of said retinol-mix with about 65 to 98% trans-retinol would lead to retinyl acetate with about the same ratio of trans to cis-retinyl acetate based on total retinyl acetate produced by the host cell.

Thus, the present invention is related to conversion of retinol into retinyl acetate using a suitable host cell as defined herein comprising and expressing a modified enzyme as defined herein, wherein the retinol is a mix of trans- and cis-retinol and wherein the percentage of trans-retinol is in the range of about 65 to 98% trans retinol based on total retinol.

The terms "conversion", "enzymatic conversion", "acetylation" or "enzymatic acetylation" in connection with enzymatic catalysis of retinol are used interchangeably herein and refer to the action of modified ATF, particularly Atf1 enzyme, as defined herein.

The term "conversion ratio" refers to the percentage of acetylated forms, i.e. a ratio of acetylated forms to non-acetylated forms of a compound, particularly the ratio of acetylated forms of retinol, such as retinyl acetate, to non-acetylated retinoids present in the respective host cell, wherein the acetylation is resulting from action of the modified Atf1 enzymes as of the present invention.

Suitable host cells according to the present invention included fungal host cells. As used herein, the term "fungal host cell" particularly includes yeast cells, wherein the cell is a retinol-producing host cells, particularly a retinyl acetate-producing host cell, such as retinyl acetate-producing fungal host cell, including but not limited to *Yarrowia* or *Saccharomyces*, such as e.g. *Yarrowia lipolytica* or *Saccharomyces cerevisiae*.

The modified ATF enzyme might be used in an isolated form (e.g. in a cell-free system) or might be expressed in the suitable host cell, such as e.g. retinol-producing host cell, particularly fungal host cell as defined herein. Enzymes might be expressed as endogenous enzymes or as heterologous enzymes. Preferably, the modified enzymes as described herein are introduced and expressed as heterologous enzymes in a suitable host cell, such as e.g. a retinol-producing host cell, particularly fungal host cell as defined herein.

In one embodiment, the modified Atf1 enzyme as defined herein comprises an amino acid substitution at a position corresponding to residue 68 in the polypeptide according to SEQ ID NO:1 leading to threonine at said residue, such as e.g. via substitution of glutamine by threonine (Q68T). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55 to 70% based on total retinoids present in the host cell. The mutation might furthermore be combined with 1, 2, 3, 4 or more mutation(s) as defined herein, such as particularly with one or more amino acid substitution(s) at position(s) corresponding to residue(s) 69 and/or 407 and/or 409 and/or 480 in the polypeptide according to SEQ ID NO:1.

In one embodiment, the modified Atf1 enzyme as defined herein comprises an amino acid substitution at a position corresponding to residue 69 in the polypeptide according to SEQ ID NO:1 leading to asparagine, serine or alanine at said residue, such as e.g. via substitution of histidine by asparagine (H69N), serine (H69S) or alanine (H69A), with preference for H69A. Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 60 to 84% based on total retinoids present in the host cell. The mutation might furthermore be combined with 1, 2, 3, 4 or more mutation(s) as defined herein, such as particularly with one or more amino acid substitution(s) at position(s) corresponding to residue(s) 72 and/or 311 and/or 334 and/or 407 and/or 409 and/or 480 and/or 484 in the polypeptide according to SEQ ID NO:1.

In another embodiment, the modified Atf1 enzyme as defined herein comprises an amino acid substitution at a position corresponding to residue 72 in the polypeptide according to SEQ ID NO:1 leading to asparagine or lysine at said residue, such as e.g. via substitution of glutamine by asparagine (Q72N) or lysine (Q72K). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55 to 81% based on total retinoids present in the host cell. The mutation might furthermore be combined with 1, 2, 3, 4 or more mutation(s) as defined herein, such as particularly with one or more amino acid substitution(s) at position(s) corresponding to residue(s) 407 and/or 409 and/or 480 in the polypeptide according to SEQ ID NO:1.

In another embodiment, the modified Atf1 enzyme as defined herein comprises an amino acid substitution at a position corresponding to residue 73 in the polypeptide according to SEQ ID NO:1 leading to leucine at said residue, such as e.g. via substitution of isoleucine by leucine (I73L). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 57% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 171 in the polypeptide according to SEQ ID NO:1 leading to lysine or asparagine at said residue, such as e.g. via substitution of glycine by lysine (G171K) or asparagine (G171N). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x (3)-D-[GA] as defined herein, in a fermentation process using a suitable carbon source such as e.g. glucose particularly might lead to conversion ratios of retinol into retinyl acetate in the range of at least about 50%, such as at least about 55 to 59% based on total retinoids present in the host cell. The mutation might furthermore be combined with 1, 2, 3, 4 or more mutation(s) as defined herein.

In one further embodiment, the modified Atf1 enzyme as defined herein comprises an amino acid substitution at a position corresponding to residue 172 in the polypeptide according to SEQ ID NO:1 leading to glycine at said residue, such as e.g. via substitution of asparagine by glycine (N172G). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 53% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 174 in the polypeptide according to SEQ ID NO:1 leading to isoleucine at said residue, such as e.g. via substitution of valine by isoleucine (V174I). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 57% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 176 in the polypeptide according to SEQ ID NO:1 leading to alanine or glycine at said residue, such as e.g. via substitution of serine by alanine (S176A) or glycine (S176G). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55 to 57% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 178 in the polypeptide according to SEQ ID NO:1 leading to valine at said residue, such as e.g. via substitution of leucine by valine (L178V). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 53% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 291 in the polypeptide according to SEQ ID NO:1 leading to serine or glycine at said residue, such as e.g. via substitution of alanine by serine (A291S) or glycine (A291G). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 51 to 52% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 292 in the polypeptide according to SEQ ID NO:1 leading to alanine, serine, or asparagine at said residue, such as e.g. via substitution of glycine by alanine (G292A), serine (G292S) or asparagine (G292N). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 53 to 57% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 294 in the polypeptide according to SEQ ID NO:1 leading to leucine or valine at said residue, such as e.g. via substitution of phenylalanine by leucine (F294L) or valine (F294V). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 54 to 58% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 301 in the polypeptide according to SEQ ID NO:1 leading to phenylalanine at said residue, such as e.g. via substitution of tyrosine by phenylalanine (Y301F). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 56% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 307 in the polypeptide according to SEQ ID NO:1 leading to isoleucine at said residue, such as e.g. via substitution of proline by isoleucine (P307I). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55% based on total retinoids present in the host cell. The mutation might furthermore be combined with 1, 2, 3, 4 or more mutation(s) as defined herein.

According to one embodiment, the modified Atf1 enzyme as defined herein comprises an amino acid substitution at a position corresponding to residue 308 in the polypeptide according to SEQ ID NO:1 leading to valine at said residue, such as e.g. via substitution of threonine by valine (T308V). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 56% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 311 in the polypeptide according to SEQ ID NO:1 leading to methionine or isoleucine at said residue, such as e.g. via substitution of threonine by methionine (T311M) or isoleucine (T311I). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55 to 82% based on total retinoids present in the host cell. The mutation might furthermore be combined with 1, 2, 3, 4 or more mutation(s) as defined herein, such as particularly with one or more amino acid substitution(s) at position(s) corresponding to residue(s) 407 and/or 409 and/or 480 in the polypeptide according to SEQ ID NO:1.

In another embodiment, the modified Atf1 enzyme as defined herein comprises an amino acid substitution at a position corresponding to residue 312 in the polypeptide according to SEQ ID NO:1 leading to alanine at said residue, such as e.g. via substitution of serine by alanine (S312A). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 54% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 320 in the polypeptide according to SEQ ID NO:1 leading to asparagine at said residue, such as e.g. via substitution of histidine by asparagine (H320N). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 57% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 322 in the polypeptide according to SEQ ID NO:1 leading to valine or phenylalanine at said residue, such as e.g. via substitution of tyrosine by valine (Y322V) or phenylalanine (Y322F). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 56 to 57% based on total retinoids present in the host cell. The mutation might furthermore be combined with 1, 2, 3, 4 or more mutation(s) as defined herein.

In one particular embodiment, the modified Atf1 enzyme as defined herein comprises an amino acid substitution at a position corresponding to residue 334 in the polypeptide according to SEQ ID NO:1 leading to leucine at said residue, such as e.g. via substitution of valine by leucine (V334L). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 63 to 78% based on total retinoids present in the host cell. The mutation might furthermore be combined with 1, 2, 3, 4 or more mutation(s) as defined herein, such as particularly with one or more amino acid substitution(s) at position(s) corresponding to residue(s) 407 and/or 409 and/or 480 in the polypeptide according to SEQ ID NO:1.

In another embodiment, the modified Atf1 enzyme as defined herein comprises an amino acid substitution at a position corresponding to residue 362 in the polypeptide according to SEQ ID NO:1 leading to alanine at said residue, such as e.g. via substitution of serine by alanine (S362A). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 54% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 405 in the polypeptide according to SEQ ID NO:1 leading to alanine at said residue, such as e.g. via substitution of serine by alanine (S405A). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 61% based on total retinoids present in the host cell. The mutation might furthermore be combined with 1, 2, 3, 4 or more mutation(s) as defined herein.

In one particular embodiment, the modified Atf1 enzyme as defined herein comprises an amino acid substitution at a position corresponding to residue 407 in the polypeptide according to SEQ ID NO:1 leading to isoleucine at said residue, such as e.g. via substitution of valine by isoleucine (V407I). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 56 to 84% based on total retinoids present in the host cell. The mutation might furthermore be combined with 1, 2, 3, 4 or more mutation(s) as defined herein, such as particularly with one or more amino acid substitution(s) at position(s) corresponding to residue(s) 409 and/or 480 and/or 484 in the polypeptide according to SEQ ID NO:1.

In one preferred embodiment, the modified Atf1 enzyme as defined herein comprises an amino acid substitution at a position corresponding to residue 409 in the polypeptide according to SEQ ID NO:1 leading to alanine at said residue, such as e.g. via substitution of glycine by alanine (G409A). Said modified enzyme might be originated from yeast, such as e.g. *L. mirantina, L. fermentati, W. anomalus* or *S. bayanus*, preferably from *L. mirantina* or *W. anomalus*. Using such modified enzyme comprising said mutation together with the 7 amino acid motif according to N—H-x (3)-D-[GA] as defined herein, in a fermentation process using a suitable carbon source such as e.g. glucose particularly might lead to conversion ratios of retinol into retinyl acetate in the range of at least about 50%, such as at least about 63 to 84% based on total retinoids present in the host cell. Compared to the respective process using the corresponding non-modified ATF1 enzyme, an increase in the percentage of retinyl acetate based on total retinoids the range of at least about 20, 30, 40, 50, 70, 100, 200, 300% or more can be obtained. The mutation might furthermore be combined with 1, 2, 3, 4 or more mutation(s) as defined herein, such as particularly with one or more amino acid substitution(s) at position(s) corresponding to residue(s) 480 and/or 484 in the polypeptide according to SEQ ID NO:1.

According to another preferred embodiment, the modified Atf1 enzyme as defined herein comprises an amino acid substitution at a position corresponding to residue 480 in the polypeptide according to SEQ ID NO:1 leading to glutamic acid, leucine, methionine, phenylalanine or glutamine at said residue, such as e.g. via substitution of serine by glutamic acid (S480E), leucine (S480L), methionine (S480M), phenylalanine (S480F) or glutamine (S480Q). Said modified enzyme might be originated from yeast, such as e.g. *L. mirantina, L. fermentati, W. anomalus* or *S. bayanus*, preferably from *L. mirantina* or *W. anomalus*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 52 to 84% based on total retinoids present in the host cell. Compared to the respective process using the corresponding non-modified ATF1 enzyme, an increase in the percentage of retinyl acetate based on total retinoids in the range of at least about 20, 30, 40, 50, 60, 70% or more can be obtained. The mutation might furthermore be combined with 1, 2, 3, 4 or more mutation(s) as defined herein, such as particularly with at least an amino acid substitution at position corresponding to residue 484 in the polypeptide according to SEQ ID NO:1.

According to another embodiment, the modified Atf1 enzyme as defined herein comprises an amino acid substitution at a position corresponding to residue 483 in the polypeptide according to SEQ ID NO:1 leading to valine at said residue, such as e.g. via substitution of leucine by valine (L483V). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55% based on total retinoids present in the host cell. The mutation might furthermore be combined with 1, 2, 3, 4 or more mutation(s) as defined herein.

According to another embodiment, the modified Atf1 enzyme as defined herein comprises an amino acid substitution at a position corresponding to residue 484 in the polypeptide according to SEQ ID NO:1 leading to leucine at said residue, such as e.g. via substitution of isoleucine by leucine (I484L). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x (3)-D-[GA] as defined herein, in a fermentation process using a suitable carbon source such as e.g. glucose particularly might lead to conversion ratios of retinol into retinyl acetate in the range of at least about 50%, such as at least about 58 to 84% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 490 in the polypeptide according to SEQ ID NO:1 leading to isoleucine at said residue, such as e.g. via substitution of valine by isoleucine (V490I). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 56% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 492 in the polypeptide according to SEQ ID NO:1 leading to valine at said residue, such as e.g. via substitution of aspartic acid by valine (D492V). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 54% based on the total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 520 in the polypeptide according to SEQ ID NO:1 leading to alanine at said residue, such as e.g. via substitution of isoleucine by alanine (I520A). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 54% based on total retinoids present in the host cell. The mutation might furthermore be combined with 1, 2, 3, 4 or more mutation(s) as defined herein.

In another embodiment, the modified Atf1 enzyme as defined herein comprises an amino acid substitution at a position corresponding to residue 521 in the polypeptide according to SEQ ID NO:1 leading to alanine or valine at said residue, such as e.g. via substitution of cysteine y alanine (C521A) or valine (C521V). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 54 to 58% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 522 in the polypeptide according to SEQ ID NO:1 leading to being serine or threonine at said residue, such as e.g. via substitution of alanine by serine (A522S) or threonine (A522T). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55 to 59% based on total retinoids present in the host cell. The mutation might furthermore be combined with 1, 2, 3, 4 or more mutation(s) as defined herein.

In one embodiment, the modified Atf1 enzyme as defined herein comprises an amino acid substitution at a position corresponding to residue 524 in the polypeptide according to SEQ ID NO:1 leading to asparagine or serine at said residue, such as e.g. via substitution of aspartic acid by asparagine (D524N) or serine (D524S). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 52 to 58% based on total retinoids present in the host cell. The mutation might furthermore be combined with 1, 2, 3, 4 or more mutation(s) as defined herein.

According to another embodiment, the modified Atf1 enzyme as defined herein comprises an amino acid substitution at a position corresponding to residue 525 in the polypeptide according to SEQ ID NO:1 leading to valine, isoleucine or arginine at said residue, such as e.g. via substitution of glutamine by valine (Q525V), isoleucine (Q525I) or arginine (Q525R). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 56 to 67% based on total retinoids present in the host cell. The mutation might furthermore be combined with 1, 2, 3, 4 or more mutation(s) as defined herein.

In one further embodiment, the modified Atf1 enzyme as defined herein comprises an amino acid substitution at a position corresponding to residue 526 in the polypeptide according to SEQ ID NO:1 leading to serine at said residue, such as e.g. via substitution of glycine by serine (G526S). Said modified enzyme might be originated from yeast, such as e.g. *L. mirantina, L. fermentati, W. anomalus* or *S. bayanus*, preferably from *L. mirantina*. Using such modified enzyme comprising said mutation together with the 7 amino acid motif according to N—H-x(3)-D-[GA] as defined herein, in a fermentation process using a suitable carbon source such as e.g. glucose particularly might lead to conversion ratios of retinol into retinyl acetate in the range of at least about 50%, such as at least about 55% based on total retinoids present in the host cell. The mutation might furthermore be combined with 1, 2, 3, 4 or more mutation(s) as defined herein.

Particularly useful for the purpose of the present invention are modified Atf1 enzymes as defined herein comprising a combination of at least 2 mutations, i.e. combination of at least 2 amino acid substitutions at positions corresponding to residues G409A with S480L or S480Q, G409A with Q72K, G409A with V334L, G409A with T311I, G409A with H69N, H69S or H69A, G409A with V407I in the polypeptide according to SEQ ID NO:1, together with the 7 amino acid motif according to N—H-x(3)-D-[GA] as defined herein, to be used in a fermentation process using a suitable carbon source such as e.g. glucose and particularly leading to conversion ratios of retinol into retinyl acetate in the range of at least about 50%, such as at least about 52 to 74% based on total retinoids present in the host cell, or combination of at least 2 amino acid substitutions at positions corresponding to residues V407I with T311I, V407I with H69N, H69A or H69S, V407I with S480L or S480Q, V407I with I484L, V407I with V334L, or V407I with Q72K the polypeptide according to SEQ ID NO:1 or combination of at least 2 amino acid substitutions at positions corresponding to residues S480Q with T311I, S480Q with Q72K, S480Q with H69N, H69S, H69A, S480Q with Q68T, S480Q with I484I, or S480Q with V334L in the polypeptide according to SEQ ID NO:1.

Preferred are furthermore combination of at least 3 mutations, i.e. combination of at least 3 amino acid substitution(s) at position(s) corresponding to residues S480Q V407I I484L, S480Q V407I V334L, S480Q G409A Q68T, S480Q V407I H69N, S480Q V407I Q72K, S480Q V407I H69S, S480Q G409A H69A, S480Q G409A H69N, S480Q G409A I484L, S480Q V407I Q68T, S480Q V407I H69A, S480Q V407I T311I, G409A V407I H69S, G409A V407I S480L, G409A V407I Q68T, G409A V407I Q72K, G409A V407I I484L, G409A V407I H69A, G409A V407I H69N, G409A V407I T311I, or G409A V407I V334L in the polypeptide according to SEQ ID NO:1, together with the 7 amino acid motif according to N—H-x(3)-D-[GA] as defined herein, to be used in a fermentation process using a suitable carbon source such as e.g. glucose and particularly leading to conversion ratios of retinol into retinyl acetate in the range of at least about 50%, such as at least about 58 to 71% based on total retinoids present in the host cell.

In another embodiment, combinations of at least 4 mutations, i.e. combination of at least 4 amino acid substitutions at positions corresponding to residues S480Q G409A V407I I484L, S480Q G409A V407I Q72K, S480Q G409A V407I Q68T, S480L G409A V407I T311I, S480Q G409A V407I I484L, S480Q G409A V407I H69N, S480Q G409A V407I H69A, S480Q G409A V407I T311I, S480Q G409A V407I H69S, or S480Q G409A V407I V334L in the polypeptide according to SEQ ID NO:1, together with the 7 amino acid motif according to N—H-x(3)-D-[GA] as defined herein, to be used in a fermentation process using a suitable carbon source such as e.g. glucose and particularly leading to conversion ratios of retinol into retinyl acetate in the range of at least about 50%, such as at least about 57 to 78% based on total retinoids present in the host cell.

In even a further embodiment, modified enzymes are preferred comprising combinations of at least 5 mutations, i.e. combinations of at least 5 amino acid substitutions at positions corresponding to residues S480Q G409A V407I H69S Q72K, S480Q G409A V407I H69N T311I, S480Q G409A V407I H69N Q72K, S480Q G409A V407I H69A Q68T, S480Q G409A V407I H69N V334L, S480Q G409A V407I H69N I484L, S480Q G409A V407I H69A V334L, S480Q G409A V407I H69A Q72K, S480Q G409A V407I H69A T311I, or S480Q G409A V407I H69A I484L in the polypeptide according to SEQ ID NO:1, together with the 7 amino acid motif according to N—H-x(3)-D-[GA] as defined herein, to be used in a fermentation process using a suitable carbon source such as e.g. glucose and particularly leading to conversion ratios of retinol into retinyl acetate in the range of at least about 50%, such as at least about 56 to 84% based on total retinoids present in the host cell.

The host cell as described herein is capable of conversion of retinol into retinyl acetate with conversion ratios which are increased by at least about 0.2-fold, such as in a range of about 0.2 to about 4× or more compared to conversion via the respective wild-type enzyme, particularly with conversion ratios of at least about 50%, preferably 52, 55, 60, 65, 70, 75, 80, 85, 90, 92, 95 or even 100%, such as in a range of about 50-90%, (based on the total amount of retinoids produced by said host cell) towards generation of retinyl acetate, such as e.g. obtainable via expression of a modified LmATF1 under suitable culture conditions including but not limited to cultivation on glucose, galactose or xylose and a suitable host cell, such as e.g. selected from a fungal host cell including *Yarrowia* or *Saccharomyces*. Suitable conditions might be cultivation in a fed-batch fermentation of e.g. 80, 90, 100, 110, 120, 130 h.

A modified host cell as defined herein comprises one or more copies of modified ATFs as defined herein, preferably wherein the ATFs are heterologous expressed in said modified host cell. Modifications in order to have the host cell as defined herein produce more copies of genes and/or proteins, such as e.g. more copies of modified ATFs with selectivity towards formation of retinyl acetate as defined herein, including conversion ratios of at least about 50%, such as in a range of about 50-90%, based on the total amount of retinoids produced by said host cell towards generation of retinyl acetate, such as e.g. obtainable via expression of a modified LmATF1 under suitable culture conditions including but not limited to cultivation on glucose, galactose or xylose, may include the use of strong promoters, suitable transcriptional- and/or translational enhancers, or the introduction of one or more gene copies into the retinol-producing host cell, particularly fungal host cell, leading to increased accumulation of the respective enzymes in a given time. The skilled person knows which techniques to use depending on the host cell. The increase or reduction of gene expression can be measured by various methods, such as e.g. Northern, Southern or Western blot technology as known in the art.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

Thus, the present invention is directed to a retinol-producing host cell, particularly fungal host cell, as described herein comprising an expression vector or a polynucleotide encoding modified ATFs, particularly Atf1 enzymes, as described herein which has been integrated in the chromosomal DNA of the host cell. Such retinol-producing host cell, particularly fungal host cell, comprising a heterologous polynucleotide either on an expression vector or integrated into the chromosomal DNA encoding modified ATFs, particularly Atf1 enzymes, as described herein is called a recombinant or modified host cell. The retinol-producing host cell, particularly fungal host cell, might contain one or more copies of a gene encoding the modified ATFs, particularly Atf1 enzymes, as defined herein, such as e.g. polynucleotides encoding polypeptides with at least about 20% identity to SEQ ID NOs:1 comprising one or more amino acid substitution(s) as defined herein, together with the 7 amino acid motif as defined herein, leading to overexpression of such genes encoding said modified ATFs, particularly Atf1 enzymes, as defined herein. The increase of gene expression can be measured by various methods, such as e.g. Northern, Southern or Western blot technology as known in the art.

Based on the sequences as disclosed herein including the 7 amino acid motif and on the preference for acetylation of retinol (preferably in the trans-isoform), into retinyl acetate (preferably in the trans-isoform), particularly with conversion ratios of at least about 50%, preferably 52, 55, 60, 65, 70, 75, 80, 85, 90, 92, 95 or even 100%, such as in a range of about 50-90%, (based on the total amount of retinoids produced by said host cell) towards generation of retinyl acetate, such as e.g. obtainable via expression of a modified LmATF1 under suitable culture conditions including but not limited to cultivation on glucose, galactose or xylose, one could easily deduce further suitable genes encoding polypeptides having retinol acetylating activity as defined herein which could be used for the conversion of retinol into retinyl acetate.

Thus, the present invention is directed to a method for identification of novel acetylating enzymes, wherein a polypeptide comprising a partial amino acid sequence of at least 7 amino acid residues selected from [NDEHCS]-H-x(3)-D-[GA] corresponding to position N218 to G224 in the polypeptide according to SEQ ID NO:1 (motif in Prosite syntax), e.g. such as a polypeptide with at least 20%, such as e.g. 25, 30, 35, 40, 45, 50, 55, 60, 65, 70, 75, 80, 85, 90, 92, 95, 97, 98, 99% or up to 100% identity to known sequences, such as SEQ ID NOs:1, is used as a probe in a screening process for new AFT enzymes, particular Atf1 enzymes, with preference for production of retinyl acetate, from conversion of retinol, which could be used for introduction of one or more amino acid substitution(s) as disclosed herein to generate modified Atf1 enzymes with conversion rates which are increased by at least about 0.2-fold, such as in a range of about 0.2 to about 4× or more compared to the respective wild-type Atf1-enzymes, such as particularly conversion ratios of at least about 50%, preferably 52, 55, 60, 65, 70, 75, 80, 85, 90, 92, 95 or even 100%, such as in a range of about 50-90%, (based on the total amount of retinoids produced by said host cell) towards generation of retinyl acetate, such as e.g. obtainable via expression of a modified LmATF1 under suitable culture conditions including but not limited to cultivation on glucose, galactose or xylose. This method is particularly useful for detection of putative fungal, including yeast, ATF1-homologs, characterized by the 7 amino acid motif with the central histidine being part of the enzyme's binding pocket but only show low sequence identity, such as at least about 20-35% longest identity according to the NEEDLE protocol as described below).

In one embodiment, the present invention is directed to a process for identification of modified ATF1 enzymes, preferably membrane-associated yeast ATF1 enzymes, comprising a partial amino acid sequence of at least 7 amino acid residues [NDEHCS]-H-x(3)-D-[GA] corresponding to position N218 to G224 in the polypeptide according to SEQ ID NO:1 (motif in Prosite syntax) and as defined herein, said process comprising the steps of:

(1) alignment of different membrane-associated yeast ATF enzymes, including but not limited to enzymes originated from *Lachancea, Wickerhamomyces* or *Saccharomyces*, such as e.g. identified via BLAST search against UNIREF/UNIPROT databases, with SEQ ID NO:1

(2) identify the corresponding positions in the ATF homologs, (3) introduction of one or more amino acid substitution(s) on position(s) corresponding to amino acid residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof in a polypeptide according to SEQ ID NO:1; and (4) screening for retinol acetylation activity in a retinol-producing host cell, preferably selected from *Yarrowia* or *Saccharomyces*, with preferred conversion rates of at least about 50-90% based on the total amount of retinoids produced by said host cell towards formation of retinyl acetate.

The present invention is particularly directed to the use of such novel modified ATFs, particularly Atf1 enzymes, in a process for production of retinyl acetate, wherein the production of retinyl esters, such as e.g. retinol long-chain (LC)-acyl, is reduced. The process might be performed with a suitable retinol-producing host cell, particularly fungal host cell, expressing said modified ATF, particularly Atf1 enzyme, preferably wherein the genes encoding said modified enzymes are heterologous expressed, i.e. introduced into said host cells. Retinyl acetate can be further converted into vitamin A by the action of (known) suitable chemical or biotechnological mechanisms.

Thus, the present invention is particularly directed to a process for production of a retinoid mix comprising retinyl acetate in a percentage of at least about 50-90% based on the total amount of retinoids produced by the host cell, such as e.g. obtainable via expression of a modified LmATF1 under suitable culture conditions including but not limited to cultivation on glucose, galactose or xylose—or at least wherein the percentage of retinyl acetate is increased by at least about 0.2-fold, such as in a range of about 0.2 to about 4× or more compared to the use of the respective non-modified Atf1 enzyme, including e.g. a percentage of at least 65% as trans-retinyl acetate, via enzymatic activity of a modified Atf1 enzyme as defined herein, comprising contacting retinol, such as e.g. a retinol mix comprising trans- and cis-retinol and preferably with a percentage of at least 65 to 90% in the form of trans-retinol, with said modified Atf1 enzyme, and optionally isolating and/or purifying the formed retinyl acetate from the host cell. Particularly, the invention is directed to a process for production of vitamin A, said process comprising (a) introducing a nucleic acid molecule encoding one of the modified Atf1 enzymes as defined herein into a suitable retinol-producing host cell, particularly fungal host cell, as defined herein, (b) enzymatic conversion, i.e. acetylation, of retinol, such as e.g. a retinol-mix comprising at least about 65-90% retinol as trans-retinol, via action of said expressed modified Atf1 into preferably at least about 50% of retinyl acetate, and (3) conversion of said retinyl acetate into vitamin A under suitable conditions known to the skilled person.

The terms "sequence identity", "% identity" are used interchangeable herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity.

The modified ATFs, particularly Atf1 enzymes, as defined herein also encompass enzymes carrying further amino acid substitution(s) which do not alter enzyme activity, i.e. which show the same properties with respect to the enzymes defined herein and catalyze the conversion of retinol to retinyl acetate with conversion ratios of preferably at least 50% based on the total amount of retinoids. Such mutations are also called "silent mutations", which do not alter the (enzymatic) activity of the enzymes according to the present invention.

Expression of the enzymes/polynucleotides encoding one of the specific ATFs, particularly Atf1 enzymes, as defined herein can be achieved in any host system, including (micro) organisms, which is suitable for retinoid (including retinol) production and which allows expression of the nucleic acids encoding one of the enzymes as disclosed herein, including functional equivalents or derivatives as described herein. Examples of suitable retinol-producing host (micro)organisms are bacteria, algae, fungi, including yeasts, plant or animal cells. Preferred bacteria are those of the genera *Escherichia*, such as, for example, *Escherichia coli*, *Streptomyces*, *Pantoea* (*Erwinia*), *Bacillus*, *Flavobacterium*, *Synechococcus*, *Lactobacillus*, *Corynebacterium*, *Micrococcus*, *Mixococcus*, *Brevibacterium*, *Bradyrhizobium*, *Gordonia*, *Dietzia*, *Muricauda*, *Sphingomonas*, *Synochocystis*, *Paracoccus*, such as, for example, *Paracoccus zeaxanthinifaciens*. Preferred eukaryotic microorganisms, in particular fungi including yeast, are selected from *Saccharomyces*, such as *Saccharomyces cerevisiae*, *Aspergillus*, such as *Aspergillus niger*, *Pichia*, such as *Pichia pastoris*, *Hansenula*, such as *Hansenula polymorpha*, *Kluyveromyces*, such as *Kluyveromyces lactis*, *Phycomyces*, such as *Phycomyces blakesleanus*, *Mucor*, *Rhodotorula*, *Sporobolomyces*, *Xanthophyllomyces*, *Phaffia*, *Blakeslea*, such as e.g. Blakeslea trispora, or *Yarrowia*, such as *Yarrowia lipolytica*. In particularly preferred is expression in a fungal host cell, such as e.g. *Yarrowia* or *Saccharomyces*, or expression in *Escherichia*, more preferably expression in *Yarrowia lipolytica* or *Saccharomyces cerevisiae*.

Depending on the host cell the polynucleotides as defined herein for acetylation of retinol might be optimized for expression in the respective host cell. The skilled person knows how to generate such further modified polynucleotides. It is understood that the polynucleotides as defined herein also encompass such host-optimized nucleic acid molecules as long as they still express the polypeptide with the respective activities as defined herein.

Thus, in one embodiment, the present invention is directed to a retinol-producing host cell, particularly fungal host cell, comprising polynucleotides encoding ATFs, in particular Atf1 enzymes, as defined herein which are optimized for expression in said host cell. Particularly, a retinol-producing host cell, particularly fungal host cell, is selected from yeast, e.g. *Yarrowia* or *Saccharomyces*, such as e.g. *Saccharomyces cerevisiae* or *Yarrowia lipolytica*, wherein the polynucleotides encoding the ATFs, particularly Atf1 enzymes, as defined herein are selected from polynucleotides expressing modified polypeptides comprising one or more amino acid substitution(s) in a sequence with at least 20%, such as e.g. 25, 30, 35, 40, 45, 50, 55, 60, 65, 70, 75, 80, 85, 90, 92, 95, 97, 98, 99% or up to 100% identity to SEQ ID NO:1, such as e.g. introduction of one or more amino acid substitution(s) at position(s) corresponding to residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526, and combinations thereof and as defined herein and preferably comprising a highly conserved partial amino acid sequence, i.e. common active site or "Prosite-motif", of at least 7 amino acid residues selected from [NDEHCS]-H-x(3)-D-[GA] corresponding to position N218 to G224 in the polypeptide according to SEQ ID NO:1 (motifs are in Prosite syntax, as defined in prosite.expasy.org/scanprosite/scanprosite_doc.html) and wherein "x" denotes an arbitrary amino acid. Preferably, the Prosite-motif is selected from [NDE]-H-x(3)-D-[GA], more preferably selected from [ND]-H-x(3)-D-[GA], most preferably selected from N—H-x(3)-D-[GA] corresponding to position N218 to G224 in the polypeptide according to SEQ ID NO:1; said host cell producing retinyl acetate with a percentage in the range of preferably about 50 to 90% based on the total amount of retinoids produced by said host cell, such as e.g. obtainable via expression of a modified LmATF1 under suitable culture conditions including but not limited to cultivation on glucose, galactose or xylose.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code). Thus, for example, strain Lachancea mirantina is a synonym of strain *Zygosaccharomyces* sp. IFO 11066, originated from Japan.

The present invention is directed to a process for production of retinyl acetate, wherein the retinyl acetate is generated via acetylation of retinol (particularly at least 65% as trans-retinol) as disclosed herein by the action of modified ATF, particularly Atf1 enzymes, as described herein, wherein the acetylating enzymes are preferably heterologous expressed in a suitable host cell under suitable conditions as described herein. The produced retinyl acetate might be isolated and optionally further purified from the medium and/or host cell. Said acetylated retinoids defined herein can be used as building blocks in a multi-step process leading to vitamin A. Vitamin A might be isolated and optionally further purified from the medium and/or host cell as known in the art.

Preferably, acetylation of retinol by the use of ATFs, particularly Atf1 enzymes, as described herein, leads to conversion ratios in the range of about 50 to 90%, i.e. percentage in the range of about 50 to 90% of acetylated retinoids, i.e. retinyl acetate, present in the retinoid mix produced by the host cell, such as e.g. obtainable via expression of a modified LmATF1 under suitable culture conditions including but not limited to cultivation on glucose, galactose or xylose. In a more preferred embodiment, a retinol mix with a percentage of at least about 65% trans-retinol is used as substrate for acetylation via the modified enzymes as defined herein.

Compared to a process using a non-modified ATF1 as defined herein, the percentage of acetylated retinoids, such as retinyl acetate, can be increased by at least about 0.2-fold, such as in a range of about 0.2 to about 4× or more using a retinol-producing host cell comprising/expressing one of the modified ATF1-enzymes as defined herein. Preferably, the host cell might be a fungal host cell, such as e.g. selected from *Yarrowia* or *Saccharomyces*.

The host cell, i.e. microorganism, algae, fungal, animal or plant cell, capable of producing retinol, might furthermore be capable of production of beta-carotene, which might be furthermore enzymatically converted into retinal which might be furthermore converted into retinol. The skilled person knows which genes to be used/expressed for either biosynthesis of beta-carotene and/or bio-conversion of beta-carotene into retinol. Such host cell further being capable of expressing the modified ATF genes, particularly ATF1 genes, as defined herein, and/or further genes required for biosynthesis of vitamin A, may be cultured in an aqueous medium supplemented with appropriate nutrients under aerobic or anaerobic conditions and as known by the skilled person for the respective retinol-producing host cells. Optionally, such cultivation is in the presence of proteins and/or co-factors involved in transfer of electrons, as known in the art. Suitable carbon sources for the purpose of the present invention might be selected from glucose, fructose, raffinose, lactose, galactose, glycerol, xylose, arabinose, sucrose or maltose, particularly selected from glucose, galactose or xylose. The cultivation/growth of the host cell may be conducted in batch, fed-batch, semi-continuous or continuous mode, particularly in fed-batch mode for 80, 90, 100, 110, 120, 130 h under suitable culture conditions. Depending on the host cell, preferably, production of retinoids such as e.g. vitamin A, precursors and/or derivatives thereof such as retinal, retinol, retinyl esters, particularly retinyl acetate, can vary, as it is known to the skilled person. Cultivation and isolation of beta-carotene and retinoid-producing host cells selected from *Yarrowia* and *Saccharomyces* is described in e.g. WO2008042338. With regards to production of beta-carotene and retinoids in host cells selected from *E. coli*, methods are described in e.g. US20070166782.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in μmol substrate consumed or product formed per min per mg of protein. Typically, μmol/min is abbreviated by U (=unit). Therefore, the unit definitions for specific activity of μmol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity, Analytical methods to evaluate the capability of a suitable ATF, particularly Atf1, as defined herein for retinyl acetate production, from conversion of retinol are known in the art, such as e.g. described in Example 4 of WO2014096992. In brief, titers of products such as retinyl acetate, retinol, trans-retinal, cis-retinal, beta-carotene and the like can be measured by HPLC.

With regards to suitable host cells comprising specific enzymes involved in biosynthesis of beta-carotene and that are expressed and active in vivo leading to production of carotenoids, e.g. beta-carotene, both genes and methods to generate carotenoid-producing host cells are known in the art, see e.g. WO2006102342. Depending on the carotenoid to be produced, different genes might be involved.

As used herein, a "retinol-producing host cell" is a host cell, wherein the respective polypeptides are expressed and active in vivo, leading to production of retinoids, e.g. vitamin A and its precursors including retinol, via enzymatic conversion of beta-carotene via retinal into retinol. These polypeptides include the modified ATFs as defined herein. The genes of the vitamin A pathway and methods to generate retinoid-producing host cells are known in the art. The term retinoid includes retinol, which is used as a substrate for the modified acetylating enzymes as defined herein.

Retinoids as used herein include beta-carotene cleavage products also known as apocarotenoids, including but not limited to retinal, retinolic acid, retinol, retinoic methoxide, retinyl acetate, retinyl esters, 4-keto-retinoids, 3 hydroxy-retinoids or combinations thereof. Long chain retinyl esters as used herein are defined as hydrocarbon esters of retinol with fatty acids, where the fatty acids consist of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. The fatty acids in the long chain retinyl esters include but are not limited to linoleic acid, oleic acid or palmitic acid. Biosynthesis of retinoids is described in e.g. WO2008042338.

"Retinal" as used herein is known under IUPAC name (2E,4E,6E,8E)-3,7-Dimethyl-9-(2,6,6-trimethylcyclohexen-1-yl)nona-2,4,6,8-tetraenal. It is herein interchangeably referred to as retinaldehyde or vitamin A aldehyde and includes both cis- and trans-isoforms, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

"Vitamin A" as used herein may be any chemical form of vitamin A found in aqueous solutions, in solids and formulations, and includes retinol, retinyl acetate and retinyl esters. It also includes retinoic acid, such as for instance undissociated, in its free acid form or dissociated as an anion.

Particularly, the present invention features the following embodiments:

(1) A retinol-acetylating enzyme, preferably fungal enzyme, including yeast enzyme, comprising one or more amino acid substitution(s) in a sequence with at least about 20%, such as 25, 30, 35, 40, 45, 50, 55, 60, 65, 70, 75, 80, 85, 90, 92, 95, 97, 98, 99% or up to 100% identity to SEQ ID NO:1, wherein the one or more amino acid substitution(s) are located at position(s) corresponding to amino acid residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof, in the polypeptide according to SEQ ID NO:1, preferably comprising one or more amino acids selected from the group consisting of residue 68 being threonine, residue 69 being asparagine, serine or adenine, residue 72 being asparagine or lysine, residue 73 being leucine, residue 171 being lysine or asparagine, residue 172 being glycine, residue 174 being isoleucine, residue 176 being alanine or glycine, residue 178 being valine, residue 291 being serine or glycine, residue 292 being alanine, serine or asparagine, residue 294 being leucine or valine, residue 301 being phenylalanine, residue 307 being isoleucine, residue 308 being valine, residue 311 being methionine or isoleucine, residue 312 being alanine, residue 320 being asparagine, residue 322 being valine or phenylalanine, residue 334 being leucine, residue 362 being alanine, residue 405 being alanine residue 407 being isoleucine, residue 409 being alanine, residue 480 being glutamic acid, leucine methionine, phenylalanine or glutamine, residue 483 being valine, residue 484 being leucine, residue 490 being isoleucine, residue 492 being valine, residue 520 being alanine, residue 521 being alanine or valine, residue 522 being serine or threonine, residue 524 being asparagine or serine, residue 525 being valine, isoleucine or arginine, residue 526 being serine, and combinations thereof in the polypeptide according to SEQ ID NO:1.

(2) A retinol-acetylating enzyme as of (1) and as defined herein, comprising a highly conserved partial amino acid sequence of at least 7 amino acid residues selected from [NDEHCS]-H-x(3)-D-[GA] corresponding to position N218 to G224 in the polypeptide according to SEQ ID NO:1, with the motif in Prosite syntax and wherein "x" denotes an arbitrary amino acid.

(3) A retinol-acetylating enzyme as of (1) and/or (2) and as defined herein, catalyzing the conversion of retinol into retinyl acetate with a conversion ratio in the range of at least about 50 to about 90%.

(4) A retinol-acetylating enzyme as of (1) and/or (2) and/or (3) and as defined herein, wherein the activity towards conversion or acetylation of retinol into retinyl acetate is increased by at least about 20% compared to a retinol-acetylating enzyme without carrying one or more of said amino acid substitution(s).

(5) A retinol-acetylating enzyme as of (1) and/or (2) and/or (3) and/or (4) and as defined herein, wherein the activity towards production of total retinoids is increased by at least about 2× compared to a retinol-acetylating enzyme without carrying one of more of said amino acid substitution(s).

(6) A retinol-acetylating enzyme as of (1) and/or (2) and/or (3) and/or (4) and/or (5) and as defined herein, comprising a single amino acid substitution located at a position corresponding to amino acid residues selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, and 526, preferably selected from the group consisting of position 69, 72, 334, 405, 407, 409, 480, 484, 525 and 526, in the polypeptide according to SEQ ID NO:1.

(7) A retinol-acetylating enzyme as of (1) and/or (2) and/or (3) and/or (4) and/or (5) and/or (6) and as defined herein, comprising at least two amino acid substitutions at positions corresponding to amino acid residues selected from 480 and 409, 480 and 407 or 407 and 409 in the polypeptide according to SEQ ID NO:1.

(8) A retinol-acetylating enzyme as of (7) and as defined herein, further comprising one or more amino acid substitution(s) at position(s) corresponding to amino acid residue(s) selected from the group consisting of position 68, 69, 72, 311, 334, 484, and combinations thereof in a polypeptide according to SEQ ID NO:1.

(9) A retinol-acetylating enzyme as of (1) and/or (2) and/or (3) and/or (4) and/or (5) and/or (6) and/or (7) and/or (8) and as defined herein, wherein the residue corresponding to position 480 is leucine or glutamine, the residue corresponding to position 409 is alanine, the residue corresponding to position 407 is isoleucine, the residue on position 69 is alanine, asparagine or serine, and optionally further comprising lysine on position 72 and/or isoleucine on position 311 and/or threonine on position 68 and/or leucine on position 334 and/or leucine on position 484.

(10) A retinol-acetylating enzyme as of (1) and/or (2) and/or (3) and/or (4) and/or (5) and/or (6) and/or (7) and/or (8) and/or (9) and as defined herein, which is expressed in a retinol-producing host cell, preferably a fungal host cell, more preferably selected from Yarrowia or Saccharomyces.

(11) A retinol-producing host cell, particularly fungal host cell, comprising an enzyme as of (1) and/or (2) and/or (3) and/or (4) and/or (5) and/or (6) and/or (7) and/or (8) and/or (9) and/or (10) and as defined herein, wherein said host cell being preferably selected from *Yarrowia* or *Saccharomyces*, which preferably has been transformed with a retinol-acetylating enzyme as of (1) and/or (2) and/or (3) and/or (4) and/or (5) and/or (6) and/or (7) and/or (8) and/or (9) and/or (10) and as defined herein.

(12) A process for production of retinyl acetate comprising providing a retinol-producing host cell as of (11), cultivating said host cell in a suitable culture medium under suitable culture conditions, and optionally isolating and/or purifying the retinyl acetate from the medium.

(13) A process for increasing the conversion of retinol into retinyl acetate by at least 20% in a retinol-producing host cell comprising transforming said host cell, preferably fungal host cell, more preferably a host cell selected from *Yarrowia* or *Saccharomyces*, with a retinol-acetylating enzyme as of (1) and/or (2) and/or (3) and/or (4) and/or (5) and/or (6) and/or (7) and/or (8) and/or (9) and/or (10) and as defined herein.

(14) A process for increasing the production of total retinoids by at least 2× in a retinol-producing host cell comprising transforming said host cell, preferably fungal host cell, more preferably a host cell selected from *Yarrowia* or *Saccharomyces*, with a retinol-acetylating enzyme as of (1) and/or (2) and/or (3) and/or (4) and/or (5) and/or (6) and/or (7) and/or (8) and/or (9) and/or (10) and as defined herein.

FIGURES

FIG. 1. Construction of retinyl acetate-producing *S. cerevisiae* strain showing transformed DNA sequences and integration into genomic DNA by in vivo recombination using connector sequences ("25", "2A", "2B" and "23") and overlap with genomic DNA. "P1" (=*S. cerevisiae* TDH3 promoter) and "T1" (=*S. cerevisiae* ENO1 terminator) are used to express DmBCO; "P2" (=*S. cerevisiae* PGK1 promoter) and "T2" (=*S. cerevisiae* GPM1 terminator) are used to express HsRDH12; "P3" (=*S. cerevisiae* ENO2 promoter) and "T3" (=*S. cerevisiae* ADH1 terminator) are used to express LmATF1 wildtype or mutant (indicated as LmATF1*) sequences. For more details see Example 5.

The following examples are illustrative only and are not intended to limit the scope of the invention in any way. The contents of all references, patent applications, patents, and published patent applications, cited throughout this application are hereby incorporated by reference, in particular WO2008042338, WO2014096992, WO2006102342, US20070166782, WO2019058000, WO2016110512, WO2016172282, US20160130628, WO2009126890, WO2014195378, WO2012125027 or WO2013144257.

EXAMPLES

Example 1: General Methods, Strains, and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

Shake plate assay (*Yarrowia*). For testing the conversion activity of the mutants, typically, 800 μL of 0.25% Yeast extract, 0.5% peptone (0.25×YP) was inoculated with 10 μL of freshly grown *Yarrowia* and overlaid with 800 μL of silicone oil (Clearco, PFS-5cSt) with 5% glucose as carbon source in aqueous phase. Transformants were grown in 24 well plates (Microplate Devices 24 Deep Well Plates Whatman 7701-5102), covered with mat seal (Analytical Sales and Services Inc. Plate Mats 24010CM), sterile sealed with Qiagen Airpore Tape Sheets (19571) and shaken in Infors multi plate shaker (Multitron), 30° C., 800 RPM for 4 days. The silicone oil fraction was removed from the shake plate wells and analyzed by UPLC reverse phase column, with a photo-diode array detector. This method is also used in Example 2.

Growth in roller drums. For testing the conversion activity of ATF enzymes in *Saccharomyces*, typically, 5 ml of 1% Yeast extract, 2% Peptone (1×YP) were inoculated from a fresh plate of *Saccharomyces* and overlayed with 500 μL of mineral oil (Drakeol 5, Penreco, Karns City, PA USA) with 2% glucose or 2% galactose (or as otherwise indicated) as carbon source in the aqueous phase. Clonal isolates of transformants were grown in glass culture tubes (VWR 47729-583) placed on a roller drum (New Brunswick Scientific TC-7) placed at 30° C. for 4 days. The mineral oil fraction was removed from the culture tube and analyzed by UPLC reveres phase column, with a photo-diode array detector. This method was also used in Example 2.

DNA transformation. *Yarrowia lipolytica* strains were transformed from overnight growth on YPD plate media. 50 μL of cells was scraped from a plate and transformed by incubation in 500 μL with 1 μg transforming DNA, typically linear DNA for integrative transformation, 40% PEG 3550 MW, 100 mM lithium acetate, 50 mM Dithiothreitol, 5 mM Tris-Cl pH 8.0, 0.5 mM EDTA for 30 minutes at 40° C. and plated directly to selective media or, in the case of dominant antibiotic marker selection, the cells were out grown on YPD liquid media for 4 hours at 30° C. before plating on the selective media. *Saccharomyces* strains were transformed using the lithium-acetate method from exponential phase YPD-grown cells, which were grown by subculture of an overnight YPD culture. $10^8$ cells/transformation were harvested, and resuspended in a mixture containing 40% PEG 3350 (MW), 100 mM lithium acetate, 10 mM Tris-Cl pH 8.0, 1 mM EDTA, 5 μg sheared salmon sperm DNA, and 2 μg of linearized transforming DNA, in a final volume of 500 μL. This mixture was incubated at 30° C. for 1 hour, followed by 42° C. for 30 minutes. The cells were then pelleted and resuspended in liquid YPD media, and permitted to grow for 3 hours at 30° C. or overnight at 22° C. to allow for expression of the HygR antibiotic resistance gene before plating on the selective media, containing 100 μg/ml hygromycin. Most of the DNA sequences used herein are codon-optimized for expression in the respective host system and as indicated in the sequence listing.

DNA molecular biology. Genes to be used in *Yarrowia lipolytica* were synthesized with NheI and MluI ends in pUC57 vector (GenScript, Piscataway, NJ), with introduction of amino acid substitutions according to Tables 4A-4E (column "mutation") or Table 5. Typically, the LmATF1 gene (*Yarrowia lipolytica* codon optimized SEQ ID NO:3), SbATF1 gene (*Yarrowia lipolytica* codon optimized SEQ ID NO:6), LffATF1 (*Yarrowia* codon optimized SEQ ID NO:8) were subcloned to the MB5082 'URA3', MB6157 HygR, and MB8327 NatR vectors for marker selection in *Yarrowia lipolytica* transformations, as in WO2019058000 (Example 1). For generation of Wa1ATF and Wa3ATF mutants, plasmids containing the respective ATF allele (*Yarrowia lipolytica* codon optimized SEQ ID NOs:12 and 14), genes DrBCO gene (*Yarrowia lipolytica* codon optimized SEQ ID NO:18), FfRDH12 gene (*Yarrowia lipolytica* codon optimized SEQ ID NO:22) and URA3 as selection marker were generated (see Table 5). For clean gene insertion by random nonhomologous end joining of the gene and marker, HindIII/XbaI (MB5082) or PvuII (MB6157 and MB8327) digests of the respective plasmids were purified by gel electrophoresis and a Qiagen gel purification column. MB5082 'URA3' marker could be reused due to flanking repetitive sequences that enable selection of circular excisants of the URA3 cassette on FOA-containing medium. The NatR and HygR markers could be removed by transient expression of Cre recombinase that results in antibiotic-sensitive excisants due to the flanking lox sites. Cas9 mediated deletion of the HOM3 was done by pre-transforming the episomal Cas9 plasmid MB7452 (*Yarrowia lipolytica* codon optimized SEQ ID NO:25) using NatR marker selection. Subsequently the episomal plasmid MB8549 (*Yarrowia lipolytica* codon optimized SEQ ID NO:26) with the guide sequence for hom3 cleavage was transformed using the G418R. Transformants were screened for homoserine auxotrophy and subsequently sequenced using primers flanking the HOM3 sequence and clean frameshifts were selected to move forward. For expression of mutant ATFs in *Saccharomyces cerevisiae*, first strain CAR-0002 was constructed as follows: Three carotenoid gene expression cassettes, crtE, crtYB and crtI from Xanthophyllomyces dendrorhous codon optimized for expression in *Saccharomyces cerevisiae* were transformed into strain CEN.PK113-7D (van Dijken et al., Enzyme Microb Technol. 26(9-10), p. 706-714, 2000). The expression cassettes were integrated in the INT1 integration site using the CRISPR approach as described in Example 9 of WO2016110512. Expression cassettes containing strong constitutive promoters (see SEQ ID NO:139, SEQ ID NO:142 and SEQ ID NO:148 of WO2016110512) and donor DNA flank sequences (see SEQ ID NO:149 and SEQ ID NO:152 of WO2016110512) were transformed into CEN.PK113-7D. The sequence of the INT1 genomic target (protospacer) is set out in SEQ ID NO:176 of WO2016110512. The INT1 integration site is located at the non-coding region between NTR1 (YOR071c) and GYP1 (YOR070c) located on chromosome XV. Strain CEN.PK113-7D was transformed using the LiAc/salmon sperm (SS) carrier DNA/PEG method (Gietz and Woods, Methods in Enzymology, Vol. 350, p. 87-86, 2002) using DNA concentrations as described by Verwaal et al. (Yeast, 35, p. 201-211, 2018). Subsequently, the retinol producing strain MY4834 was created by serial transformation of CAR-0002 with SfiI-linearized plasmid MB8433 (SEQ ID NO:27), containing a constitutive expression cassette for DmBCO (*Saccharomyces cerevisiae* codon optimized SEQ ID NO:20; TDH3 promoter, PGK1 terminator) with selection on hygromycin, and with a PCR amplicon using primers MO12301 (SEQ ID NO:59) and MO12302 (SEQ ID NO:60) from plasmid MB8431 (SEQ ID NO:28), containing an expression cassette for HsRDH12 (*Saccharomyces cerevisiae* codon optimized SEQ ID NO:24; TDH3 promoter, PGK1 terminator), targeting the PCR amplicon to a URA3 locus with selection on fluoroorotic acid (FOA). ATF genes (*Saccharomyces cerevisiae* codon optimized LmATF1 wt according to SEQ ID NO:4 and mutants) for expression in *Saccharomyces* were synthesized with XbaI and PstI ends into XbaI/SbfI sites of MB7621 (Genscript, Piscataway, NJ) for constitutive expression from the HSP26 promoter or an MB7621 derivative with inducible expression from the GAL1 promoter, MB9606. MB9606 was created by removing the HSP26 promoter containing SpeI/XbaI fragment from MB7621, and replacement with the GAL1 promoter sequence. These vectors use the NatR gene for selection during *Saccharomyces cerevisiae* transformation. For clean gene insertion by targeted homologous recombination, SfiI digests of the respective plasmids were purified by gel electrophoresis and a Qiagen gel purification column. The NatR marker in plasmid MB7621 and derivatives was removed by transient expression of Cre recombinase that resulted in antibiotic-sensitive excisants due to the flanking lox sites. Plasmids were made using standard molecular genetics techniques or are available by synthetic biology methods (GenScript, Piscataway, NJ).

Sequences. Plasmids and strains comprising the respective wild-type LmATF1 (originated from *L. mirantina*), SbATF1 (originated from *S. bayanus*), LffATF1 (originated from *L. fermentati*) or Wa1ATF and Wa3ATF (both originated from Wickerhamomyces *anomalus*) enzymes that were used (including generation of the respective amino acid substitutions as described herein) are listed in Table 1 and 2. The respective nucleotide and amino acid sequences are shown in the sequence listing, with codon-optimized sequences for expression in *Yarrowia lipolytica* or *Saccharomyces cerevisiae* specifically indicated.

Based on the non-modified LmATF1 according to SEQ ID NO:1, non-modified Wa1ATF according to SEQ ID NO:11 and non-modified Wa3ATF according to SEQ ID NO:13 one or more amino acid substitution(s) have been introduced in selected position(s) as shown in Tables 4A-4E, 5, 6 and 8. Amino acid substitutions can be introduced at the corresponding position(s) in the amino acid sequence of SbATF1 (such as, e.g., N39S, N39A, F373A, K492S, G444L, G444F, G444M, G444Q, V371I, V491R, V491Q—either as single mutation or combinations of at least 2 mutations based on the non-modified SbATF1 according to SEQ ID NO:5) or LffATF1 (such as, e.g., Q28S, Q28A, G363A, A482S, Q434L, Q434F, Q434M, V361, V481R, V481Q—either as single mutation or combinations of at least 2 mutations based on the non-modified LffATF1 according to SEQ ID NO:7). Plasmids MB7621 and MB9442 were used for expression in *Saccharomyces cerevisiae*.

TABLE 1 list of plasmids used for construction of the strains carrying the
(non-modified or modified) heterologous *Yarrowia
lipolytica* codon-optimized ATF1-genes from
*Lachancea mirantina* LmATF1 (SEQ ID
NO: 3), *Saccharomyces bayanus* SbATF1 (SEQ ID NO: 6),
*Lachancea fermentati* LffATF1 (SEQ ID NO: 8), and
*Wickerhamomyces anomalus* Wa1ATF (SEQ ID
NO: 12) and Wa3ATF (SEQ ID NO: 14).
For expression of the LmATF1 gene in
*Saccharomyces*, the codon-optimized sequence ID NO: 4
was used. Plasmids MB9679 (SEQ ID NO: 29) and
MB9688 (SEQ ID NO: 30) furthermore contain genes encoding
DrBCO, FfRDH12 and URA3 as selection marker.

| Plasmid | Backbone | Insert |
|---|---|---|
| MB7452 | MB6157 | Cas9 |
| MB8549 | MB7200 | Cas9 hom3 |
| MB8457 | MB5082 | UmCCO1 |
| MB8849 | MB5082 | LmATF1 |
| MB8064 | MB5082 | SbATF1 |
| MB8806 | MB5082 | LffATF1 |
| MB9679 | MB5082 | Wa1ATF |
| MB9682 | MB5082 | Wa1ATF_G329A |
| MB9688 | MB5082 | Wa3ATF |
| MB9689 | MB5082 | Wa3ATF_T404M |

TABLE 1-continued list of plasmids used for construction of the strains carrying the
(non-modified or modified) heterologous *Yarrowia*
*lipolytica* codon-optimized ATF1-genes from
*Lachancea mirantina* LmATF1 (SEQ ID
NO: 3), *Saccharomyces bayanus* SbATF1 (SEQ ID NO: 6),
*Lachancea fermentati* LfATF1 (SEQ ID NO: 8), and
*Wickerhamomyces anomalus* Wa1ATF (SEQ ID
NO: 12) and Wa3ATF (SEQ ID NO: 14).
For expression of the LmATF1 gene in
*Saccharomyces*, the codon-optimized sequence ID NO: 4
was used. Plasmids MB9679 (SEQ ID NO: 29) and
MB9688 (SEQ ID NO: 30) furthermore contain genes encoding
DrBCO, FfRDH12 and URA3 as selection marker.

| Plasmid | Backbone | Insert |
|---|---|---|
| MB9690 | MB5082 | Wa3ATF_T404Q |
| MB9606 | | Expression vector/backbone for LmATF1 |
| MB9608* | MB9606 | LmATF-wt |
| MB9609* | MB9606 | LmATF1_S480Q_V334L |
| MB9610* | MB9606 | LmATF1_S480Q_G409A |
| MB9611* | MB9606 | LmATF1_S480Q_G409A_V407I_H69A_I484L |
| MB9612* | MB9606 | LmATF1_S480Q_G409A_V407I_H69A_V334L |
| MB8431* | MB7622 | Expression vector for HsRDH12 |
| MB8433* | MB7622* | Expression vector for DmBCO |

Plasmids marked with "*" contain codon-optimized reading frames for *S. cerevisiae*. For more details, see text.

TABLE 2 list of *Yarrowia* strains (indicated with "ML") used for production of
retinoids carrying the heterologous (non-modified or modified)
ATF1 genes.

| Strain | Description | First described in |
|---|---|---|
| ML7788 | Carotene strain | WO2016172282 |
| ML15710 | ML7788 transformed with MB7311-Mucor CarG | WO2016172282 |
| ML17544 | ML 15710 cured of URA3 by FOA and HygR by Cre/lox | here |
| ML17968 | ML17544 transformed with MB8457 UmCCO1 | here |
| ML18183 | ML17968 transformed with MB7452 Cas9 NatR CEN | here |
| ML18210 | ML18183 transformed with MB8549 Cas9 hom3 | here |
| ML18667 | ML17544 transformed with MB9679 | here |

For more details, see text.

UPLC reverse phase retinol method. For rapid screening this method does not separate cis-isomers, only major functional groups. A Waters Acquity UPLC with PDA detection (or similar) with auto sampler was used to inject samples. An Acquity UPLC HSS T3 1.8 um P/N 186003539 was used to resolve retinoids. The mobile phase consisted of either, 1000 mL hexane, 30 mL isopropanol, and 0.1 mL acetic acid for retinoid related compounds. The flow rate for each was 0.6 mL per minute. Column temperature was 20° C. The injection volume was 5 μL. The detector was a photodiode array detector collecting from 210 to 600 nm. Analytes were detected according to Table 3.

TABLE 3A list of analytes using reverse phase retinol method.
The addition of all added intermediates gives the
total amount retinoids. Beta-carotene* can be
detected in 325 nm and will interfere with
retinyl ester quantitation, therefore
care must be taken to observe the carotene
peak and not include them in the
retinoid quantification.

| Intermediates | Retention time [min] | Lambda max [nm] | Response factor |
|---|---|---|---|
| retinyl-acetate | 2.93 | 325 | 1.00 |
| retinyl-esters | 3.2-3.8 | 325 | 1.68 |
| retinal | 2.77 | 325 | 0.87 |
| retinol | 2.73 | 325 | 0.87 |
| Beta-carotene* | 3.56 | 450 | N/A |

"N/A" means "not available".
For more details, see text.

TABLE 3B

UPLC Method Gradient with solvent
A: water; solvent B: acetonitrile; solvent C:
methanol; solvent D: tert-butyl methyl ether.

| Time [min] | % A | % B | % C | % D | Flow [ml/min] | Pressure [psi/bar] |
|---|---|---|---|---|---|---|
| 0 | 50 | 50 | 0 | 0 | 0.5 | 9500-14000 max |
| 0.5 | 50 | 50 | 0 | 0 | 0.5 | |
| 1.0 | 0 | 50 | 50 | 0 | 0.5 | |
| 1.25 | 0 | 0 | 100 | 0 | 0.5 | |
| 3.25 | 0 | 0 | 5 | 95 | 0.5 | |
| 3.5 | 0 | 0 | 5 | 95 | 0.5 | |
| 4.0 | 0 | 0 | 100 | 0 | 0.5 | |
| 4.25 | 0 | 50 | 50 | 0 | 0.5 | |
| 4.5 | 50 | 50 | 0 | 0 | 0.5 | |

Method Calibration. Method is calibrated on retinyl acetate, retinols and retinals are quantitated against retinyl-acetate using the indicated response factor. Retinyl Acetate is dissolved in THF at –200 μg/ml for stock solution using a volumetric flask. Using volumetric flasks, ×20, ×50 and ×100 dilutions of stock solution in 50/50 methanol/MTBE were made. UV absorbance of retinyl acetate becomes nonlinear fairly quickly, so care must be taken to stay within the linear range. Consequently, lower concentrations might be better. Retinyl palmitate can also be used as retinyl ester calibration. Peaks for retinyl acetate at about 3 minutes and peaks for retinyl esters (long-chain retinyl esters) at around 3.5 minutes.

Sample preparation. Samples were prepared by various methods depending on the conditions. For whole broth or washed broth samples the broth was placed in a Precellys® tube, weighed, and mobile phase was added. Briefly in a 2 ml Precellys® tube, add 25 μl of well mixed broth and 975 μl of THF. The samples were then processed in a Precellys® homogenizer (Bertin Corp, Rockville, MD, USA) on the highest setting 3× according to the manufacturer's directions, typically 3×15×7500 tpms. For the washed pellet the samples were spun in a 1.7 ml tube in a microfuge at 10000 rpm for 1 minute, the broth decanted, 1 ml water added, mixed, pelleted and decanted, and brought up to the original volume. The mixture was pelleted again and brought up in appropriate amount of mobile phase and processed by Precellys® bead beating. For analysis of silicone oil fraction, the sample was spun at 4000 RPM for 10 minutes and the oil was decanted off the top by positive displacement pipet (Eppendorf, Hauppauge, NY, USA) and diluted into mobile phase mixed by vortexing and measured for retinoid concentration by UPLC analysis.

Fermentation conditions in *Yarrowia*. Fermentations were identical to the previously described conditions using preferably a silicone oil overlay and stirred tank that was preferably glucose in a bench top reactor with 0.5 L to 5 L total volume (see WO2016172282). Generally, the same results were observed with a fed batch stirred tank reactor with an increased productivity demonstrating the utility of the system for the production of retinoids. Preferably, fermentations were batched with 5% glucose and 20% silicone oil was added after dissolved oxygen dropped below about 20% and feed was resumed to achieve 20% dissolved oxygen throughout the feeding program.

Example 2: Production of Retinyl Acetate in *Yarrowia lipolytica* Expressing Mutant LmATF For expression of heterologous LmATF1 in *Yarrowia lipolytica* as host, the retinol producing strain ML17968 comprising the gene encoding *Ustilago maydis* beta-carotene oxidase UmCCO1 (*Yarrowia lipolytica* codon optimized SEQ ID NO:16) was transformed with purified PvuII gene fragments containing acetyltransferase gene fragments as defined herein and as shown in *Yarrowia lipolytica* codon-optimized sequence ID NOs: 3, 6, 8, 10 linked to a Hygromycin resistance marker (HygR) for selection on rich media (YPD) containing 100 µg/ml hygromycin. Prior to plating the cultures were outgrown in YPD for 4 hours to synthesize the antibiotic resistance genes. Isolates were screened for acetylation in shake plate assays, specifically using 5 to 10% glucose as a carbon source in 0.25×YP with silicone oil as an overlay and successful isolates were further screened in fed batch stirred tank reactor with glucose feed and silicone oil overlay, which showed an order of magnitude increased productivity indicating utility in the production of retinoids. The results (shake plate assay) are shown in Tables 4A-4E, showing the percentage of retinyl acetate, based on the total amount of retinoids present in the host cell that is increased by at least about 0.3× as compared to a host cell expressing the respective non-modified wildtype ATF. First, clones were tested with only 1 single amino acid substitution (see Tab.4A).

TABLE 4A acetylation of retinol into retinyl acetate ("retAc") as enhanced by action of modified Atf1 enzymes comprising a single amino acid substitution on a position corresponding to the respective position in the Atf1 of *Lachancea mirantina* according to SEQ ID NO: 1, designated as "wt", i.e. non-modified, and compared to non-modified Atf1 of *Saccharomyces bayanus* (SbATF1-wt) according to SEQ ID NO: 5 and *Lachancea fermentati* (LffATF1-wt) according to SEQ ID NO: 7.

| Mutation | % retAc |
|---|---|
| SbATF1-wt | 10.3 |
| LffATF1-wt | 11.7 |
| LmATF1-wt | 40.4 |
| LmATF1-Q68T | 55.2 |
| LmATF1-H69A | 61.7 |
| LmATF1-H69N | 59.4 |
| LmATF1-H69S | 60.9 |
| LmATF1-Q72K | 61.9 |
| LmATF1-Q72N | 55.4 |

TABLE 4A-continued acetylation of retinol into retinyl acetate ("retAc") as enhanced by action of modified Atf1 enzymes comprising a single amino acid substitution on a position corresponding to the respective position in the Atf1 of *Lachancea mirantina* according to SEQ ID NO: 1, designated as "wt", i.e. non-modified, and compared to non-modified Atf1 of *Saccharomyces bayanus* (SbATF1-wt) according to SEQ ID NO: 5 and *Lachancea fermentati* (LffATF1-wt) according to SEQ ID NO: 7.

| Mutation | % retAc |
|---|---|
| LmATF1-G171K | 55.0 |
| LmATF1-G171N | 58.6 |
| LmATF1-N172G | 53.3 |
| LmATF-Q173L | 57.3 |
| LmATF1-V174I | 57.0 |
| LmATF1-S176A | 55.0 |
| LmATF1-S176G | 57.1 |
| LmATF1-L178V | 53.0 |
| LmATF1-A291G | 52.4 |
| LmATF1-A291S | 50.7 |
| LmATF1-G292A | 53.4 |
| LmATF1-G292N | 57.4 |
| LmATF1-G292S | 55.6 |
| LmATF1-F294L | 54.1 |
| LmATF1-F294V | 58.4 |
| LmATF1-Y301F | 55.5 |
| LmATF1-P307I | 54.5 |
| LmATF1-T308V | 55.6 |
| LmATF1-T311I | 56.6 |
| LmATF1-T311M | 55.2 |
| LmATF1-S312A | 53.7 |
| LmATF1-H320N | 57.4 |
| LmATF1-Y322F | 57.3 |
| LmATF1-Y322V | 56.3 |
| LmATF1-V334L | 62.7 |
| LmATF1-V334M | 53.1 |
| LmATF1-S362A | 54.4 |
| LmATF1-S405A | 60.8 |
| LmATF1-V407I | 66.8 |
| LmATF1-G409A | 62.9 |
| LmATF1-S480E | 52.4 |
| LmATF1-S480F | 61.4 |
| LmATF1-S480L | 60.3 |
| LmATF1-S480M | 62.8 |
| LmATF1-S480Q | 65.6 |
| LmATF1-L483V | 54.6 |
| LmATF1-I484L | 60.9 |
| LmATF1-V490I | 55.7 |
| LmATF1-D492V | 53.9 |
| LmATF1-I520A | 54.2 |
| LmATF1-C521A | 54.3 |
| LmATF1-C521V | 57.6 |
| LmATF1-A522S | 55.3 |
| LmATF1-A522T | 58.6 |
| LmATF1-D524N | 52.3 |
| LmATF1-D524S | 57.7 |
| LmATF1-Q525V | 56.6 |
| LmATF1-Q525I | 57.6 |
| LmATF1-Q525R | 67.0 |
| LmATF1-G526S | 64.8 |

For more details, see text.

Further tests were performed with a combination of 2 amino acid substitutions, the results are shown in Table 4B.

TABLE 4B acetylation of retinol into retinyl acetate ("retAc") as enhanced by action of modified Atf1 enzymes comprising 2 amino acid substitutions on positions corresponding to the respective positions in the Atf1 of *Lachancea mirantina* according to SEQ ID NO: 1, designated as "wt", and compared to non-modified Atf1 of *Saccharomyces bayanus* (SbATF1-wt) according to SEQ ID NO: 5 and *Lachancea fermentati* (LffATF1-wt) according to SEQ ID NO: 7.

| Mutation | % retAc |
| --- | --- |
| SbATF1-wt | 10.3 |
| LffATF1-wt | 11.7 |
| LmATF1-wt | 40.4 |
| LmATF1-V407I H69S | 67.0 |
| LmATF1-V407I Q72K | 66.0 |
| LmATF1-V407I T311I | 56.2 |
| LmATF1-V407I V334L | 65.7 |
| LmATF1-V407I S480L | 61.3 |
| LmATF1-V407I I484L | 65.3 |
| LmATF1-G409A H69N | 67.0 |
| LmATF1-G409A H69S | 69.6 |
| LmATF1-G409A H69A | 74.2 |
| LmATF1-G409A Q72K | 59.7 |
| LmATF1-G409A T311I | 65.9 |
| LmATF1-G409A V334L | 63.4 |
| LmATF1-G409A V407I | 67.4 |
| LmATF1-G409A S480L | 52.0 |
| LmATF1-S480Q Q68T | 65.8 |
| LmATF1-S480Q H69N | 63.8 |
| LmATF1-S480Q H69S | 69.6 |
| LmATF1-S480Q H69A | 70.1 |
| LmATF1-S480Q Q72K | 62.8 |
| LmATF1-S480Q T311I | 62.7 |
| LmATF1-S480Q V334L | 75.3 |
| LmATF1-S480Q V407I | 73.8 |
| LmATF1-S480Q G409A | 73.5 |
| LmATF1-S480Q I484L | 67.0 |

For more details, see text.

Some of the double mutants tested above were further modified by introduction of an additional mutation, i.e. leading to triple mutations. The results are shown in Table 4C.

TABLE 4C acetylation of retinol into retinyl acetate ("retAc") as enhanced by action of modified Atf1 enzymes comprising 3 amino acid substitutions on positions corresponding to the respective positions in the Atf1 of *Lachancea mirantina* according to SEQ ID NO: 1, designated as "wt", and compared to non modified Atf1 of *Saccharomyces bayanus* (SbATF1-wt) according to SEQ ID NO: and *Lachancea fermentati* (LffATF1-wt) according to SEQ ID NO: 7.

| Mutation | % retAc |
| --- | --- |
| SbATF1-wt | 10.3 |
| LffATF1-wt | 11.7 |
| LmATF1-wt | 40.4 |
| LmATF1-G409A V407I H69N | 70.3 |
| LmATF1-G409A V407I Q72K | 68.7 |
| LmATF1-G409A V407I T311I | 70.6 |
| LmATF1-G409A V407I V334L | 71.1 |
| LmATF1-G409A V407I S480L | 59.2 |
| LmATF1-G409A V407I I484L | 69.9 |
| LmATF1-S480Q V407I Q68T | 58.5 |
| LmATF1-S480Q V407I H69N | 64.1 |
| LmATF1-S480Q V407I H69S | 67.1 |
| LmATF1-S480Q V407I H69A | 69.9 |
| LmATF1-S480Q V407I Q72K | 67.0 |
| LmATF1-S480Q V407I T311I | 70.2 |
| LmATF1-S480Q V407I V334L | 63.1 |
| LmATF1-S480Q V407I I484L | 58.1 |
| LmATF1-S480Q G409A Q68T | 63.7 |

TABLE 4C-continued acetylation of retinol into retinyl acetate ("retAc") as enhanced by action of modified Atf1 enzymes comprising 3 amino acid substitutions on positions corresponding to the respective positions in the Atf1 of *Lachancea mirantina* according to SEQ ID NO: 1, designated as "wt", and compared to non modified Atf1 of *Saccharomyces bayanus* (SbATF1-wt) according to SEQ ID NO: and *Lachancea fermentati* (LffATF1-wt) according to SEQ ID NO: 7.

| Mutation | % retAc |
| --- | --- |
| LmATF1-S480Q G409A H69A | 67.2 |
| LmATF1-S480Q G409A H69N | 67.3 |
| LmATF1-S480Q G409A I484L | 67.6 |

For more details, see text.

In a next step, combinations of triple mutations LmATF1-S480Q G409A V407I with further single mutations were tested. The results are shown in Table 4D.

TABLE 4D acetylation of retinol into retinyl acetate ("retAc") as enhanced by action of modified Atf1 enzymes comprising 4 amino acid substitutions on positions corresponding to the respective positions in the Atf1 of *Lachancea mirantina* according to SEQ ID NO: 1, designated as "wt", and compared to non-modified Atf1 of *Saccharomyces bayanus* (SbATF1-wt) according to SEQ ID NO: 5 and *Lachancea fermentati* (LffATF1-wt) according to SEQ ID NO: 7.

| Mutation | % retAc |
| --- | --- |
| SbATF1-wt | 10.3 |
| LffATF1-wt | 11.7 |
| LmATF1-wt | 40.4 |
| LmATF1-S480Q G409A V407I H69N | 75.2 |
| LmATF1-S480Q G409A V407I H69A | 76.7 |
| LmATF1-S480Q G409A V407I H69S | 77.4 |
| LmATF1-S480Q G409A V407I Q72K | 63.2 |
| LmATF1-S480Q G409A V407I T311I | 76.8 |
| LmATF1-S480Q G409A V407I V334L | 77.6 |
| LmATF1-S480Q G409A V407I I484L | 74.1 |
| LmATF1-S480L G409A V407I T311I | 73.1 |

For more details, see text.

Finally, combinations of 5 amino acid substitutions comprising modifications of amino acid residues S480, G409, V407 and H69 were tested for acetylation of retinol. The results are shown in Table 4E.

TABLE 4E acetylation of retinol into retinyl acetate ("retAc") as enhanced by action of modified Atf1 enzymes comprising 5 amino acid substitutions on positions corresponding to the respective positions in the Atf1 of *Lachancea mirantina* according to SEQ ID NO: 1, designated as "wt", and compared to non-modified Atf1 of *Saccharomyces bayanus* (SbATF1-wt) according to SEQ ID NO: 5 and *Lachancea fermentati* (LffATF1-wt) according to SEQ ID NO: 7.

| Mutation | % retAc |
| --- | --- |
| SbATF1-wt | 10.3 |
| LffATF1-wt | 11.7 |
| LmATF1-wt | 40.4 |
| LmATF1-S480Q G409A V407I H69A V334L | 77.6 |
| LmATF1-S480Q G409A V407I H69A I484L | 83.8 |
| LmATF1-S480Q G409A V407I H69S Q72K | 55.9 |
| LmATF1-S480Q G409A V407I H69N Q72K | 59.8 |
| LmATF1-S480Q G409A V407I H69N T311I | 56.1 |

TABLE 4E-continued acetylation of retinol into retinyl acetate ("retAc")
as enhanced by action of modified Atf1
enzymes comprising 5 amino acid substitutions on
positions corresponding to the respective
positions in the Atf1 of *Lachancea*
*mirantina* according to SEQ ID NO: 1,
designated as "wt", and compared to non-
modified Atf1 of *Saccharomyces bayanus* (SbATF1-
wt) according to SEQ ID NO: 5 and *Lachancea*
*fermentati* (LffATF1-wt) according to SEQ ID NO: 7.

| Mutation | % retAc |
|---|---|
| LmATF1-S480Q G409A V407I H69N V334L | 63.3 |
| LmATF1-S480Q G409A V407I H69N I484L | 68.9 |

For more details, see text.

As shown, the use of LmATF1 carrying one or more mutation(s) in *Yarrowia* leads to increase in retinyl acetate percentage in the range of up to twice as much as using the LmATF1 wildtype.

Example 3: Production of Retinyl Acetate in *Yarrowia lipolytica* Expressing Mutant WaATF For expression of heterologous ATF in *Yarrowia lipolytica* as a host, a similar approach was taken as in Example 2, except a modified derivative of ML17544, ML18667, was transformed with a plasmid listed in Table 5, each of which consists of the indicated ATF allele (i.e. wildtype or modified from of *Yarrowia lipolytica* Wa1ATF according to SEQ ID NO:12 or Wa3ATF according to SEQ ID NO:14), DrBCO (*Yarrowia lipolytica* codon optimized SEQ ID NO:18), and FfRDH12 (*Yarrowia lipolytica* codon optimized SEQ ID NO:22. Transformants of ML18667 with the SfiI-linearized plasmids from Table 5A were selected for uracil prototrophy. Transformants were grown in shake plates as in Example 2, and the percentage of retinyl acetate using the mutant ATFs in relation to the percentage of retinyl acetate using the wildtype ATF (set as 100%) is shown in Table 5.

As shown, the use of *Wackeromyces anomalus* ATF homologs carrying one or more mutation(s) in *Yarrowia* leads to increase in retinyl acetate percentage in the range of up to twice as much as using the LmATF1 wildtype.

TABLE 5 acetylation of retinol into retinyl acetate ("retAc") as enhanced by
action of modified Atf1 enzymes comprising a single amino acid substitution
on a position corresponding to the respective position in the Atf1 of
*Wickerhamomyces anomalus* Wa1ATF and Wa3ATF according to
SEQ ID NO: 11 and 13, respectively, designated as "wt", i.e. non-modified.
Retinyl acetate formation using the wt-ATF is set to 100%.

| Plasmid | Mutation | retAc |
|---|---|---|
| MB9679 | Wa1ATF-wt | 100% |
| MB9682 | Wa1ATF-G329A | 416% |
| MB9688 | Wa3ATF-wt | 100% |
| MB9689 | Wa3ATF-T404M | 136% |
| MB9690 | Wa3ATF-T404Q | 132% |

For more details, see text.

Example 4: Production of Retinyl Acetate in *Saccharomyces cerevisiae* Expressing Mutant ATF For expression of heterologous LmATF1 (wt and mutants based on *Saccharomyces cerevisiae* codon optimized SEQ ID NO:4) in *Saccharomyces cerevisiae* as a host, the retinol producing strain MY4834 (see Ex. 1) was transformed with purified SfiI-digested gene fragments containing nourseothricin resistance marker (NatR) for selection on rich media (YPD) containing 100 µg/ml nourseothricin. Prior to plating the cultures are outgrown in YPD for 3 hours to synthesize the antibiotic resistance gene. Transformations with 2.5-3 µg of linearized plasmid were done in parallel for the backbone expression plasmid lacking an LmATF1 (MB9606), but with a NatR marker. Transformation mixtures were plated on glucose and screened for production of retinyl acetate in culture tubes grown as described above (Ex. 1). After growth, mineral oil overlays were sampled from centrifuged cultures, and subjected to UPLC analysis (see Example 1). The results are shown in Table 6, wherein the percentage of retinyl acetate using the mutant ATFs in relation to the percentage of retinyl acetate using the wildtype ATF (set as 100%) are given. As shown, the use of LmATF1 carrying two or more mutation(s) in *Saccharomyces* leads to increase in retinyl acetate percentage in the range of up to twice as much as using the LmATF1 wildtype.

TABLE 6 acetylation of retinol as enhanced by action of various
LmATF1-mutantsusing galactose as carbon source,
in comparison to wild-type LmATF1 according
to SEQ ID NO: 1, designated as "wt", i.e.
non-modified. "retAc" means retinyl acetate with
retinyl acetate formation using the wt-ATF is set to 100%.

| Plasmid | Mutation | retAc |
|---|---|---|
| MB9606 | Empty vector | 0 |
| MB9608 | LmATF1-wt | 100% |
| MB9609 | LmATF1_S480Q_V334L | 237% |
| MB9610 | LmATF1_S480Q_G409A | 187% |
| MB9611 | LmATF1-S480Q_G409A_V407I_H69A_I484L | 115% |
| MB9612 | LmATF1_S480Q_G409A_V407I_H69A_V334L | 117% |

For more details, see text.

Similar results were obtained when growing the host cells comprising the LmATF1 mutants expressed from a constitutive promoter on glucose, i.e. a clear increase in retinyl acetate formation upon introduction of mutations compared to the wild-type as indicated in Table 6.

Example 5: Production of Retinyl Acetate in *Saccharomyces cerevisiae* Expressing Mutant ATF with Xylose as Carbon Source In this example retinyl acetate production in *S. cerevisiae* is demonstrated using xylose as C-source. Retinyl acetate production using xylose is compared to production using glucose as C-source.

Transformation of carotenoid gene expression cassettes. Strain RN1014 (WO2014195378A1) was obtained through in vivo engineering of strain RN1001 (WO2012125027) on xylose and acetic acid. The genotype of strain RN1001 is MAT a, ura3-52, leu2-112, gre3::loxP, loxP-Ptpi::TAL1, loxP-Ptpi::RK11, loxP-Ptpi-TKL1, loxP-Ptpi-RPE1, delta:: PadhlXKS1Tcyc1-LEU2, delta::URA3-Ptpi-xylA-Tcyc1.

Three carotenoid gene expression cassettes, crtE, crtYB and crtI from Xanthophyllomyces dendrorhous codon optimized for expression in *Saccharomyces cerevisiae* are transformed into strain RN1014. The expression cassettes integrated in the INT1 integration site using the CRISPR approach as described in Example 9 of WO2016110512. Expression cassettes containing strong constitutive promoters (see SEQ ID NO:139, SEQ ID NO:142 and SEQ ID NO:148 of WO2016110512) and donor DNA flank sequences (see SEQ ID NO:149 and SEQ ID NO:152 of WO2016110512) are transformed into RN1014. The sequence of the INT1 genomic target (protospacer) is set out in SEQ ID NO:176 of WO2016110512. The INT1 integration site is located at the non-coding region between NTR1 (YOR071c) and GYP1 (YOR070c) located on chromosome XV. Strain RN1014 is transformed using the LiAc/salmon sperm (SS) carrier DNA/PEG method (Gietz and Woods, Methods in Enzymology, Vol. 350, p. 87-86, 2002) using DNA concentrations as described by Verwaal et al. (Yeast, 35, p. 201-211, 2018).

The transformation mixtures are plated on YPD-agar (10 grams per liter of yeast extract, 20 grams per liter of peptone, 20 grams per liter of dextrose, 20 grams per liter of agar) containing 200 µg nourseothricin (NatMX, Jena Bioscience, Germany) and 200 µg G418 (Sigma Aldrich, Zwijndrecht, the Netherlands) per ml. The agar plates are incubated at 30° C. until colonies appear on the plates.

When three genes, crtE, crtYB and crtI from Xanthophyllomyces dendrorhous are introduced and overexpressed in *Saccharomyces cerevisiae*, the transformants will produce carotenoids with beta-carotene as end-product, which is a colored compound, and consequently results in colored transformants (Verwaal et al., Applied and Environmental Microbiology, Vol. 73, No. 13, p. 4342-4350, 2007). A first indication of successfully transformed RN1014 cells is the appearance of colored transformants. Correct integration of the crt donor DNA expression cassettes can be confirmed by PCR, using for example genomic DNA isolated from a transformant, using methods known by the person skilled in the art. Carotenoid production in RN1014 transformants can be determined as described in Example 9 of WO2016110512.

Subsequently, the guide RNA expression plasmid is removed from a PRN1014 transformant containing crtE, crtYB and crtI expression cassettes while maintaining plasmid pCSN061 (SEQ ID NO:31) that expresses Cas9. The colony is inoculated in YPD medium supplemented with 200 µg G418 per ml, incubating the liquid culture in a shake flask for at least two days at 30° C. at 250 rpm in a shaking incubator. Aliquots are streaked onto YPD-agar plates supplemented with 200 µg G418 per ml and plates are incubated for at least two days at 30° C. Single colonies are re-streaked onto YPD-agar plates supplemented with 200 µg G418 per ml and YPD-agar plates supplemented with 200 µg G418 and 200 µg nourseothricin (NatMX, Jena Bioscience, Germany) per ml. The plates are incubated for at least two days at 30° C. A single colony that grows on the G418 containing plate, but not on the G418 and nourseothricin containing plate, indicating loss of the guide RNA plasmid, is selected. This PRN1014 transformant containing crtE, crtYB and crtI expression cassettes and plasmid pCSN061 expressing Cas9 is referred as strain PRN1014_crtE_crtYB_crtI+pCSN061.

Assembly and amplification of DmBCO, HsRDH12 and LmATF1 (wildtype and mutant) donor DNA expression cassettes. In order to convert beta-carotene into retinyl acetate, via the intermediates retinal and retinol, three expression cassettes containing *Drosophila melanogaster* beta-carotene oxidase (DmBCO according to *Saccharomyces cerevisiae* codon optimized SEQ ID NO:20), *Homo sapiens* retinol dehydrogenase (HsRDH12 according to *Saccharomyces cerevisiae* codon optimized SEQ ID NO:24) and Lachancea mirantina acetyl-transferase (LmATF1, wildtype according to SEQ ID NO:4 or mutant) genes are transformed into strain PRN1014_crtE_crtYB_crtI+ pCSN061.

Double-stranded donor DNA cassettes coding for DmBCO, HsRDH12 and LmATF1 (wildtype or mutant) genes are prepared via a Golden-Gate assembly reaction of individual promoter (P), orf (0) and terminator (T) sequences in an appropriate *E. coli* receiving backbone vector as described in Example 1 of WO2013144257A1. The promoter and terminator sequences originate from *Saccharomyces cerevisiae* strain S288C (Mortimer and Johnston, Genetics 113, p. 35-43, 1986). The TDH3 promoter and ENO1 terminator sequences, part of SEQ ID NO:33, are used to express DmBCO. The PGK1 promoter and GPM1 terminator sequences, part of SEQ ID NO:34, are used to express HsRDH12. The ENO2 promoter and ADH1 terminator sequences, part of SEQ ID NO:35 to SEQ ID NO:42, are used to express LmATF1 wildtype or mutant sequences. Promoter, ORF and terminator DNA sequences are synthesized at a synthetic DNA supplier, e.g. ATUM (Newark, CA, USA) and are delivered in separate standard cloning vectors. The receiving backbone vector (described in WO2013144257A1, Example 1) contains connector 25 and 2A sequences (part of SEQ ID NO:33), connector 2A and 2B sequences (part of SEQ ID NO:34) or connector 2B and 23 sequences (e.g. part of SEQ ID NO:35). The prepared sequences contain 50-basepair (bp) connector sequences at their 5' and 3' end that allow in vivo recombination of DNA fragment in *S. cerevisiae* as described in Example 1 of WO2013144257A1. The overview of sequences that are obtained is provided in Table 7.

The assembled POT cassettes are amplified via a PCR reaction with primers indicated in Table 7 and using the plasmids prepared by the Golden gate reactions as template to obtain donor DNA fragments for transformation to strain PRN1014_crtE_crtYB_crtI+pCSN061. The Q5 DNA polymerase (part of the Q5® High-Fidelity 2× Master Mix, New England Biolabs, supplied by Bioké, Leiden, the Netherlands. Cat no. M0492S) is used in the PCR reaction, which is performed according to manufacturer's instructions. The size of the PCR fragments is checked with standard agarose electrophoresis techniques. The PCR fragments are purified using the NucleoSpin Gel and PCR Clean-up kit (Machery-Nagel, distributed by Bioké, Leiden, the Netherlands) according to manufacturer's instructions. The DNA concentration is measured using the NanoDrop (ND-1000 Spectrophotometer, Thermo Fisher Scientific).

Amplification of donor DNA flank sequences. Genomic gDNA (gDNA) is isolated from a yeast strain of the CEN.PK lineage (for example CEN.PK2-1C, MATa; his3D1; leu2-3_112; ura3-52; trp1-289; MAL2-8c; SUC2) or from strain PRN1014 using the lithium acetate SDS method (Lõoke et al., BioTechniques 50, p. 325-328, 2011). Strain CEN.PK2-1C is available from the EUROSCARF collection (euroscarf.de, Frankfurt, Germany).

The isolated genomic DNA is used as a template in a PCR reaction as described above to obtain the PCR fragments that are used as donor for DNA flanking sequences (SEQ ID NO:53 and SEQ ID NO:54), comprising the overlap with the genomic DNA for genomic integration and including a connector sequence), using the specific forward and reverse primer combinations depicted in Table 7. The donor DNA flank sequences contain 50-bp connector sequences at the 5' or 3' position. The presence of connector sequences allows for in vivo recombination between connector sequences that are also part of the donor DNA expression cassettes, as described in Example 1 of WO2013144257A1.

TABLE 7

Donor DNA sequences to be transformed into strain
PRN1014_crtE_crtYB_crtI + pCSN061.
Forward (FW) and reverse (REV) primers
used for amplification are indicated with the
respective SEQ ID NOs (sequence listing).
Con denotes 50-bp unique connector sequences present
at the 5' and 3' end of the expression cassette sequence.

| SEQ ID NO: | Description donor DNA | FW primer | REV primer |
|---|---|---|---|
| 33 | con25-DmBCO-con2A expression cassette | 43 | 44 |
| 34 | con2A-HsRDH12-con2B expression cassette | 45 | 46 |
| 35 | con2B-LmATF1-con23 expression cassette | 47 | 48 |
| 36 | con2B-LmATF1_S480Q_V334L-con23 expression cassette | 47 | 48 |
| 37 | con2B-LmATF1_S480Q_V407I-con23 expression cassette | 47 | 48 |
| 38 | con2B-LmATF1_S480Q_G409A-con23 expression cassette | 47 | 48 |
| 39 | con2B-LmATF1_S480Q_V407I_H69A-con23 expression cassette | 47 | 48 |
| 40 | con2B-LmATF1_S480Q_G409A_V407I-con23 expression cassette | 47 | 48 |
| 41 | con2B-LmATF1_S480Q_G409A_V407I_I484L-con23 expression cassette | 47 | 48 |
| 42 | con2B-LmATF1_S480Q_G409A_V407I_H69A_I484L-con23 expression cassette | 47 | 48 |
| 53 | INT70 5'-con25 DNA flank sequence | 49 | 50 |
| 54 | con23-INT70 3' DNA flank sequence | 51 | 52 |

For more details see text.

Guide RNA expression cassette. The guide RNA expression cassette is ordered as a synthetic DNA cassette (gBlocks gene fragment at Integrated DNA Technologies, Leuven, Belgium). The guide RNA expression cassette (SEQ ID NO:55) consists of different elements as described in Example 9 of WO2016110512, including the INT70 genomic target (protospacer) sequence (SEQ ID NO:56). The INT70 guide RNA expression cassette contains overlapping sequences with the pRN1120 vector (SEQ ID NO:32) resulting, upon transformation and in vivo recombination in yeast, in a circular vector allowing selection on nourseothricin as explained in Example 9 of WO2016110512.

The gBlock is ligated into the pCR-BluntII-TOPO vector (Zero Blunt TOPO PCR Cloning Kit, Life Technologies, Grand Island, NY, USA) according to manufacturer's instructions. Using the TOPO vector containing the gBlock as template, Q5 DNA polymerase (Bioké, Leiden, the Netherlands) and the primers as set out in SEQ ID NO:57 and SEQ ID NO:58, the guide RNA expression cassette PCR fragment is generated in a PCR reaction according to manufacturer's instructions. The guide RNA expression cassette PCR fragment is purified using the NucleoSpin Gel and PCR Clean-up kit (Machery-Nagel, distributed by Bioké, Leiden, the Netherlands) according to manufacturer's instructions. The DNA concentration is measured using the NanoDrop (ND-1000 Spectrophotometer, Thermo Fisher Scientific).

Yeast transformation experiments. Strain PRN1014_crtE_crtYB_crtI+pCSN061 is transformed using the LiAc/salmon sperm (SS) carrier DNA/PEG method (Gietz and Woods, see above).

Prior to transformation, plasmid pRN1120 (SEQ ID NO:32) is linearized using restriction enzymes EcoRI and XhoI. Next, the linearized vector is purified using the NucleoSpin Gel and PCR Clean-up kit (Machery-Nagel, distributed by Bioke, Leiden, the Netherlands) according to manufacturer's instructions. The DNA concentration is measured using the NanoDrop (ND-1000 Spectrophotometer, Thermo Fisher Scientific).

An overview of the different transformation experiments is shown in Table 8. In each transformation experiment, the following amounts of donor DNA are added to the transformation mixture: 100-1000 ng of the linearized pRN1120 plasmid, 100-1000 ng of each donor expression cassette, 100-1000 ng of each donor DNA flank sequence and 100-1000 ng of the INT70 guide RNA expression cassette (SEQ ID NO:55). For example, 100 ng of the linearized pRN1120 plasmid, 200 ng of each donor expression cassette, 100 ng of each donor DNA flank sequence and 750 ng of the INT70 guide RNA expression cassette (SEQ ID NO:55), is added.

The donor DNA expression cassettes and DNA flank sequences assemble into a linear stretch of DNA through the 50-bp homologous connector sequences allowing integration of all donor DNA at the targeted INT70 locus, as depicted in FIG. 1. The INT70 integration site is located at the non-coding region between AAD14 (YNL331c) and GYP1 (YNL330c) located on chromosome XIV of the CEN.PK genome.

TABLE 8

Overview of transformation experiments ("#") performed in this
Example. The DmBCO expression cassette
(SEQ ID NO: 33), HsRDH12 expression
cassette (SEQ ID NO: 34), LmATF1 wildtype
expression cassette (SEQ ID NO: 35) or
LmATF1 mutant expression cassettes
(SEQ ID NO: 36-42) sequences are
transformed together with donor DNA flank sequences
(SEQ ID NO: 53 and SEQ ID NO: 54).

| # | ATF transformed | Donor DNA expression cassettes (SEQ ID NOs) |
|---|---|---|
| 1 | LmATF1 wt | 33; 34; 35 |
| 2 | LmATF1_S480Q_V334L | 33; 34; 36 |
| 3 | LmATF1_S480Q_V407I | 33; 34; 37 |
| 4 | LmATF1_S480Q_G409A | 33; 34;38 |
| 5 | LmATF1_S480Q_V407I_H69A | 33; 34; 39 |
| 6 | LmATF1_S480Q_G409A_V407I | 33; 34; 40 |
| 7 | LmATF1_S480Q_G409A_V407I_I484L | 33; 34; 41 |
| 8 | LmATF1_S480Q_G409A_V407I_H69A_I484L | 33; 34; 42 |

The transformation mixtures are plated on YPD-agar (10 grams per litre of yeast extract, 20 grams per litre of peptone, 20 grams per litre of dextrose, 20 grams per litre of agar) containing 200 μg nourseothricin (NatMX, Jena Bioscience, Germany) and 200 μg G418 (Sigma Aldrich, Zwijndrecht, the Netherlands) per ml. Alternatively, 20 grams per litre dextrose is replaced by 20 grams per litre xylose as C-source in the YP agar. Upon incubation at 30° C., colonies appear on the transformation plates.

Growth experiments and analysis. To demonstrate production of retinyl acetate using glucose or xylose as C-source the following procedure is followed: First, transformants resulting from the transformation experiment mentioned in Table 8 are individually inoculated in shake flasks containing 10 ml YP (10 grams per liter of yeast extract, 20 grams per liter of peptone) medium supplemented with 2% glucose or 2% xylose as C-source and grown in a shaking incubator at 30° C. and 250 rpm until sufficient growth is observed. Subsequently, an aliquot of the glucose or xylose precultures is transferred to 10 ml YP medium in a shake flask supplemented with 2% xylose such that an optical density of 0.1 to 1.0 is reached. Also, an aliquot of the glucose pre-cultures is transferred to 10 ml YP medium in a shake flask supplemented with 2% glucose such that an optical density of 0.1 to 1.0 is reached. As shake flasks, baffled and non-baffled shake flasks can be used. The liquid cultures are overlaid with 500 μl of mineral oil (Drakeol 5, Penreco, Karns City, PA USA). The cultures are grown in a shaking incubator for two to four days at 30° C. and a shaking speed between 250 and 800 rpm. The oil fraction is removed from the culture and analyzed by UPLC reveres phase column, with a photo-diode array detector, as described in Example 1.

Alternatively, transformants are tested as described by Sun et al. (ACS Synth Biol. 8 (9), p. 2131-2140, 2019).

Production of retinyl acetate from xylose and glucose in the pRN1014 derived transformants of each transformation experiment described in Table 8 is compared. It is expected that the percentage of retinyl acetate is increased when expressing a mutant ATF1 in *S. cerevisiae* growing on xylose, with ranges at least as obtained when growing on glucose or galactose

The invention claimed is:

1. A modified acetyl transferase enzyme comprising an amino acid sequence having at least 90% identity to SEQ ID NO:1, wherein:

the amino acid sequence comprises one or more substitute residue(s) relative to SEQ ID NO:1, the one or more substitute residue(s) are located at position(s) corresponding to position 68, 69, 72, 73, 171, 172, 173, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof according to SEQ ID NO:1, and the one or more substitute residue(s) is/are selected from the group consisting of: substitute residue corresponding to position 68 according to SEQ ID NO:1 is threonine, substitute residue corresponding to position 69 according to SEQ ID NO:1 is asparagine or serine or alanine, substitute residue corresponding to position 72 according to SEQ ID NO:1 is asparagine or lysine, substitute residue corresponding to position 73 according to SEQ ID NO:1 is leucine, substitute residue corresponding to position 171 according to SEQ ID NO:1 is lysine or asparagine, substitute residue corresponding to position 172 according to SEQ ID NO:1 is glycine, substitute residue corresponding to position 173 according to SEQ ID NO: 1 is leucine, substitute residue corresponding to position 174 according to SEQ ID NO:1 is isoleucine, substitute residue corresponding to position 176 according to SEQ ID NO:1 is alanine or glycine, substitute residue corresponding to position 178 according to SEQ ID NO:1 is valine, substitute residue corresponding to position 291 according to SEQ ID NO:1 is serine or glycine, substitute residue corresponding to position 292 according to SEQ ID NO:1 is alanine or serine or asparagine, substitute residue corresponding to position 294 according to SEQ ID NO:1 is leucine or valine, substitute residue corresponding to position 301 according to SEQ ID NO:1 is phenylalanine, substitute residue corresponding to position 307 according to SEQ ID NO:1 is isoleucine, substitute residue corresponding to position 308 according to SEQ ID NO:1 is valine, substitute residue corresponding to position 311 according to SEQ ID NO:1 is methionine or isoleucine, substitute residue corresponding to position 312 according to SEQ ID NO:1 is alanine, substitute residue corresponding to position 320 according to SEQ ID NO:1 is asparagine, substitute residue corresponding to position 322 according to SEQ ID NO:1 is valine or phenylalanine, substitute residue corresponding to position 334 according to SEQ ID NO:1 is methionine or leucine, substitute residue corresponding to position 362 according to SEQ ID NO:1 is alanine, substitute residue corresponding to position 405 according to SEQ ID NO:1 is alanine, substitute residue corresponding to position 407 according to SEQ ID NO:1 is isoleucine, substitute residue corresponding to position 409 according to SEQ ID NO:1 is alanine, substitute residue corresponding to position 480 according to SEQ ID NO:1 is glutamic acid or leucine or methionine or phenylalanine or glutamine, substitute residue corresponding to position 483 according to SEQ ID NO:1 is valine, substitute residue corresponding to position 484 according to SEQ ID NO:1 is leucine, substitute residue corresponding to position 490 according to SEQ ID NO:1 is isoleucine, substitute residue corresponding to position 492 according to SEQ ID NO:1 is valine, substitute residue corresponding to position 520 according to SEQ ID NO:1 is alanine, substitute residue corresponding to position 521 according to SEQ ID NO:1 is alanine or valine, substitute residue corresponding to position 522 according to SEQ ID NO:1 is serine or threonine, substitute residue corresponding to position 524 according to SEQ ID NO:1 is asparagine or serine, substitute residue corresponding to position 525 according to SEQ ID NO:1 is valine or isoleucine or arginine, and substitute residue corresponding to position 526 according to SEQ ID NO:1 is serine, and combinations thereof.

2. The modified enzyme according to claim 1, wherein the amino acid sequence comprises one substituted residue relative to SEQ ID NO: 1, wherein the substituted residue is at a position corresponding to position 68, 69, 72, 73, 171, 172, 173, 174, 176, 178, 291, 292, 294, 301, 307, 308, 311, 312, 320, 322, 334, 362, 405, 407, 409, 480, 483, 484, 490, 492, 520, 521, 522, 524, 525, or 526 according to SEQ ID NO:1.

3. The modified enzyme according to claim 1, wherein the amino acid sequence comprises a first, second or third set of two substituted residues relative to SEQ ID NO: 1, wherein the first set of substituted residues is at positions 480 and 409, the second set of substituted residues is at positions 480 and 407, and the third set of substituted residues is at positions 407 and 409 according to SEQ ID NO:1.

4. The modified enzyme according to claim 3, wherein the amino acid sequence further comprises one or more substitute residue(s) at position(s) corresponding to position 68, 69, 72, 311, 334, 484, and combinations thereof according to SEQ ID NO:1.

5. The modified enzyme according to claim 1, wherein the one or more substitute residue(s) are selected from the group consisting of Q68T, H69A, H69N, H69S, Q72K, Q72N, I73L, G171K, G171N, N172G, Q173L, V174I, S176A, S176G, L178V, A291G, A291S, G292A, G292N, G292S, F294L, F294V, Y301F, P3071, T308V, T311I, T311M, S312A, H320N, Y322F, Y322V, V334L, V334M, S362A, S405A, V407I, G409A, S480E, S480F, S480L, S480M, S480Q, L483V, I484L, V490I, D492V, I520A, C521A, C521V, A522S, A522T, D524N, D524S, Q525V, Q525I, Q525R, G526S, and combinations thereof, wherein the substitute residue(s) position(s) is/are according to SEQ ID NO:1.

6. The modified enzyme according to claim 1, wherein the modified enzyme's activity towards conversion or acetylation of retinol into retinyl acetate is increased by about 0.2 to 4-fold compared to the corresponding unmodified acetyl transferase enzyme.

7. The modified enzyme according to claim 1, which is expressed in a retinol-producing host cell.

8. The modified enzyme according to claim 1, wherein the amino acid sequence comprises the [NDEHCS]-H-x(3)-D-[GA] motif at positions corresponding to positions 218 to 224 according to SEQ ID NO:1, wherein "x" denotes an arbitrary amino acid and the histidine at the second position of the motif is part of the enzyme's binding pocket.

9. A retinoid-producing host cell expressing the modified enzyme according to claim 6.

10. A process for the production of retinoids, comprising cultivating the host cell according to claim 9 under suitable culture conditions using a carbon source comprising glucose, fructose, raffinose, lactose, galactose, glycerol, xylose, arabinose, sucrose and/or maltose.

11. The process according to claim 10, wherein the retinoids produced comprise retinyl acetate at a percentage of about 0.2 to 4× higher compared to retinoids produced by a corresponding reference host cell expressing the corresponding unmodified acetyl transferase enzyme without said one or more substitute residue(s).

12. A process for production of retinyl acetate comprising providing the retinol-producing host cell according to claim 9, cultivating said host cell in a suitable culture medium under suitable culture conditions, and isolating and/or purifying the retinyl acetate from the medium.

13. The modified enzyme according to claim 8, wherein the motif comprises the sequence of [NDE]-H-x(3)-D-[GA].

14. The modified enzyme according to claim 8, wherein the motif comprises the sequence of [ND]-H-x(3)-D-[GA].

15. The modified enzyme according to claim 8, wherein the motif comprises the sequence of N—H-x(3)-D-[GA].

16. The process according to claim 10, wherein the host cell is a *Yarrowia* or *Saccharomyces* cell.

17. The process according to claim 11, wherein the host cell is a *Yarrowia* or *Saccharomyces* cell.

18. The process according to claim 12, wherein the host cell is a *Yarrowia* or *Saccharomyces* cell.

19. The modified enzyme according to claim 1, wherein the one or more substitute residue(s) are selected from the group consisting of V407I and H69S, V407I and Q72K, V407I and T311I, V407I and V334L, V407I and S480L, V407I and I484L, G409A and H69N, G409A and H69S, G409A and H69A, G409A and Q72K, G409A and T311I, G409A and V334L, G409A and V407I, G409A and S480L-489K, S480Q and Q68T, S480Q and H69N, S480Q and H69S, S480Q and H69A, S480Q and Q72K, S480Q and T311I, S480Q and V334L, S480Q and V407I, S480Q and G409A, and S480Q and I484L, wherein the substitute residue(s) position(s) is/are according to SEQ ID NO:1.

20. The modified enzyme according to claim 1, wherein the one or more substitute residue(s) are selected from the group consisting of G409A/V407I/H69N, G409A/V407I/Q72K, G409A/V407I/T311I, G409A/V407I/V334L, G409A/V407I/S480L, G409A/V407I/I484L, S480Q/V407I/Q68T, S480Q/V407I/H69N, S480Q/V407I/H69S, S480Q/V407I/H69A, S480Q/V407I/Q72K, S480Q/V407I/T311I, S480Q/V407I/V334L, S480Q/V407I/I484L, S480Q/G409A/Q68T, S480Q/G409A/H69A, S480Q/G409A/H69N, S480Q/G409A/I484L, S480Q/G409A/V407I/H69N, S480Q/G409A/V407I/H69A, S480Q/G409A/V407I/H69S, S480Q/G409A/V407I/Q72K, S480Q/G409A/V407I/T311I, S480Q/G409A/V407I/V334L, S480Q/G409A/V407I/I484L, and S480L/G409A/V407I/T311I, wherein the substitute residue(s) position(s) is/are according to SEQ ID NO:1.

* * * * *